(12) United States Patent
Rong et al.

(10) Patent No.: US 11,878,989 B2
(45) Date of Patent: Jan. 23, 2024

(54) METHOD FOR PREPARING L-ERYTHROBIOPTERIN COMPOUND

(71) Applicant: Shanghai Forefront Pharma Co., Ltd., Shanghai (CN)

(72) Inventors: Bin Rong, Shanghai (CN); Lizhi Zhao, Shanghai (CN); Wei Li, Shanghai (CN); Yi Ren, Shanghai (CN); Lingui Zhu, Shanghai (CN)

(73) Assignee: SHANGHAI FOREFRONT PHARMA CO., LTD., Shanghai (CN)

( * ) Notice: Subject to any disclaimer, the term of this patent is extended or adjusted under 35 U.S.C. 154(b) by 0 days.

(21) Appl. No.: 17/636,193

(22) PCT Filed: Aug. 18, 2020

(86) PCT No.: PCT/CN2020/109818
§ 371 (c)(1),
(2) Date: Feb. 17, 2022

(87) PCT Pub. No.: WO2021/032088
PCT Pub. Date: Feb. 25, 2021

(65) Prior Publication Data
US 2022/0298178 A1   Sep. 22, 2022

(30) Foreign Application Priority Data

Aug. 19, 2019   (CN) .......................... 201910764541.4
Aug. 12, 2020   (CN) .......................... 202010806347.0

(51) Int. Cl.
*C07D 241/20*   (2006.01)
*C07F 5/02*   (2006.01)

(52) U.S. Cl.
CPC ............ *C07F 5/022* (2013.01); *C07D 241/20* (2013.01)

(58) Field of Classification Search
CPC .................................................. C07D 241/20
See application file for complete search history.

(56) References Cited

PUBLICATIONS

Int'l Search Report dated Oct. 28, 2020 in Int'l Application No. PCT/CN2020/109818.
Taylor et al, "Pteridines. XXXVII. A total synthesis of L-erythrobiopterin and some related 6-(polyhydroxyalkyl)pterins," Journal of the American Chemical Society, vol. 98, No. 8, pp. 2301-2307 (Dec. 31, 1976).
Taylor et al, "Pteridines. XXXIII. Unequivocal total synthesis of L-erythro-Biopterin," Journal of the American Chemical Society, vol. 96, No. 21, pp. 6781-6782 (Dec. 31, 1974).
Degraw et al., "Synthesis of Biopterin-8a-13C", Journal of Labelled Compounds and Radiopharmaceuticals, vol. 16, No. 4, pp. 559-565 (Dec. 1979).
Zhang et al., "A New Synthesis of Ciliapterin and Dictyopterin. Ene reactions of (Alkenylamino)-nitroso-pyrimidines", Helvetica Chimica Acta, vol. 91, No. 12, pp. 2351-2360 (Dec. 2008).
Schircks et al., "Pterine chemistry. 84. A New, Regiospecific Synthesis of L-Biopterin", Helvetica Chimica Acta, vol. 68, No. 6, pp. 1639-1643 (Dec. 1985).
Jacobi et al., "Unequivocal Synthesis of Euglenapterin", Journal of Organic Chemistry, vol. 46, No. 26, pp. 5416-5418 (Dec. 1981).
Office Action dated Oct. 7, 2022 in IN Application No. 202227009388.
Database Registry [Online], Retrieved from STN, RN:1823427-26-4, 201 Dec. 6, 2015.
Extended European search report dated Jul. 14, 2023 in EP Application No. 20855543.3.

(Continued)

*Primary Examiner* — Golam M Shameem
(74) *Attorney, Agent, or Firm* — Panitch Schwarze Belisario & Nadel LLP

(57) ABSTRACT

A method for preparing an L-erythrobiopterin compound is provided. The L-erythrobiopterin compound has a structure represented by formula (I), and is mainly prepared from a compound having a structure represented by formula (II) or (III) through dihydroxylation. The preparation method of the L-erythrobiopterin compound is high in production efficiency, low in cost, environmentally friendly, and suitable for industrial production.

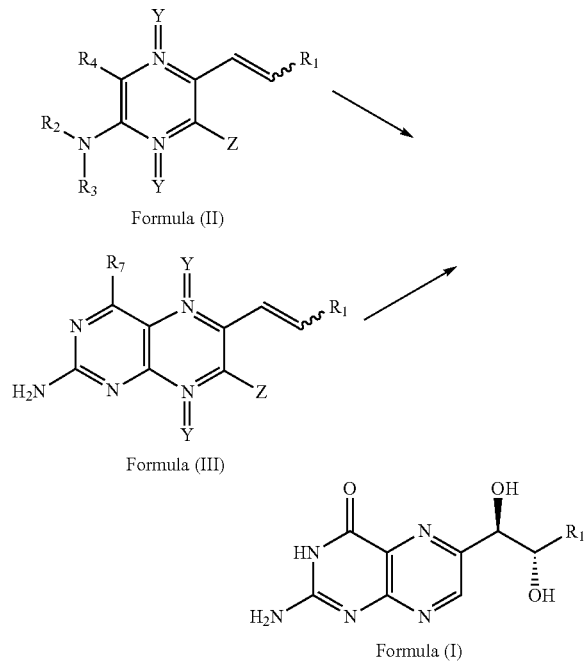

19 Claims, 1 Drawing Sheet

(56) References Cited

PUBLICATIONS

Wu et al., "Enantioselective trans-Dihydroxylation of Aryl Olefins by Cascade Biocatalysis with Recombinant *Escherichia coli* Coexpressing Monooxygenase and Epoxide Hydrolase," ACS Catalysis, vol. 4, pp. 409-420 (2014).

Kolb et al., "Catalytic Asymmetric Dihydroxylation," Chemical Reviews, vol. 94, No. 8, pp. 2483-2547 (1994).

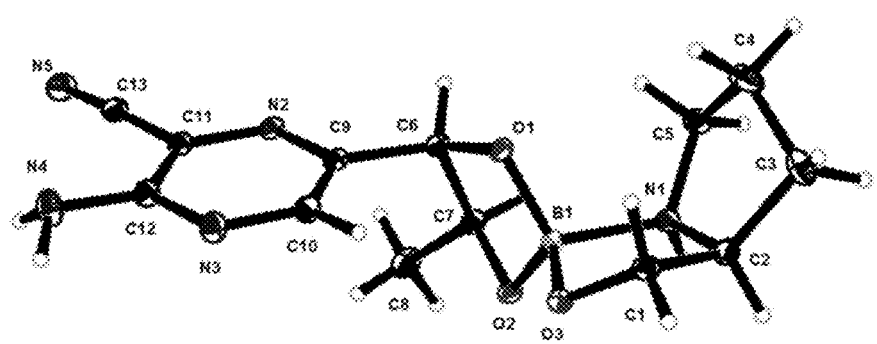
PLAT791 ALERT 4 G Model has Chirality at N1    (Chiral SPGR)    S Verify
And 3 other PLAT791 Alerts
PLAT791 ALERT 4 G Model has Chirality at C2    (Chiral SPGR)    S Verify
PLAT791 ALERT 4 G Model has Chirality at C6    (Chiral SPGR)    R Verify
PLAT791 ALERT 4 G Model has Chirality at C7    (Chiral SPGR)    S Verify

METHOD FOR PREPARING L-ERYTHROBIOPTERIN COMPOUND

CROSS-REFERENCE TO RELATED APPLICATIONS

This application is a Section 371 of International Application No. PCT/CN2020/109818, filed Aug. 18, 2020, which was published in the Chinese language on Feb. 25, 2021 under International Publication No. WO 2021/032088 A1, which claims priority under 35 U.S.C. § 119(b) to Chinese Application No. 201910764541.4, filed Aug. 19, 2019 and Chinese Application No. 202010806347.0, filed Aug. 12, 2020, the disclosures of which are incorporated herein by reference in their entireties.

TECHNICAL FIELD

The present invention relates to the technical field of drug preparation, and particularly to the preparation method of L-erythro biopterin compound.

BACKGROUND OF THE INVENTION

The L-erythro biopterin compound represented by formula (I) is an important intermediate for most drugs, especially for the sapropterin drugs. For example, (R)-2-amino-6-[(1R,2S)-1,2-dihydroxypropyl]-5,6,7,8-tetrahydro-4(3H)-pteridinone (BH4) represented by formula (Ib) is an essential coenzyme in hydroxylation reactions and oxygenases in vivo and is the most important coenzyme of nitric oxide synthase (NOS). Its hydrochloride (i.e., sapropterin dihydrochloride, represented by structural formula (Ic)) has been approved by many countries for the treatment of phenylketonuria.

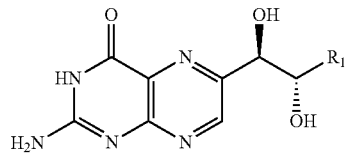

Formula (I)

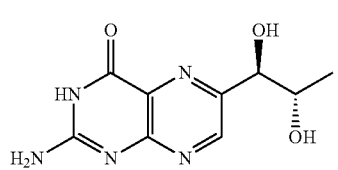

Formula (Ia)

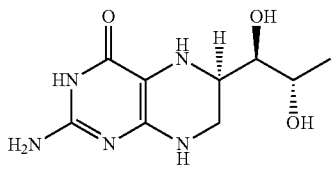

Formula (Ib)

At present, sapropterin dihydrochloride is mainly synthesized by hydrogenation/reduction of the compound represented by formula (Ia).

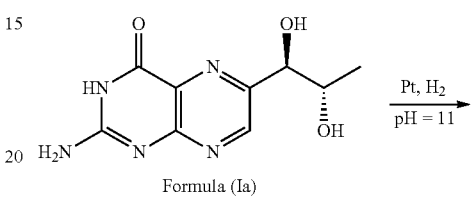

Formula (Ia)

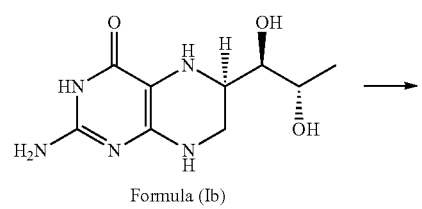

Formula (Ib)

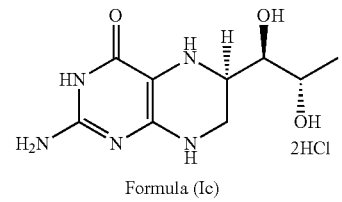

Formula (Ic)

Therefore, research and development is currently focused on the safe and efficient method to produce L-erythro biopterin compound represented by formula (Ia).

At present, there are many reports on the synthesis of L-erythro biopterin compound. For example, Andrews et al. (J. Chem. Soc. 1969, 928) reported the preparation of biopterin by condensation of 5-deoxy-L-arabinose with 2-amino-4-chloro-3-nitro-6-hydroxypyrimidine. However, both the optical purity and chemical purity are insufficient and scale-up production is unachievable.

Welustock J. (U.S. Pat. No. 3,505,329), and Taylor E. C. (J. Am. Chem. Soc. 1979, 98, 2301) reported a method with higher optical selectivity, as shown in the following route:

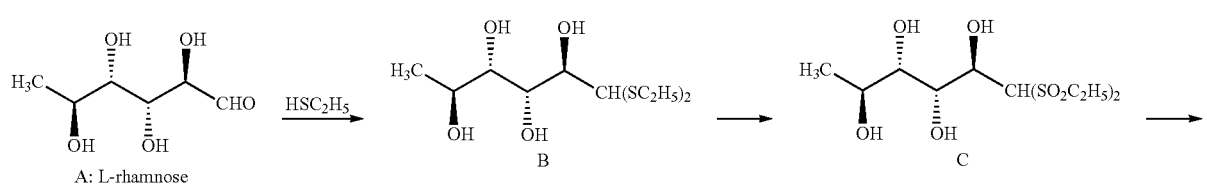

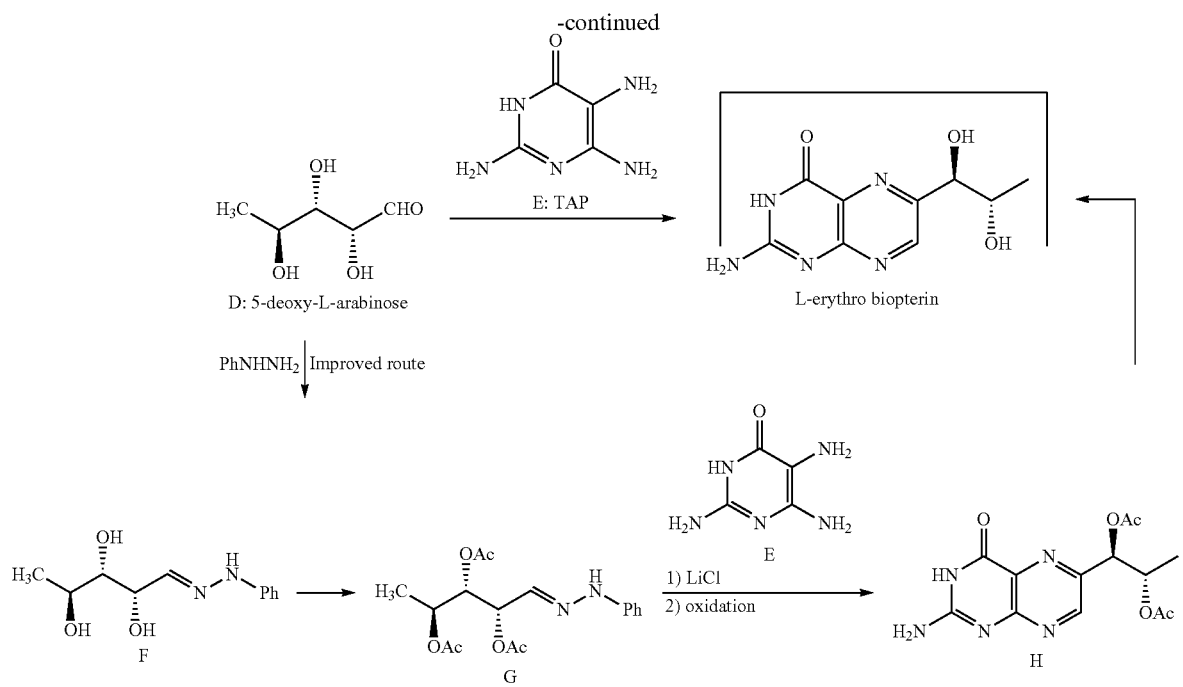

L-rhamnose is used as the raw material, which reacts with ethanethiol to generate thioacetal, which is oxidized to sulfone, and then one carbon is removed by alkali treatment to obtain 5-deoxy-L-arabinose (D). Then, 5-deoxy-L-arabinose reacts with 2,4,5-triamino-6-hydroxypyrimidine (TAP) to generate L-erythro biopterin. After subsequent improvements (*Helv chim acta* 1985:1639), the method has become the current industrialized route. In the method, 5-deoxy-L-arabinose (D) is first treated with phenylhydrazine, and then treated with acetic anhydride to convert to corresponding acetylphenylhydrazone (G), followed by cyclization with TAP. The obtained product is not separated but immediately oxidized to obtain the acetylated L-erythro biopterin, which is further deprotected to obtain L-erythro biopterin.

However, this industrial route has following significant deficiencies: 1) The synthesis of the critical intermediate 5-deoxy-L-arabinose involves condensation of L-rhamnose with ethanethiol with a strong foul smell to obtain acetal, which is complicated in operations and causes serious pollution, and thus is no longer used in industry at present; 2) The intermediate 5-deoxy-L-arabinose itself is unstable, cannot be stored for a long time, and thus must be prepared immediately before use; 3) The intermediates in the steps for preparing 5-deoxy-L-arabinose are oily substances and unstable, so all the intermediates from C to L-erythro biopterin cannot be purified, which makes the process difficult to control the quality and carry out GMP production; 4) The process for preparing L-erythro-biopterin by condensation of 5-deoxy-L-arabinose derivative with 2,4,5-triamino-6-hydroxypyrimidine (TAP) shows poor selectivity, numerous impurities and low yield; and (5) The generated L-erythro-biopterin is extremely difficult to be purified due to its extremely poor solubility in common solvents, and the poor quality directly and adversely affects the quality of sapropterin hydrochloride subsequently prepared by hydrogenation.

Based on the current technologies, the improvement in process of L-erythro-biopterin compound worldwide mostly focus on the preparation of 5-deoxy-L-arabinose, especially using other reagents instead of thiol to reduce odor and pollution. There is no significant progress in the condensation of 5-deoxy-L-arabinose derivative with TAP, and the raw materials are expensive, the route is long, and the yield is low, resulting in high production costs and low safety performance, which cannot meet the production needs in modern pharmaceutical industry. Therefore, it is urgent to develop a preparation method of L-erythro biopterin compound, which is of high efficiency, low cost, is environment-friendly, and suitable for industrial production.

SUMMARY OF THE INVENTION

Based on this situation, the present invention provides a method for preparing L-erythro biopterin compound, which is of high production efficiency, low cost, is environment-friendly, and suitable for industrial production.

Intermediate represented by structural formula (IVa-1), (IVa-2), (IVa-3), (IVa-4), (IVa) or (IVa'):

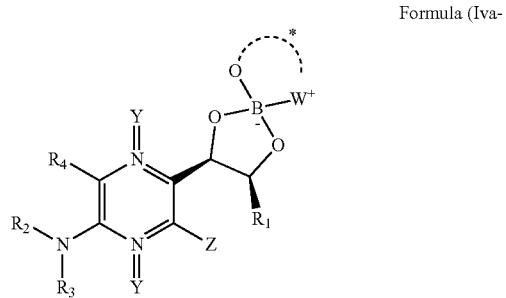

Formula (Iva-

-continued

Formula (Iva-2)

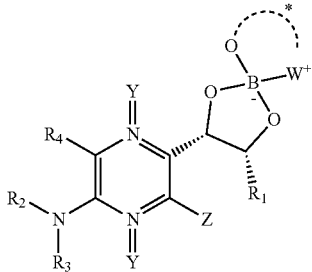

Formula (Iva-3)

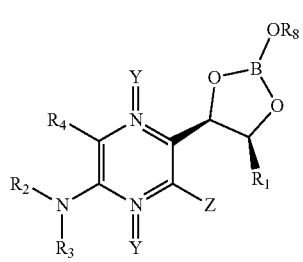

Formula (Iva-4)

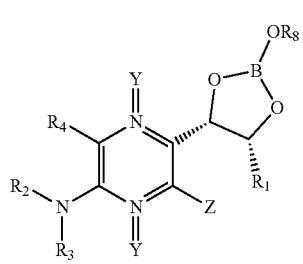

Formula (Iva)

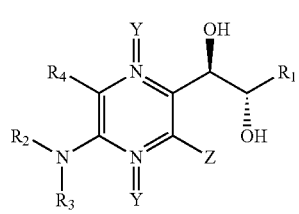

Formula (Iva')

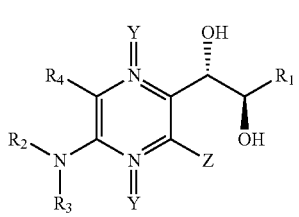

In which,

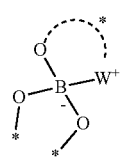

represents the structure generated by the reaction of dihydroxyl, the first reagent and the second reagent;

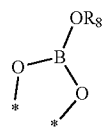

represents the structure generated by the reaction of dihydroxyl and the first reagent;

The first reagent is boric acid ester or boric acid;

The second reagent is chiral amino alcohol;

W is $NH_x$, and X is 0, 1 or 2;

$R_1$ is a substituted or unsubstituted alkyl, a substituted or unsubstituted cycloalkyl, a substituted or unsubstituted heterocycloalkyl, a substituted or unsubstituted aryl, or a substituted or unsubstituted heteroaryl; $R_2$ and $R_3$ are independently a hydrogen atom or an amino-protecting group; and $R_2$ and $R_3$ together with the nitrogen atom connected to $R_2$ and $R_3$ can form a cyclic lactim group;

$R_4$ is —$COOR_5$, —$CONR_6$ or —CN;

$R_5$ and $R_6$ are independently a hydrogen atom, a substituted or unsubstituted alkyl, a substituted or unsubstituted cycloalkyl, a substituted or unsubstituted heterocycloalkyl, a substituted or unsubstituted aryl, or a substituted or unsubstituted heteroaryl;

Z is a hydrogen atom or a leaving group;

Y is O or absent.

The method for preparing the intermediate mentioned above includes the following steps:

Mix the compound to be separated (a mixture of compounds represented by formulas (IVa) and (IVa')), the first reagent, the second reagent and the aprotic solvent, and heat to reflux. After the reaction is completed, crystallize to obtain the intermediate represented by structural formula (IVa-1) or (IVa-2);

Formula (Iva)

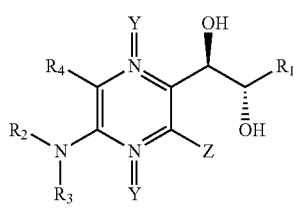

Formula (Iva')

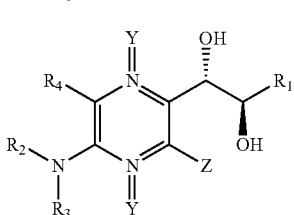

The intermediates mentioned above can be used to prepare L-erythro biopterin compound.

It is a method for preparing L-erythro biopterin compound. The L-erythro biopterin compound is represented by structural formula (I), and prepared by dihydroxylation of the compound represented by formula (II) or formula (III);

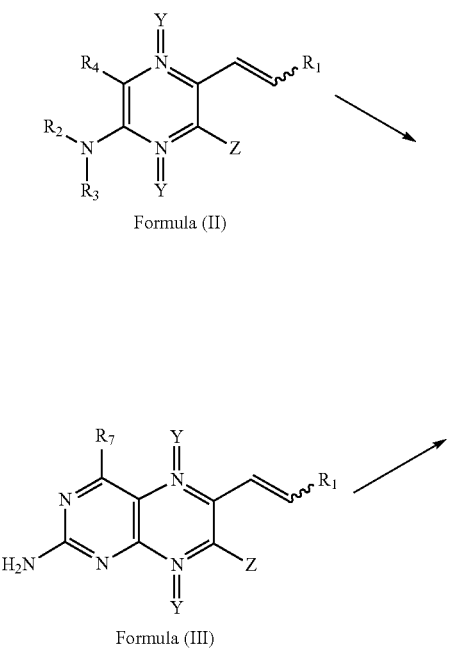

Formula (II)

Formula (I)

Formula (III)

In which,

Y is O or absent;

Z is a hydrogen atom or a leaving group;

$R_1$ is a substituted or unsubstituted alkyl, a substituted or unsubstituted cycloalkyl, a substituted or unsubstituted heterocycloalkyl, a substituted or unsubstituted aryl, or a substituted or unsubstituted heteroaryl; $R_2$ and $R_3$ are independently a hydrogen atom or an amino-protecting group; and $R_2$ and $R_3$ together with the nitrogen atom connected to $R_2$ and $R_3$ can form a cyclic lactim group;

$R_4$ is —$COOR_5$, —$CONR_6$ or —CN;

$R_5$ and $R_6$ are independently a hydrogen atom, a substituted or unsubstituted alkyl, a substituted or unsubstituted cycloalkyl, a substituted or unsubstituted heterocycloalkyl, a substituted or unsubstituted aryl, or a substituted or unsubstituted heteroaryl;

$R_7$ is —OH or —$NH_2$.

L-erythro biopterin compound prepared by the above-mentioned method for preparing L-erythro biopterin compound.

A method for preparing sapropterin drugs includes the following steps:

Prepare the L-erythro biopterin compound represented by formula (I) by the above-mentioned method for preparing L-erythro biopterin compound;

allow the L-erythro biopterin compound represented by formula (I) to undergo hydrogenation/reduction.

The L-erythro biopterin compound can be used to prepare drugs for treating phenylketonuria and hyperphenylalaninemia.

The method for preparing L-erythro biopterin compound can be used to prepare drugs for treating phenylketonuria and hyperphenylalaninemia.

BRIEF DESCRIPTION OF THE DRAWINGS

FIG. 1 shows the single crystal structure of compound 3a.

DETAILED DESCRIPTION OF THE INVENTION

For the purpose of understanding the present invention, a more comprehensive description of the present invention is given below, and preferred embodiments of the present invention are given. However, the present invention can be embodied in a variety of different forms and should not be limited to the embodiments described herein. On the contrary, these embodiments are provided for the purpose of more thorough and comprehensive understanding of the public disclosures of the present invention.

Unless defined otherwise, all technical and scientific terms used herein have the same meanings as commonly understood by the technicians in the field of the present invention. The terminology used in the patent specification of the present invention is given for the purpose of describing specific embodiments only, and is not intended to limit the present invention. The term "and/or" used herein includes any and all combinations of one or more of the relevant listed items.

Explanation of Terms

In the present invention, unless otherwise stated in the present invention, the meaning denoted by the same symbol should be understood as having the same meaning. In addition, unless otherwise stated, each term (including substituent abbreviations, reagent name abbreviations, etc.) in the present invention should be understood as having the ordinary meaning in the field.

In the present invention, a leaving group should be understood as the ordinary meaning in the field, referring to an atom or a functional group that can be removed from a large molecule in a chemical reaction. It is apprehensible that, unless otherwise stated, in reaction steps involving compounds containing a leaving group, including the steps of introducing and removing a leaving group, the introduction and removal of a leaving group can be done by methods commonly used in the field according to the specific type of the leaving group used, which will not be specifically limited herein.

In the present invention, the amino-protecting group should be understood as the ordinary meaning in the field, referring to the protecting group of amino group. It is apprehensible that, unless otherwise stated, in reaction steps involving compounds containing a protecting group, including the steps of introducing and removing a protecting group, the introduction and removal of a protecting group can be done by methods commonly used in the field according to the specific type of the protecting group used, which will not be specifically limited herein.

In the present invention, "substituted or unsubstituted" means that the defined group can be substituted or unsubstituted. When a defined group is substituted, it should be understood as being substituted by any one group acceptable in the field, including but not limited to: alkyl with 1 to 20 carbon atoms, cycloalkyl with 3 to 20 ring atoms, heterocyclyl with 3 to 20 ring atoms, aryl with 5 to 20 ring atoms, heteroaryl with 5 to 20 ring atoms, silicyl, carbonyl, alkoxycarbonyl, aryloxycarbonyl, carbamoyl, haloformyl, formyl, —NRR', cyano, isocyano, isocyanate group, thiocyanate group, isothiocyanate group, hydroxyl, trifluoromethyl, nitro, or halogen. The groups can be further substituted with acceptable substituents in the field. It is apprehensible that each of R and R' in —NRR' is independently substituted by an acceptable group in the field, including but not limited to, H, alkyl with 1 to 6 carbon atoms, cycloalkyl with 3 to 8 ring atoms, heterocyclyl with 3 to 8 ring atoms, aryl with 5 to 20 ring atoms, or heteroaryl with 5 to 10 ring atoms. The alkyl with 1 to 6 carbon atoms, cycloalkyl with 3 to 8 ring atoms, heterocyclyl with 3 to 8 ring atoms, aryl with 5 to 20 ring atoms, or heteroaryl with 5 to 10 ring atoms can be further substituted by any one or more of the following groups: $C_{1-6}$ alkyl, cycloalkyl with 3 to 8 ring atoms, heterocyclyl with 3 to 8 ring atoms, halogen, hydroxyl, nitro or amino.

In the present invention, a site not labeled with a stereoconfiguration should be understood to include a variety of stereoconfigurations that can exist stably.

"Alkyl" refers to a saturated aliphatic hydrocarbyl, including straight and branched chain groups. $C_1$-$C_6$ alkyl refers to an alkyl of 1 to 6 carbon atoms. Non-limiting embodiments include: methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, and 2,3-dimethylbutyl. $C_1$-$C_4$ alkyl refers to an alkyl of 1 to 4 carbon atoms. In one embodiment, $C_1$-$C_4$ alkyl groups include methyl, ethyl, n-propyl, isopropyl, n-butyl, isobutyl, tert-butyl, and sec-butyl. The alkyl can be substituted or unsubstituted, and when substituted, the substituent can be substituted at any available connection point.

"Cycloalkyl" refers to a saturated or partially unsaturated monocyclic or polycyclic cyclic hydrocarbyl substituent. The 3-8 membered cycloalkyl refers to a cycloalkyl containing 3 to 8 carbon atoms. In one embodiment, the 3-8 membered monocyclic cycloalkyl groups include cyclopropyl, cyclobutyl, cyclopentyl, cyclopentenyl, cyclohexyl, cyclohexenyl, cyclohexadienyl, cycloheptyl, cycloheptatrienyl, and cyclooctyl, etc. Polycyclic cycloalkyl includes spiro, fused and bridged cycloalkyl. The cycloalkyl can be substituted with one or more substituents.

"Heterocyclyl" refers to a saturated or partially unsaturated monocyclic or polycyclic cyclic hydrocarbyl substituent, in which one or more ring atoms are heteroatoms selected from nitrogen, oxygen or $S(O)_m$ (in which m is an integer from 0 to 2), preferably nitrogen or oxygen heteroatoms, excluding the ring portion of —O—O—, —O—S— or —S—S—, and the remaining ring atoms are carbon. The 4-10 membered heterocyclyl refers to a ring of 4 to 10 ring atoms, in which 1 to 3 members are heteroatoms. The preferred heterocyclyl ring contains from 5 to 6 ring atoms, in which 1 to 2 members are heteroatoms. In one embodiment, monocyclic heterocyclyl groups include dihydrofuranyl, tetrahydrofuranyl, pyrrolidinyl, piperidinyl, piperazinyl, morpholinyl, thiomorpholinyl or homopiperazinyl, etc.

"Aryl" refers to an all-carbon monocyclic or fused polycyclic group having a conjugated π-electron system (i.e., a ring sharing adjacent pairs of carbon atoms), preferably groups having from 6 to 10 members, more preferably phenyl and naphthyl, most preferably phenyl. The aryl ring can be fused to a heteroaryl, heterocyclyl or cycloalkyl ring, and the aryl can be substituted or unsubstituted.

"Heteroaryl" refers to a heteroatom-containing aryl, in which heteroatoms include oxygen, sulfur and nitrogen. The heteroaryl is preferably a 5- or 6-membered group, such as a furanyl, thienyl, pyridyl, pyrrolyl, N-alkylpyrrolyl, pyrimidinyl, pyrazinyl, imidazolyl, tetrazolyl, etc. The heteroaryl ring can be fused to an aryl, heterocyclyl or cycloalkyl ring, and the ring connected to the parent structure is the heteroaryl ring. The heteroaryl can be substituted or unsubstituted.

In the present invention, the substituent "amino group" includes primary, secondary, or tertiary amino groups. Specifically, the amino group includes —$NR_{16}R_{17}$, in which $R_{16}$ and $R_{17}$ are hydrogen atom or any optional group, e.g., H, substituted or unsubstituted straight chain alkyl, substituted or unsubstituted branched alkyl, substituted or unsubstituted cycloalkyl, substituted or unsubstituted heterocyclyl, substituted or unsubstituted aryl, or substituted or unsubstituted heteroaryl, etc.

"Silicyl" refers to —Si (alkyl)$_3$, and the three alkyl groups connected to silicon can be the same or different from each other.

The cyclic lactim group has a structure

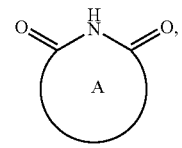

the number of ring atoms contained in ring A is not specifically limited, it can be a 5-membered ring, 6-membered ring, etc., e.g., glutarimide, succinimide, etc.

In the present invention, the abbreviations are given in the table below:

| Abbreviations | English name |
| --- | --- |
| Me | Methyl |
| TBS | t-butyldimethylsilyl |
| Boc | t-butyloxycarboryl |
| Cbz | Benzyloxycarbonyl |
| Ac | Acetyl |
| Ts | p-toluenesulfonyl |
| Ms | Mesyl (methanesulfonyl) |

| Abbreviations | English name |
|---|---|
| Bz | Benzoyl |
| Bn | Benzyl |
| PMB | p-methoxybenzyl |
| schiff base | Schiff base |
| dppf | 1,1'-bis(diphenylphosphino)ferrocene |
| Xantphos | 4,5-bis(diphenylphosphino)-9,9-dimethylxanthene |
| Xphos | 2-dicyclohexylphosphino-2',4',6'-triisopropylbiphenyl |
| DBU | 1,8-diazabicyclo[5.4.0]undec-7-ene |
| NMP | l-methyl-2-pyrrolidinone |
| THF | Tetrahydrofuran |
| 2-MeTHF | 2-methyltetrahydrofuran |
| ACN | Acetonitrile |
| MIBK | Methyl isobutyl ketone |
| ee | Enantiomeric excess |
| er | Enantiomer ratio |
| dr | Diastereomer ratio |

One embodiment of the present invention provides intermediate represented by structural formula (IVa-1), (IVa-2), (IVa-3), (IVa-4), (IVa) or (IVa'):

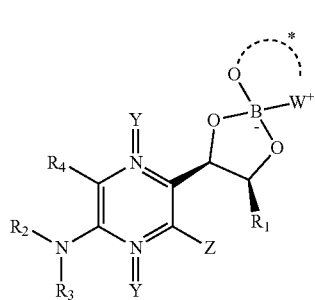

Formula (IVa-1)

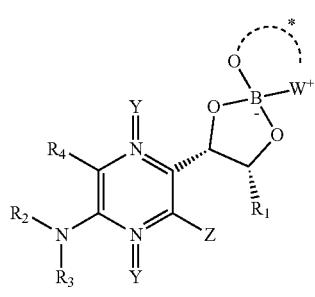

Formula (IVa-2)

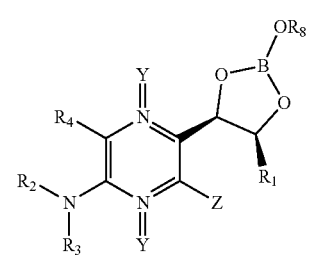

Formula (IVa-3)

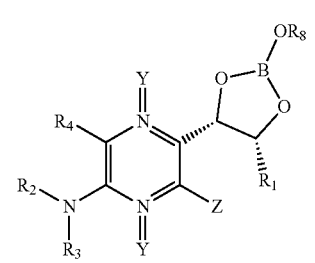

Formula (IVa-4)

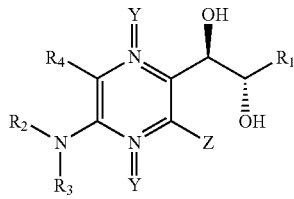

Formula (IVa)

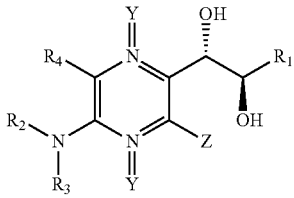

Formula (IVa')

In which,

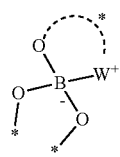

represents the structure generated by the reaction of dihydroxyl, the first reagent and the second reagent;

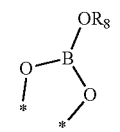

represents the structure generated by the reaction of dihydroxyl and the first reagent;

The first reagent is boric acid ester or boric acid;

The second reagent is chiral amino alcohol, chiral amino acid, chiral amino acid ester or chiral diol;

W is O or $NH_x$, and X is 0, 1 or 2;

$R_1$ is a substituted or unsubstituted alkyl, a substituted or unsubstituted cycloalkyl, a substituted or unsubstituted heterocycloalkyl, a substituted or unsubstituted aryl, or a substituted or unsubstituted heteroaryl;

$R_2$ and $R_3$ are independently a hydrogen atom, or an amino-protecting group; among them, the amino-protecting group includes but is not limited to: -Boc, -Cbz, —Ac, -Ts, -Ms, -Bz, -Bn, -PMB, or schiff base; and $R_2$ and $R_3$ together with the nitrogen atom connected to $R_2$ and $R_3$ can form a cyclic lactim group; $R_4$ is —$COOR_5$, —$CONR_6$ (i.e., $CONHR_6$) or —CN;

Z is a hydrogen atom or a leaving group; among them, the leaving group includes but is not limited to: halogen (e.g., Cl, Br, I), $OSO_nR_9$, $OCOR_{10}$ or $OPO_2R_{11}$. $R_9$, $R_{10}$, or $R_{11}$ is independently selected from: —$CF_3$, alkyl, phenyl, or alkyl-substituted phenyl (e.g., tolyl). n is 0, 1 or 2, and the silicyl group can be a silyl group, etc.

Y is O or absent.

In one embodiment, $R_1$ is selected from $C_{1-6}$ alkyl, 3-8 membered cycloalkyl, 3-10 membered aryl, 3-10 membered heteroaryl, TMS, TBS, or —CH2X; X is a leaving group. In one embodiment, $R_1$ is selected from $C_{1-6}$ alkyl, cyclopropyl, phenyl, pyridyl, TMS, TBS, or —$CH_2X$; X is a leaving group. In one embodiment, $R_1$ is methyl.

$R_5$ and $R_6$ are independently a hydrogen atom, or a substituted or unsubstituted $C_{1-20}$ alkyl. In which, $C_{1-20}$ alkyl can be further substituted by $C_{1-6}$ alkyl, 3-8 membered cycloalkyl, 3-10 membered aryl, 3-10 membered heteroaryl, hydroxyl, halogen, amino, cyano, or $C_{1-4}$ alkoxy.

Further, $R_5$ and $R_6$ are independently a hydrogen atom, or a substituted or unsubstituted $C_{1-6}$ alkyl. $C_{1-6}$ alkyl can be further substituted by $C_{1-4}$ alkyl, 3-8 membered cycloalkyl, 3-10 membered aryl, 3-10 membered heteroaryl, hydroxyl, halogen, amino, cyano, or $C_{1-4}$ alkoxy.

In one embodiment, $R_4$ is —CN.

In one embodiment, Y is absent, Z is a hydrogen atom, $R_4$ is a cyano, and $R_1$ is a methyl.

It is apprehensible that the $R_8$ group in

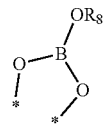

is determined according to the selected boric acid ester.

Further, $R_8$ is a substituted or unsubstituted alkyl group; furthermore, $R_8$ is a substituted or unsubstituted $C_{1-10}$ alkyl group, or a substituted or unsubstituted $C_{3-10}$ cycloalkyl group; furthermore, $R_8$ is a substituted or unsubstituted $C_{1-8}$ alkyl group or a substituted or unsubstituted $C_{3-8}$ cycloalkyl group; and furthermore, $R_8$ is a substituted or unsubstituted $C_{1-6}$ alkyl group or $C_{3-6}$ cycloalkyl group;

It is apprehensible that the boric acid ester in the present invention can be any acceptable boric acid ester reagent in this field; in one embodiment, the boric acid ester is selected from: trimethyl borate, triethyl borate, triisopropyl borate or isopropoxyboronic acid pinacol ester; in addition, the chiral amino alcohol can be any acceptable chiral amino alcohol in the field; in one embodiment, the chiral amino alcohol is selected from: L-phenylglycinol, L-prolinol, L-phenylalaninol, (S)-(−)-α,α-diphenylprolinol, quinine or cinchoni, so as to obtain the product of the desired configuration with higher ee value and yield. In the present invention, the chiral amino acid can be any acceptable chiral amino acid in the field; in one embodiment, the chiral amino acid is selected from the following chiral amino acids: L-phenylalanine, L-alanine, L-proline, L-leucine, L-valine, L-phenylglycine, etc. In the present invention, the chiral amino acid ester can be any acceptable chiral amino acid ester in the field; in one embodiment, the chiral amino acid ester is selected from: L-phenylalanine ester, L-alanine ester, L-proline ester, L-leucine ester, L-valine ester, and L-phenylglycine ester, etc., and the selected ester can be alkyl ester or aryl ester; the chiral diol can be any acceptable chiral diol in the field; in one embodiment, the chiral diol is a diol containing 1,2-diol or 1,4-diol chiral structure; further, the chiral diol is selected from: chiral BINOL, chiral hydrogenated benzoin, (trans)-9,10-dihydroxy-9,10-dihydrophenanthrene, or (cis)-9,10-dihydroxy-9,10-dihydrophenanthrene, etc. Further, the second reagent is preferably a chiral amino alcohol for better separation effect.

In one embodiment,

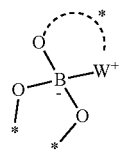

has the structure

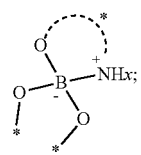

further,

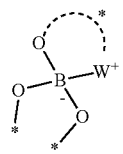

has the following structure:

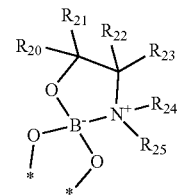

In which at least one of the carbon atom connected to $R_{20}$ and $R_{21}$ and the carbon atom connected to $R_{22}$ and $R_{23}$ is a chiral carbon;

$R_{20}$, $R_{21}$, $R_{22}$ and $R_{23}$ are independently selected from: H, substituted or unsubstituted $C_{1-6}$ alkyl, substituted or unsubstituted phenyl, substituted or unsubstituted naphthyl, or substituted or unsubstituted quinolyl;

$R_{24}$ and $R_{25}$ are independently selected from: H, substituted or unsubstituted $C_{1-6}$ alkyl, or substituted or unsubstituted phenyl;

$R_{23}$ and $R_{24}$ can connect with each other to form a ring structure;

$R_{23}$, $R_{24}$ and $R_{25}$ can connect with each other to form a bridged ring structure.

It is apprehensible that the "ring structure" in the present invention includes monocyclic ring (e.g., aromatic ring, heterocyclic ring), spiro ring, bridged ring, etc.

In one embodiment, $R_{20}$, $R_{21}$, $R_{22}$ and $R_{23}$ are independently selected from: H, phenyl, $C_{1-6}$ alkyl or alkoxy substituted quinolyl;

In one embodiment, $R_{24}$ and $R_{25}$ are independently selected from: H, $C_{1-6}$ alkyl, or phenyl;

In one embodiment, $R_{23}$ and $R_{24}$ can connect with each other to form a five-membered nitrogen-containing heterocyclic ring;

In one embodiment, $R_{23}$, $R_{24}$, and $R_{25}$ can connect with each other to form a structure

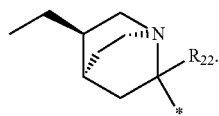

In one embodiment,

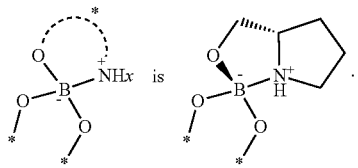

The present invention also provides the method for preparing the intermediates mentioned above, which includes the following steps:

Mix the compound to be separated (a mixture of compounds represented by formulas (IVa) and (IVa')), the first reagent, the second reagent and the aprotic solvent, and heat to reflux. After the reaction is completed, crystallize to obtain the intermediate represented by structural formula (IVa-1) or (IVa-2);

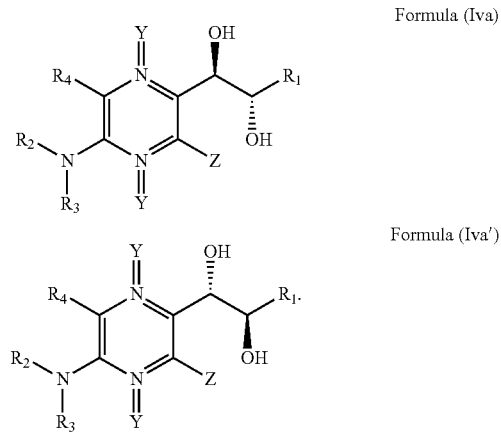

It is apprehensible that the reaction process of the reaction mentioned above should not be understood as limitations to the present invention. The reaction process can be as follows: First, the compound to be separated reacts with the first reagent to generate a mixture of compounds represented by structural formulas (IVa-3) and (IVa-4). Then, the mixture of compounds represented by structural formulas (IVa-3) and (IVa-4) reacts with the second reagent to obtain the intermediate represented by structural formula (IVa-1) or (IVa-2). Among them, the mixture of compounds represented by structural formulas (IVa-3) and (IVa-4) can be separated or unseparated, which should be understood as within the protection scope of the present invention.

Further, the reaction mentioned above includes the following steps:

S001: The compound to be separated is dissolved in an aprotic solvent;

Further, the aprotic solvent in step S001 is selected from one or more of the following solvents: tetrahydrofuran (THF), 2-methyltetrahydrofuran (2-MeTHF), acetonitrile (ACN), toluene, benzene, 1,4-dioxane (1,4-diox), and acetone, so as to increase the differences in solubility of the intermediates with different configurations, and precipitate the intermediate of desired configuration (formula (IVa-1)), further reduce the difficulty of separation, meanwhile, increase the yield and ee value of the product. Furthermore, the aprotic solvent is acetonitrile.

Further, add 1-100 mL of aprotic solvent per g of the compound to be separated. Furthermore, add 20-80 mL of aprotic solvent per g of the compound to be separated. Furthermore, add 30-60 mL of aprotic solvent per g of the compound to be separated.

S002: Add the first reagent and the second reagent, heat to reflux and react for a period of time predetermined; Through adding the first reagent and the second reagent, a new chiral center is introduced into the diastereomer, and thus a pair of diastereomers is obtained. Finally, separation can be achieved through crystallization. In addition, the compound represented by formula (IVa-1) obtained by this method is a critical intermediate for the preparation of L-erythro biopterin compound, and is precipitated as a solid in most conventional aprotic solvents, which can significantly reduce the difficulty of separation and increase the ee value of the product. For example, when boric acid ester and chiral amino alcohol are used, the specific reaction mechanism is as follows:

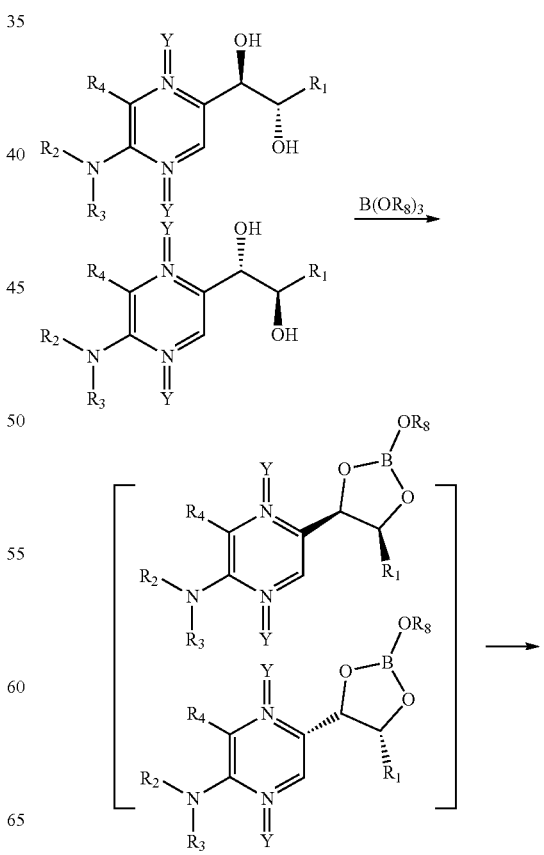

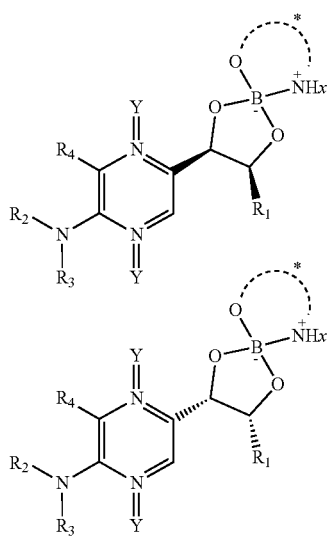

Further, the first reagent is boric acid ester or boric acid.

Further, the second reagent is chiral amino alcohol, chiral amino acid, chiral amino acid ester or chiral diol. Furthermore, the second reagent is chiral amino alcohol.

The first reagent and the second reagent are described as above, and will not be repeated here.

Furthermore, the boric acid ester is triisopropyl borate, the chiral amino alcohol is L-prolinol, and the solvent is acetonitrile.

Further, the molar ratio of the compound to be separated to the boric acid ester is less than or equal to 1. Further, the molar ratio of the first reagent to the second reagent is 1:(1.0-1.3). Further, the molar ratio of the first reagent to the second reagent is 1:1.

It is apprehensible that the order of addition of the reagents in step S002 is not specifically limited, and should not be understood as a limitation to the present invention, e.g., add the first reagent first, then add the second reagent, or add the first reagent and the second reagent simultaneously; in addition, the reaction time of step S002 is not specifically limited, which is adjusted according to the type of reagent used, and should not be understood as a limitation to the present invention;

Further, in step S002, add the first reagent first and react for 25-50 min, then add the second reagent and react for 8-24 h.

S003: Crystallize to obtain the intermediate represented by structural formula (IVa-1) or (IVa-2);

It is apprehensible that crystallization can be carried out by existing methods, and the temperature for solid-liquid separation in the crystallization process can be adjusted according to the solvent selected specifically, which should not be understood as a limitation to the present invention. In one embodiment, crystallization is carried out as follows: After the reaction is completed, cool the reaction liquid. A solid precipitate is formed. Separate the solid and liquid phases. The product of desired conformation is either the solid- or liquid-phase product.

The method for preparing the intermediate represented by structural formula (IVa-1) or (IVa-2) has the following advantages:

Since the solubility of the intermediate represented by structural formula (IVa-1) or (IVa-2) is different in aprotic solvents, only crystallization is required to make one of the intermediates represented by structural formulas (IVa-1) and (IVa-2) dissolve in the solvent and the other precipitate out. The products with different configurations can be separated by simple solid-liquid separation, which effectively reduces the difficulty of separation and is particularly suitable for industrial production;

The reaction conditions of the above-mentioned separation reagent set consisting of the first reagent and the second reagent are mild, and the requirements for the quality and purity of the substrate is loose. The ee value, dr value and purity of the product obtained after separation are extremely high. The separation can be realized even if the purity of the compound to be separated is 70%. Meanwhile, the purity of the obtained product can be increased to 99%. One-pot separation and purification is effectively realized;

The intermediate represented by structural formula (IVa-1) or (IVa-2) obtained by the above-mentioned method can be directly used for production in the next reaction step without separation. The ee and dr values can be further increased after the next synthesis step. Experiments showed that when a product with a ee value of 88% (IVa-1/IVa-2=94/6) is used for the next reaction step, the ee of the final product can also be increased to greater than 99.9%, with chiral purity comparable to that of natural chiral introduction;

The obtained intermediate represented by structural formula (IVa-1) or (IVa-2) is solid, structurally stable, and easy for quality control, production, storage and transportation.

The present invention also relates to a chiral separation reagent set comprising the first reagent and the second reagent. The first reagent is boric acid ester or boric acid, and the second reagent is chiral amino alcohol, chiral amino acid, chiral amino acid ester or chiral diol. The reagents are described as above, and will not be repeated here.

The present invention also relates to a chiral separation reagent set consisting of chiral amino alcohol and boric acid ester.

Further, the chiral separation reagent set mentioned above consists of boric acid ester and L-proline. Further, the chiral separation reagent set mentioned above consists of boric acid ester and L-phenylglycinol. Further, the chiral separation reagent set mentioned above consists of boric acid ester and (S)-(−)-α,α-diphenylprolinol. Further, the chiral separation reagent set mentioned above consists of boric acid ester and quinine. Further, the chiral separation reagent set mentioned above consists of boric acid ester and cinchoni.

The present invention also relates to the application of the chiral separation reagent set mentioned above in the preparation of L-erythro biopterin compound.

In one embodiment of the present invention, the L-erythro biopterin compound is mainly prepared using the compound represented by structural formula (II) or (III) through dihydroxylation. Among them, the L-erythro biopterin compound is represented by structural formula (I):

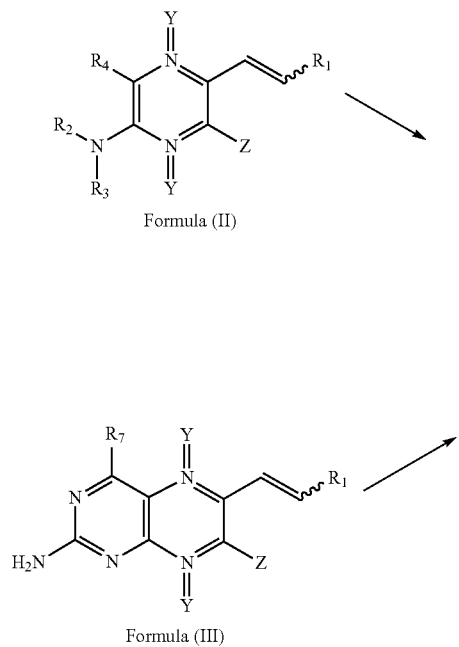

Formula (II)

Formula (I)

Formula (III)

In which, Y is O or absent. In one embodiment, Y is absent.

Z is a hydrogen atom or a leaving group; among them, the leaving group includes but is not limited to: halogen (e.g., Cl, Br, I), $OSO_nR_9$, $OCOR_{10}$ or $OPO_2R_{11}$. $R_9$, $R_{10}$, or $R_{11}$ is independently selected from: —$CF_3$, alkyl, phenyl, or alkyl-substituted phenyl (e.g., tolyl). n is 0, 1 or 2, and the silicyl group can be a silyl group, etc.

$R_1$ is a substituted or unsubstituted alkyl, a substituted or unsubstituted cycloalkyl, a substituted or unsubstituted heterocycloalkyl, a substituted or unsubstituted aryl, or a substituted or unsubstituted heteroaryl; $R_2$ and $R_3$ are independently a hydrogen atom, or an amino-protecting group; among them, the amino-protecting group includes but is not limited to: -Boc, -Cbz, —Ac, -Ts, -Ms, -Bz, -Bn, -PMB, or schiff base.

$R_2$ and $R_3$ together with the nitrogen atom connected to $R_2$ and $R_3$ can form a cyclic lactim group, e.g., glutarimide, and succinimide. It is apprehensible that $R_2$ and $R_3$ together with the nitrogen atom to which they are connected do not necessarily form a cyclic lactim group, which is selected as necessary.

$R_4$ is —$COOR_5$, —$CONR_6$, or —CN. In one embodiment, $R_4$ is —CN.

$R_5$ and $R_6$ are independently a hydrogen atom, a substituted or unsubstituted alkyl, a substituted or unsubstituted cycloalkyl, a substituted or unsubstituted heterocycloalkyl, a substituted or unsubstituted aryl, or a substituted or unsubstituted heteroaryl.

In the above-mentioned preparation method of L-erythro biopterin compound, the alkene compound represented by formula (II) or (III) is innovatively used as the raw material, and the dihydroxy of desired configuration is constructed through a dihydroxylation reaction, which effectively avoids the use of intermediates such as 5-deoxy-L-arabinose (D), and thus avoids the use of ethanethiol with a strong foul smell, and effectively reduces environmental pollution, and is environment-friendly. In addition, the reaction conditions for dihydroxylation of alkenes are relatively mild, the operation is convenient, the yield is relatively high, and the raw material represented by structural formula (II) or (III) is readily available, which can greatly shorten the reaction route, further improve the efficiency, reduce the production cost, and is suitable for industrial production.

It is apprehensible that, while performing the reactions described in the present invention, common reactions in the field (e.g., oxidation reaction, reduction reaction) are used to convert raw materials into the desired compound (e.g., compound represented by formula (II) or (III)), regardless of whether the desired compound (e.g., compound represented by formula (II) or (III)) is separated or directly used in subsequent reaction, it should be understood as within the protection scope of the present invention. For example: For the cyclization reaction of

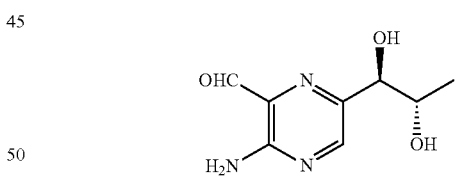

($R_4$ is —CHO), an oxidizing agent is added before or while the cyclization reaction is undergoing (in the one-pot reaction, oxidation and cyclization occurs simultaneously) to convert the aldehyde group to carboxylic acid or carboxylic ester, followed by the cyclization reaction. It should be understood that it is equivalent to the technical scheme in which $R_4$ is carboxylic acid or carboxylic ester, and regardless of whether or not performing separation to the compound containing carboxylic acid or carboxylic ester, it should be understood as within the protection scope of the present invention.

In one embodiment, $R_1$ is selected from $C_{1-6}$ alkyl, 3-8 membered cycloalkyl, 3-10 membered aryl, 3-10 membered heteroaryl, TMS, TBS, or —$CH_2X$; X is a leaving group. In one embodiment, $R_1$ is selected from $C_{1-6}$ alkyl, cyclopropyl, phenyl, pyridyl, TMS, TBS, or —CH$_2$X, and X is a leaving group. In one embodiment, R$_1$ is methyl.

R$_5$ and R$_6$ are independently a hydrogen atom, or a substituted or unsubstituted C$_{1-20}$ alkyl. In which, C$_{1-20}$ alkyl can be further substituted by C$_{1-6}$ alkyl, 3-8 membered cycloalkyl, 3-10 membered aryl, 3-10 membered heteroaryl, hydroxyl, halogen, amino, cyano, or C$_{1-4}$ alkoxy.

R$_7$ is —OH or —NH$_2$. When R$_7$ is —NH$_2$, a compound with R$_7$ as —OH can be obtained by hydrolysis under alkaline conditions.

It is apprehensible that the term "dihydroxylation" should be understood as the ordinary meaning in the field, referring to a reaction at the double bond site of an alkene (e.g.,

in formula (II) or (III)) to generate an o-dihydroxy compound. The dihydroxylation methods include, but are not limited to, Sharpless asymmetric dihydroxylation reaction, basic KMnO4 dihydroxylation reaction, Fe-catalyzed dihydroxylation or asymmetric epoxidation followed by hydrolysis and ring opening. The Sharpless asymmetric dihydroxylation is preferable. The inventor has found in the research process that if the compound represented by formula (II) or formula (III) is used as the reactant, and the Sharpless asymmetric dihydroxylation reaction is employed, the product of desired configuration can be obtained in a higher yield, the difficulty of separation is greatly reduced and the efficiency of production is improved.

It should be noted that the alkene group

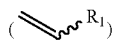

in formula (II) or (III) can be a cis or trans structure.

It is apprehensible that in the reaction, the compound represented by formula (II) or (III) can be a pure substance, i.e., a compound represented by formula (II) or (III) containing only the cis structure, or a compound represented by formula (II) or (III) containing only the trans structure, or a mixture, i.e., a mixture of the cis and trans structures, which will not be specifically limited herein (preferably a compound represented by the cis structural formula (II)). The mixture can be separated by chiral separation after reaction. The chiral separation method is not specifically limited, and can be an existing separation method. The compound represented by formula (II) undergoes dihydroxylation reaction, followed by cyclization to obtain the L-erythro biopterin compound represented by formula (I). Among them, the cyclization methods can be existing methods, such as those in *Journal of Organic Chemistry* 1987, 52(18), 3997-4000 and *Journal of Organic Chemistry* 1988, 53 (1), 35-38.

1. Preparation of L-Erythro Biopterin Compound from Compound Represented by Formula (II)

1.1 Preparation of L-Erythro Biopterin Compound from Cis-Alkene

When the alkene in the compound represented by formula (II) is of a cis structure, the steps for preparing the L-erythro biopterin compound represented by formula (I) from the compound represented by formula (II) are as follows:

S111: The compound represented by formula (IIa) is subjected to a dihydroxylation reaction to obtain the compound represented by formula (IVa).

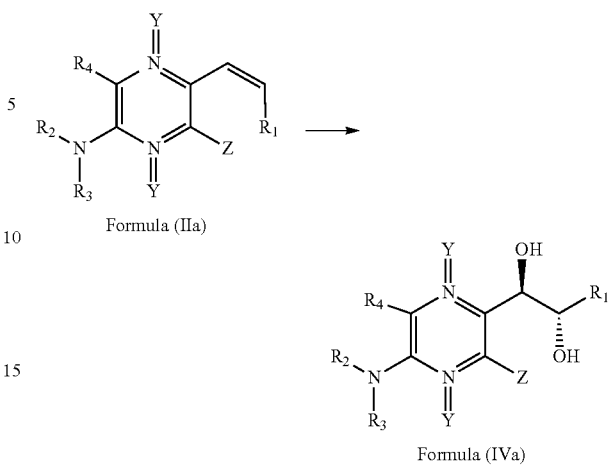

Formula (IIa)

Formula (IVa)

Among them, the dihydroxylation reaction in step S111 includes but is not limited to: Sharpless asymmetric dihydroxylation reaction, basic KMnO$_4$ dihydroxylation reaction, Fe-catalyzed dihydroxylation reaction or asymmetric epoxidation followed by hydrolysis and ring opening. Sharpless asymmetric dihydroxylation reaction is preferred.

(1) When the Sharpless asymmetric dihydroxylation reaction is used for the reaction, step S111 can include the following steps: Mix the compound represented by formula (IIa), the oxidizing agent, the dihydroxylation reagent, the base and the ligand for reaction. After the reaction is completed, quench the reaction and separate. The reaction is preferably carried out at 0-25° C. After the reaction is completed, the reaction can be quenched with sodium sulfite. After quenching, the insoluble matter is filtered, the organic phase is collected, and chiral separation is performed to the organic phase to obtain a single chiral compound represented by formula (IVa) (R,S).

Further, the dihydroxylation reagent is selected from one or more of the following reagents: OsO$_4$, K$_2$OsO$_4$, OsO$_4$ hydrate and K$_2$OsO$_4$ hydrate; the oxidizing agent is selected from K$_3$[Fe(CN)$_6$] or NMO and both; the base is selected from one or more of the following reagents: potassium carbonate, sodium carbonate, cesium carbonate, potassium bicarbonate, sodium bicarbonate, NaOH, KOH, LiOH, NH$_4$OH, t-BuONa, t-BuOK, t-BuOLi, triethylamine, diisopropylethylamine, DBU, pyridine and p-dimethylaminopyridine; the ligand is selected from one or more of the following reagents: (DHQ)$_2$PHAL, (DHQD)$_2$PHAL, DHQ-IND and DHQD-IND; the solvent can be one or more of acetone, methanol, ethanol, 1,4-dioxane, tert-butanol, and THF.

In addition, in the above-mentioned step S111, an osmate ester hydrolyzing agent can also be added, and the osmate ester hydrolyzing agent includes but is not limited to methanesulfonamide.

In addition, it is preferred that the amount ratio of the compound represented by formula (IIa) to the solvent is 1 g:(10-100 mL); the molar ratio of the compound represented by formula (IIa) to the oxidizing agent is 1:(0.1%-20%); the molar ratio of the compound represented by formula (IIa) to the base is 1:(1-10); the molar ratio of the compound represented by formula (IIa) to methanesulfonamide is 1:(1-10).

(2) When the basic KMnO$_4$ dihydroxylation reaction is used for the reaction, step S111 can include the following steps: Mix the compound represented by formula (IIa), the dihydroxylation reagent, the base and the solvent for reaction. After the reaction is completed, chiral separation is performed.

Further, the dihydroxylation reagent is KMnO$_4$; the base can be one or more of potassium carbonate, sodium carbonate, cesium carbonate, potassium bicarbonate, sodium bicarbonate, NaOH, KOH, LiOH, NH$_4$OH, t-BuONa, t-BuOK, t-BuOLi, cesium carbonate, triethylamine, diisopropylethylamine, DBU, pyridine and p-dimethylaminopyridine; the solvent is one or more of acetone, methanol, ethanol, 1,4-dioxane, tert-butanol and THF.

(3) When the Fe-catalyzed dihydroxylation reaction is used for the reaction, step S111 can include the following steps: Mix the compound represented by formula (IIa), the dihydroxylation reagent, the catalyst, and the solvent for reaction. After the reaction is completed, chiral separation is performed.

Further, the dihydroxylation reagent is hydrogen peroxide; the catalyst is one or more of Fe(ClO$_4$)$_2$, Fe(OTf)$_2$, FeCl$_2$, and FeBr$_2$; the solvent can be one or more of acetone, methanol, ethanol, 1,4-dioxane, tert-butanol and THF.

(4) When the epoxidation reaction is used for the reaction, step S111 can include the following steps: The compound represented by formula (II) reacts with an epoxidation reagent to obtain an epoxidized intermediate, then the ring is opened with acid or base, and perform chiral separation to obtain the desired dihydroxylation product.

The preferred epoxidation reagent is one or more of m-CPBA, DMDO, and salen-Mn(III)/NaOCl; the solvent can be one or more of methylene chloride, tetrahydrofuran, 1,4-dioxane, and tert-butanol. The acid used for ring opening can be dilute hydrochloric acid, dilute sulfuric acid, dilute phosphoric acid, etc., and the base used can be KHCO$_3$, K$_2$CO$_3$, KOH, etc.

It is apprehensible that "chiral separation" after the above-mentioned dihydroxylation reaction can be performed by using a chiral column or chemical separation. The chiral separation reagent set is preferred for the separation of the compound to be separated. The chiral separation reagent set includes the first reagent and the second reagent. The first reagent is boric acid ester or boric acid; the second reagent is chiral amino alcohol, chiral amino acid, chiral amino acid ester or chiral diol. The reagents are described as above and will not be repeated here;

Further, step S111 includes the following steps:

S1111: The compound represented by formula (IIa) is subjected to dihydroxylation reaction to obtain the compound to be separated, which is composed of the compounds represented by formula (IVa) and formula (IVa');

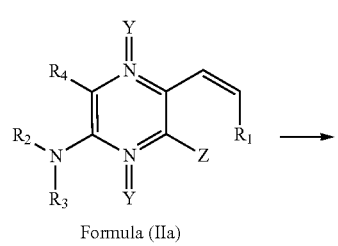

Formula (IIa)

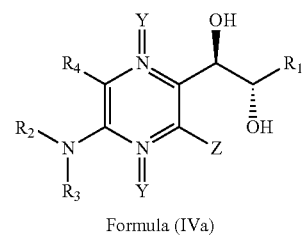

Formula (IVa)

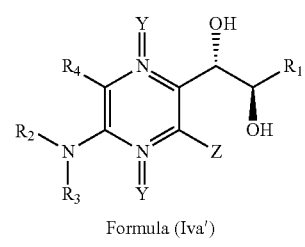

Formula (Iva')

Further, the dihydroxylation reaction is described as above and will not be repeated here.

S1112: The compounds to be separated are separated using a chiral separation reagent set to obtain the compound represented by formula (IVa-1);

Among them, the chiral separation reagent set in Step S1112 includes the first reagent and the second reagent. The first reagent is boric acid ester or boric acid, and the second reagent is chiral amino alcohol, chiral amino acid, chiral amino acid ester or chiral diol. Specifically, the separation method in Step S1112 refers to the preparation method for the intermediate with the structure represented by the above-mentioned formula (IVa-1) or formula (IVa-2), which will not be repeated here.

S112: Through a cyclization reaction with

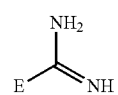

and/or the salt of

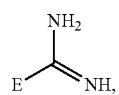

the L-erythro biopterin compound represented by formula (I) is obtained;

Specifically, L-erythro biopterin compound represented by formula (I) can be prepared according to the following steps S112a and S112b;

S112a: The compound represented by formula (IVa) undergoes a cyclization reaction with

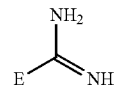

and/or the salt of

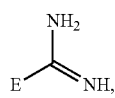

by which the L-erythro biopterin compound represented by formula (I) is obtained;

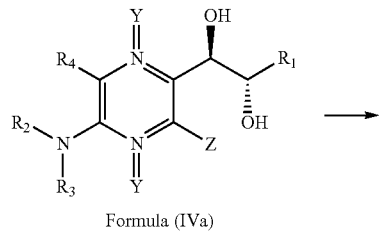

Formula (IVa)

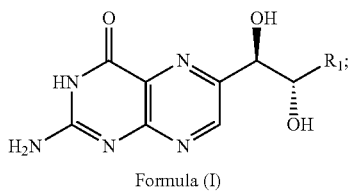

Formula (I)

S112b: The compound represented by formula (IVa-1) undergoes a cyclization reaction with

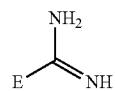

and/or the salt of

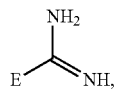

by which the L-erythro biopterin compound represented by formula (I) is obtained;

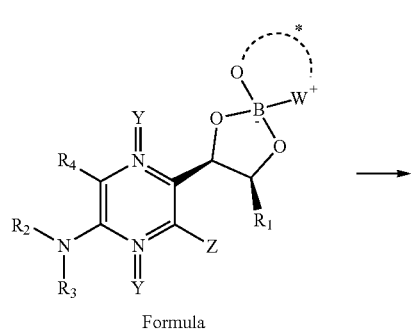

Formula

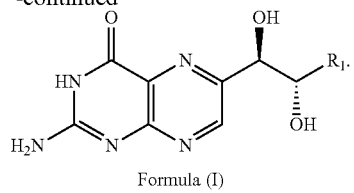

Formula (I)

E is halogen, $C_{1-4}$ alkoxy, $C_{1-4}$ alkylthio or —$NH_2$. Further, E is methoxy, chlorine, methylthio or —$NH_2$;

Since the compound represented by formula (IVa-1) can rapidly release the compound represented by formula (IVa) in the protic solvent, while the solvent used in the cyclization reaction with

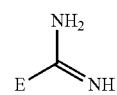

and/or the salt of

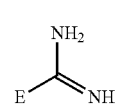

is a protic solvent, so the compound represented by formula (IVa-1) can be directly put into the subsequent reaction without dissociation, which can effectively reduce the difficulty of operation, save costs, further improve the ee value of the product with desired configuration through the cyclization reaction, and is of great application prospect.

It should be noted that the compound represented by formula (IVa-1) is directly used in step S112b for subsequent reactions, but it should not be understood as a limitation to the present invention. Similarly, the compound represented by formula (IVa-1) can be treated with a protonic solvent first. After obtaining the compound represented by formula (IVa), allow the compound represented by formula (IVa) for subsequent reactions, which is the same as step S112a.

The salt of

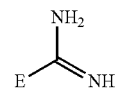

in step S112 refers to a salt that contains

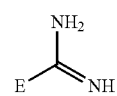

and can be an acceptable salt in this field, such as a hydrochloride. It is apprehensible that the and/or the salt of

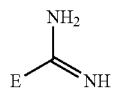

can contain acceptable protecting groups in this field, and it should be understood that all of them are within the protection scope of the present invention.

Step S112a is essentially the same as S112b except that the compound represented by formula (IVa) is used instead of the compound represented by formula (IVa-1) in step S112b. Now, it is further explained by taking step S112b as an example;

Further, step S112b includes the following steps:

S1121: Cyclization step: Mix the compound represented by formula (IVa-1),

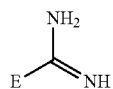

and/or the salt of

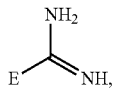

base and solvent, and heat to 50-100° C. for reaction. After the reaction is completed, cool. A solid substance is precipitated. Filter and obtain the solid substance (i.e., the compound represented by formula (I-1)).

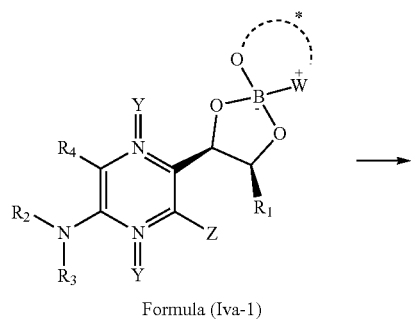

Formula (Iva-1)

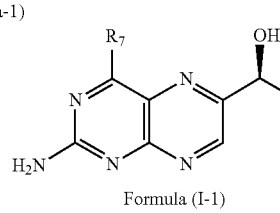

Formula (I-1)

The definitions of Y, Z, $R_1$, $R_2$, $R_3$ and $R_4$ are described as above and will not be repeated here. $R_7$ is —OH or —NH$_2$.

Furthermore, the above-mentioned cyclization step includes the following steps: Add Na to MeOH, stir until the reaction is completed. Then add

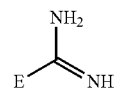

and/or the salt of

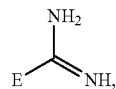

and stir at room temperature for a predetermined time (preferably 3-10 min) under the protection of N$_2$. Then, filter the insoluble matter in the system, add the compound represented by formula (IVa-1), and heat to reflux. After the reaction is completed, cool to room temperature and stir for 40 min-80 min. Filter to obtain the solid substance precipitated.

In the above-mentioned cyclization step, the solvent is a protic solvent, which is preferably an alcohol solvent, including but not limited to one or more of methanol, ethanol and isopropanol. The base can be one or more of sodium ethoxide, sodium methoxide, t-BuONa, t-BuOK, and t-BuOLi; it is preferably a strong base, such as sodium methoxide. The molar ratio of the compound represented by formula (IVa-1) to

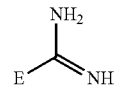

and/or the salt of

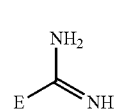

is 1:(1-3); the molar ratio of the compound represented by formula (IVa-1) to the base is 1:(2-5); the ratio of the compound represented by formula (IVa-1) to the solvent is 1 g:(5-100 mL).

In the above-mentioned cyclization step, $R_4$ is used as the raw material of COOR$_5$, —CONR$_6$ or —CN, and the

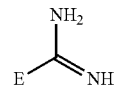

and/or the salt of

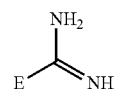

is used innovatively for the cyclization reaction to form the desired ring, which is initially applied to the synthesis of biopterin compounds. Compared with the traditional method, it has obvious advantages: High atom availability, high conversion rate, and clean reaction; by-products are soluble in the reaction solvent, while the product is insoluble and easy to purify. This process only needs to filter the product and simply wash, then high-purity product (98%-99%) can be obtained. The cost of

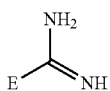

and/or the salt of

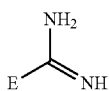

is relatively low, which can further reduce the production cost. However,

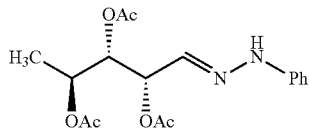

is used as a raw material in the traditional cyclization process, and it is necessary to accurately adjust the pH value of the reaction system and accurately control the temperature to hydrolyze the acetyl group, so as to prevent the breaking of side chain at position 6 during hydrolysis. It is difficult to operate and not suitable for industrial production.

S1122: Hydrolysis step: Add the solid substance (i.e., the compound represented by formula (I-1)) obtained in the cyclization step to an alkaline solution for reaction. After the reaction is completed, add acid, and adjust the pH to 5-6. Crystals are precipitated. Filter and dry to obtain the L-erythro biopterin compound represented by formula (I).

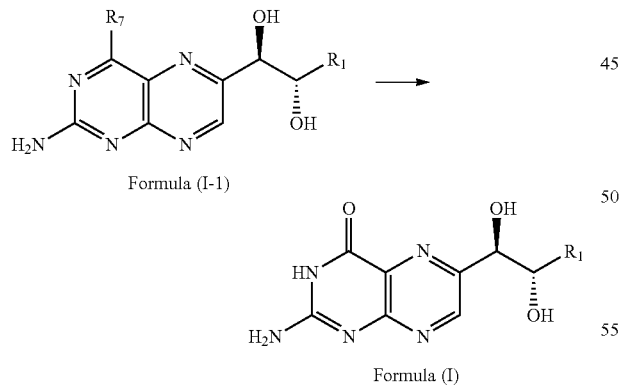

Formula (I-1)

Formula (I)

The definition of $R_1$ is described as above and will not be repeated here. $R_7$ is —OH or —NH$_2$.

Furthermore, the step of hydrolysis includes the following steps: Suspend the compound represented by formula (I-1) in an alkaline solution, heat to 50° C.-100° C., and stir for 2 h-5 h; cool to room temperature, and then add acid to adjust the pH to 5-6. There are crystals precipitated. Filter and dry to obtain the L-erythro biopterin compound represented by formula (I).

Among them, the alkaline solution can be an inorganic alkaline solution, such as sodium hydroxide solution and potassium hydroxide solution, and a sodium hydroxide solution with a mass percentage of 5%-40% is preferred. Preferably, the molar ratio of the compound represented by formula (I-1) to the base is 1:(5-20), more preferably 1:(5-10). The acid can be an organic acid or an inorganic acid, such as formic acid, hydrochloric acid, sulfuric acid, and hydrobromic acid, and formic acid is preferred.

It is apprehensible that when $R_4$ is —COOR$_5$ or —CONR$_6$, the hydrolysis step can be omitted.

It is apprehensible that when the compound represented by formula (IVa-1) is processed to obtain the compound represented by formula (IVa), the steps for the compound represented by formula (IVa) reacting with $$\underset{E}{\overset{NH_2}{\diagdown}}{\diagup}NH$$

and/or the salt of $$\underset{E}{\overset{NH_2}{\diagdown}}{\diagup}NH$$

are basically the same as those in the method mentioned above. It is only necessary to replace the compound represented by formula (IVa) with the compound represented by formula (IVa-1), which will not be repeated here.

1.2 Preparation of L-Erythro Biopterin Compound from Trans-Alkene

When the alkene in the compound represented by formula (II) is of a trans structure, the steps for preparing the compound represented by formula (I) from the compound represented by formula (II) are as follows:

S121: The compound represented by formula (IIb) is subjected to a dihydroxylation reaction to obtain the compound represented by formula (IVb-1) and/or formula (IVb-2).

Formula (IIb)

Formula (Ivb-1)

Formula (Ivb-2)

The dihydroxylation reaction in step S121 is the same as that in step S111, and will not be repeated here.

S122: The compound represented by formula (IVb-1) and/or the formula (IVb-2) is subjected to an acetylation reaction to obtain the compound represented by formula (VIIb-1) and/or formula (VIIb-2).

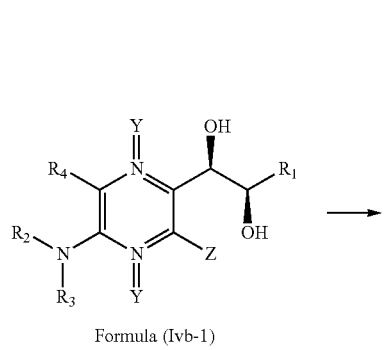

Formula (Ivb-1)

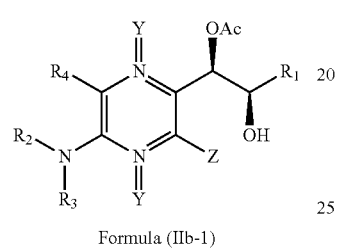

Formula (IIb-1)

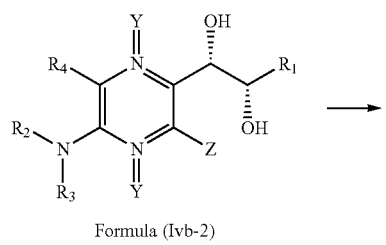

Formula (Ivb-2)

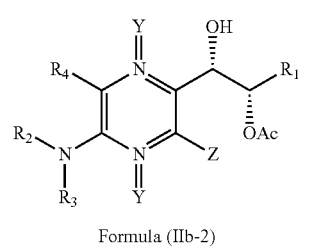

Formula (IIb-2)

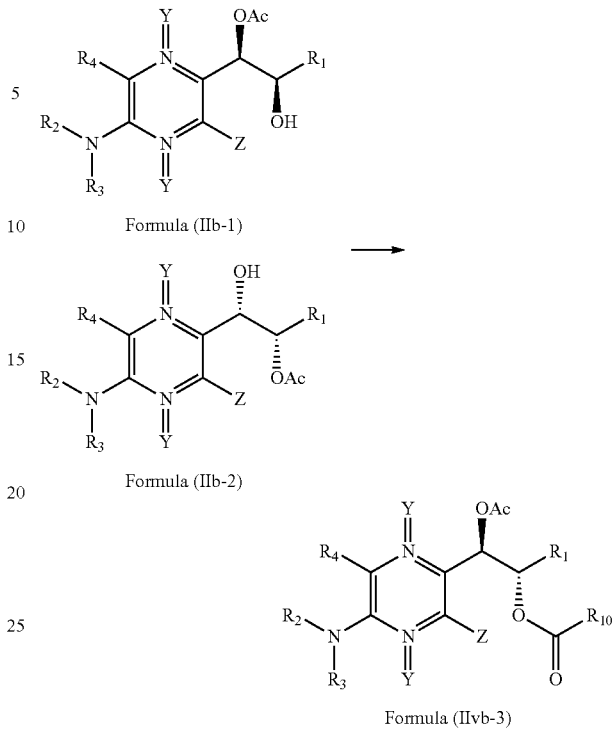

Formula (IIb-1)

Formula (IIb-2)

Formula (IIvb-3)

Formula (IIvb-4)

Among them, the acetylation reaction in step S122 can include the following steps:

Dissolve the compound represented by formula (IVb-1) and/or the compound represented by formula (IVb-2), acetylation reagent and p-toluenesulfonamide (PTSA) in the solvent, stir for 20 min-50 min, then add water and continue stirring. After the reaction is completed, the compound represented by formula (VIIb-1) and/or formula (VIIb-2) can be obtained by separation. Among them, the acetylation reagent includes but is not limited to one or more of acetic anhydride, trimethyl orthoacetate, and acetyl chloride; the solvent can be one or more of acetonitrile, THF, dioxane, DCM, MTBE, etc.

S123: The compound represented by formula (VIIb-1) and/or formula (VIIb-2) is subjected to Mitsunobu reaction to obtain the compound represented by formula (VIIb-3) and/or formula (VIIb-4).

Specifically, it can include the following steps:

Dissolve the compound represented by formula (VIIb-1) and/or formula (VIIb-2), nucleophile

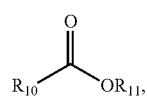

PPh$_3$ or Bu$_3$P, diisopropyl azodicarboxylate (DIAD) or diacetate azodicarboxylate (DEAD) in a solvent for reaction. After the reaction is completed, separate to obtain the desired product. Specific reagent combinations include but are not limited to: DEAD/PPh$_3$, DIAD/PPh$_3$, DEAD/n-Bu$_3$P, DIAD/n-Bu$_3$P, etc.

In which R$_{10}$ is substituted or unsubstituted alkyl, substituted or unsubstituted cycloalkyl, substituted or unsubstituted heterocycloalkyl, substituted or unsubstituted aryl, or substituted or unsubstituted heteroaryl; preferably R$_{10}$ is substituted or unsubstituted aryl. When aryl is further substituted, the substituent is selected from C$_{1-6}$ alkyl or C$_{1-6}$ alkoxy. More preferably, R$_{10}$ is

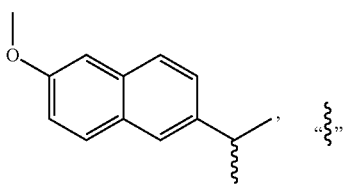

represents the connection site.

$R_{11}$ is H, substituted or unsubstituted alkyl, substituted or unsubstituted cycloalkyl, substituted or unsubstituted heterocycloalkyl, substituted or unsubstituted aryl, or substituted or unsubstituted heteroaryl; preferably $R_{11}$ is H or $C_{1-6}$ alkyl.

In one embodiment,

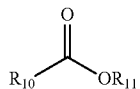

is

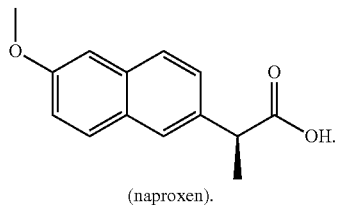 [SMILES: COc1ccc2cc([C@H](C)C(=O)O)ccc2c1]

(naproxen).

S124: The compound represented by formula (VIIb-3) and/or formula (VIIb-4) undergoes a cyclization reaction with

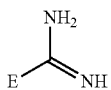

and/or the salt of

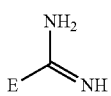

(preferably guanidine salt), followed by hydrolysis to obtain the L-erythro biopterin compound represented by formula (I).

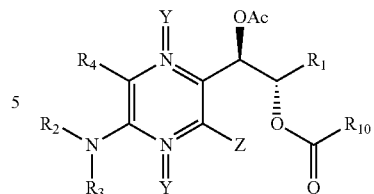

Formula (IIvb-3)

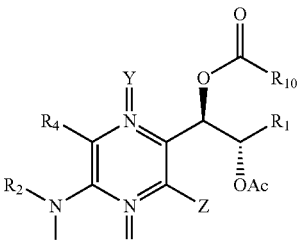

Formula (IIvb-4)

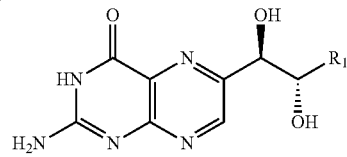

Formula (I)

Step S124 is the same as step S112, and will not be repeated here. The definitions of Y, Z, $R_1$, $R_2$, $R_3$, $R_4$ and $R_{10}$ are described as above, and will not be repeated here. E is halogen, $C_{1-4}$ alkoxy, $C_{1-4}$ alkylthio or —$NH_2$. Further, E is methoxy, chlorine, methylthio or —$NH_2$;

When the alkene in the compound represented by formula (II) is of a cis structure, through a dihydroxylation reaction and a cyclization reaction, the product of desired configuration can be obtained in two steps with high yield, which can greatly shorten the reaction route, improve the production efficiency, and reduce the production cost. When the alkene in the compound represented by formula (II) is of a trans structure, first, the dihydroxylation reaction is used to construct dihydroxy and form two chiral centers, and then a highly selective mono-acetylation reaction of vicinal diols is used innovatively to achieve acetylation of one of the hydroxyl groups, and the Mitsunobu reaction is used to achieve the chiral inversion of the other hydroxyl group, so as to obtain the intermediate with desired configuration, and then cyclize to obtain the desired product, which greatly expand the range for selecting raw materials, and then relative inexpensive raw materials can be selected. In addition, the acetylation reaction, Mitsunobu reaction and other steps are of high yields, and the by-product of monoacetylation and the by-product that did not flip-over in the Mitsunobu reaction can also be recovered to be raw materials by simple hydrolysis and be reused, which ensures the economy of the entire route and meets the requirements of industrial production.

2. Preparation of L-Erythro Biopterin Compound from Compound Represented by Formula (III)

It is apprehensible that the compound represented by formula (III) can be a commercially available raw material, or can be prepared from the compound represented by formula (II) through a cyclization reaction. For example, the compound represented by formula (II) can be used for cyclization with and/or the salt of

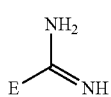

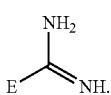

2.1 Preparation of L-Erythro Biopterin Compound from Cis-Alkene

Further, when the alkene in the compound represented by formula (III) is of a cis structure, the steps for preparing the L-erythro biopterin compound represented by formula (I) from the compound represented by formula (III) are as follows:

S211: The compound represented by formula (III) is subjected to a dihydroxylation reaction to obtain the compound represented by formula (I-1).

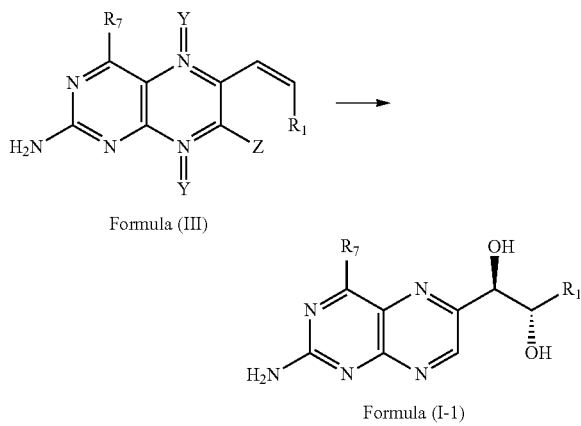

The reaction reagents and reaction conditions of the dihydroxylation reaction in step S211 are as described in step S111, and will not be repeated here.

It is apprehensible that the chiral separation reagent set mentioned above can also be used for separation in step S211. The separation method and the chiral separation reagent set are described as above. It is only necessary to replace the compound to be separated in step S111 with the compound to be separated (mixture of

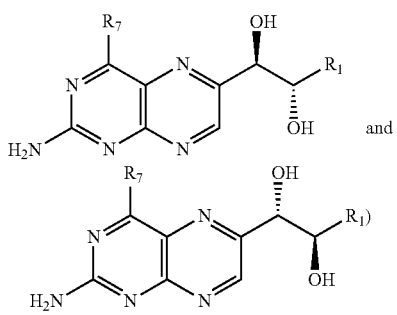

represented by the formula (III) and generated after the substrate dihydroxylation reaction. It is not repeated here, and it should be understood that all of them are within the protection scope of the present invention.

S212: The compound represented by formula (I-1) is hydrolyzed under alkaline conditions (such as condition of sodium hydroxide) to obtain the L-erythro biopterin compound represented by formula (I).

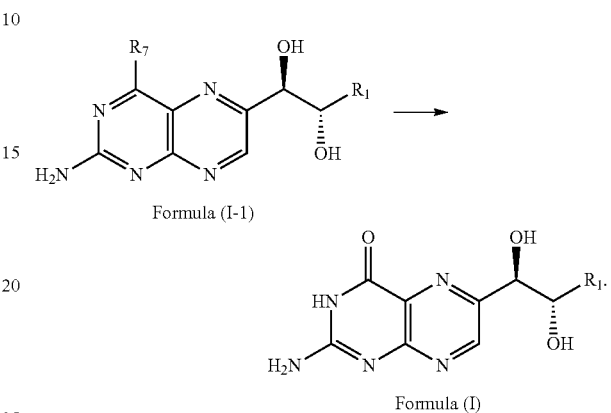

Step S212 is the same as step S1122, and will not be repeated here.

2.2 Preparation of L-Erythro Biopterin Compound from Trans-Alkene

When the alkene in the compound represented by formula (III) is of a trans structure, first, the compound represented by formula (III) undergoes a dihydroxylation reaction to form dihydroxy, followed by an acetylation reaction, and then by the Mitsunobu reaction to obtain the product of desired configuration. The specific method and steps are the same as those in S121 to S124, and will not be repeated here.

When the alkene in the compound represented by formula (III) is of a cis structure, through a dihydroxylation reaction, the product of the desired configuration can be obtained in a high yield, which can greatly shorten the reaction route, improve the production efficiency, and reduce the production cost. When the alkene in the compound represented by formula (III) is of a trans structure, first, the dihydroxylation reaction is used to construct dihydroxy and form two chiral centers, and then a highly selective mono-acetylation reaction of vicinal diols is used innovatively to achieve acetylation of one of the hydroxyl groups, and the Mitsunobu reaction is used to achieve the chiral inversion of the other hydroxyl group, and then hydrolyze to obtain the desired product, which greatly expand the range for selecting raw materials, and then relative inexpensive raw materials can be selected. In addition, the acetylation reaction, Mitsunobu reaction and other steps are of high yields, and the by-product of monoacetylation and the by-product that did not flip-over in the Mitsunobu reaction can also be recovered to be raw materials by simple hydrolysis and be reused, which ensures the economy of the entire route and meets the requirements of industrial production.

3. Preparation of Compounds Represented by Formula (II) and Formula (III)

It should be noted that the compound represented by formula (II) or formula (III) can be synthesized by existing methods, such as Heck reaction (see *JJ. Chem. Soc., Chem. Commun.* 1983, 15, 793-794), Grignard reaction (See *Chemistry Letters* 2014, 43(6), 922-924), alkyl lithium debromination and propenyl bromide reaction (see *Chemistry-An*

Asian Journal 2012, 7(5), 1061-1068), Stille reaction (see J. Org. Chem. 1990, 55, 3019), and Negishi coupling (see J. Chem. Soc., Chem. Commun. 1977, 683-684). It can also be a commercially available raw material, and it should be understood that all of the situations are within the protection scope of the present invention.

However, the applicant found in the research that: the cis-trans selection and region selection of the compound represented by formula (II) or formula (III) prepared by the Heck reaction are poor; in the Grignard reaction, although the cis-trans can be controlled, it needs to prepare a less stable aryl group magnesium bromide, which is difficult to industrialize; in the alkyl lithium debromination and propenyl bromide reaction, the conditions are harsh, and the conversion rate is low; in the Stille reaction, alkenyl tin reagent is used to couple with the substrate, which needs to synthesize highly toxic organotin, and thus is not suitable for industrial production; in Negishi coupling, it needs to prepare unstable and flammable organozinc reagents, and the post-processing is complicated, which is not suitable for industrial production. It is preferably to synthesize according to the following method, so as to further improve the production efficiency and reduce the production cost.

3.1 Synthesis of Compound Represented by Formula (I)

3.1.1 Synthesis of the Compound Represented by the Cis Structural Formula (I)

When the alkene in the compound represented by formula (II) is a compound represented by the cis structural formula (IIa), the compound represented by formula (IIa) is obtained by catalytic hydrogenation of the compound represented by formula (V):

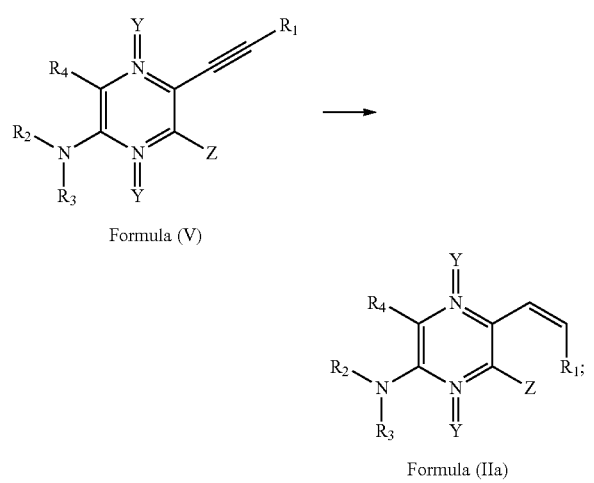

Specifically, it can include the following steps:

Mix the compound represented by formula (V), the catalyst and the solvent, and allow to react under a hydrogen atmosphere. After the reaction is completed, filter and concentrate to obtain the compound represented by the cis structural formula (IIa).

Among them, the catalyst can be selected from one or more of the following reagents: Lindlar catalyst, palladium/carbon, Raney nickel, platinum black and platinum dioxide. The solvent can be selected from one or more of the following reagents: tetrahydrofuran, 2-methyltetrahydrofuran, ethyl ether, methyl tert-butyl ether, methyl cyclopentyl ether, methanol, ethanol, isopropanol, acetonitrile and toluene.

Preferably, the ratio of amounts used of the compound represented by formula (V) to the solvent is 1 g:(1-100 mL), more preferably 1 g:(5-60 mL). The weight ratio of the compound represented by formula (V) to the catalyst is 1:(0.005-0.2), more preferably 1:(0.01-0.1). The pressure of hydrogen introduced is 0.1-10 MPa, more preferably 0.1-5 MPa; the reaction temperature is preferably 0-50° C.

Among them, the compound represented by formula (V) can be a commercially available raw material, or it can be synthesized by an existing method, and it is preferably synthesized by the following method:

S311: The compound represented by formula (V) is obtained by the Sonogashira reaction of the compound represented by formula (VI):

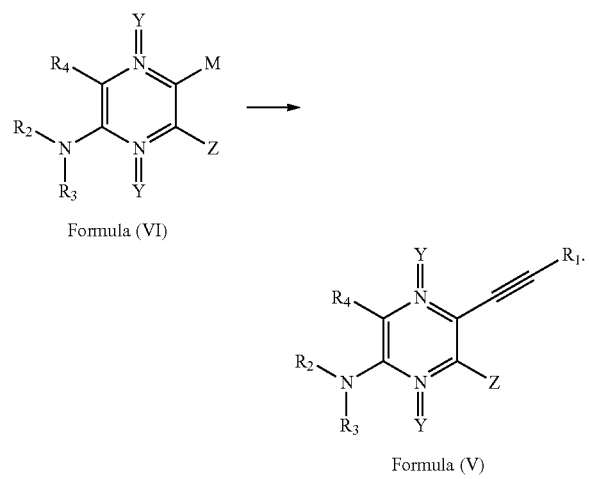

In which M is H or a leaving group, preferably M is a halogen, sulfonic ester, carboxylic ester or phosphoester. The leaving group includes but is not limited to: halogen (for example: Cl, Br, I), $OSO_nR_9$, $OCOR_{10}$ or $OPO_2R_{11}$. $R_9$, $R_{10}$, or $R_{11}$ is independently selected from: $—CF_3$, alkyl, phenyl, or alkyl-substituted phenyl (such as tolyl); n is 0, 1 or 2, and the silicyl group can be a silyl group, etc. Among them, the sulfonic ester can be: methyl benzenesulfonic ester, methanesulfonic ester, trifluoromethanesulfonic ester, etc. More preferably, M is bromine.

When using the above-mentioned reaction to prepare the compound represented by formula (V), the compound represented by formula (VI) which is widely available in the market can be used as the raw material, which significantly reduces the production cost, the reaction yield is high (>95%), the reaction conditions at room temperature is mild, and the product can be obtained by conventional recrystallization.

Specifically, it can include the following steps:

S3111: Mix the compound represented by formula (VI), catalyst, ligand and solvent;

S3112: Add alkali and

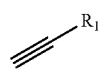

for reaction. After the reaction is completed, quench the reaction and separate to obtain the compound represented by formula (V).

In the above-mentioned step S3111, it is preferable to dissolve at a temperature of 0-35° C., the catalyst is preferably a combination of copper catalyst and palladium catalyst, and the ligand is a phosphorus ligand.

Among them, the copper catalyst can be one or more of cuprous chloride, cuprous bromide and cuprous iodide, and cuprous iodide is preferred. The palladium catalyst can be one or more of palladium chloride, acetic acid, $PdCl_2(dppf)$, $Pd_2(dba)_3$ and $Pd(PPh_3)_4$.

In addition, the solvent in the above-mentioned step S3111 can be one or more of tetrahydrofuran, 2-methyltetrahydrofuran, ethyl ether, methyl tert-butyl ether, methylcyclopentyl ether and acetonitrile, and 2-methyltetrahydrofuran is preferred. In step S3111, the base can be one or more of potassium carbonate, sodium carbonate, cesium carbonate, triethylamine, diisopropylethylamine, DBU, pyridine and p-dimethylaminopyridine.

In addition, it is preferable that the ratio of amounts used of the compound represented by formula (VI) to the solvent is 1 g:(1-20 mL), preferably 1 g:(5-15 mL). The molar ratio of the compound represented by formula (VI) to the catalyst is 1:(1%-15%), preferably 1:(1%-10%). The molar ratio of the compound represented by formula (VI) to the ligand is 1:(2%-30%), preferably 1:(2-20%); the molar ratio of the compound represented by formula (VI) to the base is 1:(5-15).

3.1.2 Synthesis of Compounds Represented by Trans Structural Formula (II)

When the alkene in the compound represented by formula (II) is a compound represented by the trans structural formula (IIb), the compound represented by formula (IIb) is obtained through a coupling reaction (such as: suzuki coupling reaction) of the compound represented by formula (VI);

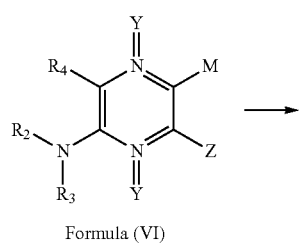

Formula (VI)

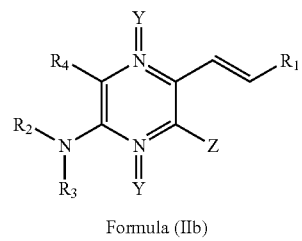

Formula (IIb)

In which M is H or a leaving group, preferably M is a halogen, sulfonic ester, carboxylic ester or phosphoester. The leaving group includes but is not limited to: halogen (for example: Cl, Br, I), $OSO_nR_9$, $OCOR_{10}$ or $OPO_2R_{11}$. $R_9$, $R_{10}$, or $R_{11}$ is independently selected from: —$CF_3$, alkyl, phenyl, or alkyl-substituted phenyl (such as tolyl); n is 0, 1 or 2, and the silicyl group can be a silyl group, etc. Among them, the sulfonic ester can be: methyl benzenesulfonic ester, methanesulfonic ester, trifluoromethanesulfonic ester, etc. More preferably, M is bromine.

Specifically, it can include the following steps:

Mix the compound represented by formula (VI), the trans-1-propenyl boronic acid reagent, the catalyst, the solvent and the ligand for reaction. After the reaction is completed, separate to obtain the compound represented by the trans structural formula (IIb).

It is apprehensible that trans-1-propenyl boronic acid reagents refer to boronic acid reagents containing trans-1-propenyl groups, including but not limited to: trans-1-propenyl boronic acid pinacol ester, trans-1-propenyl boronic acid or trans-1-propenyl fluoroborate.

In addition, the preferred catalyst is selected from one or more of the following reagents: 5% Pd/C, 10% Pd/C, $Pd(OAc)_2$, $PdCl_2(PPh_3)_2$, $Pd(PPh_3)_4$, $PdCl_2(dppf)$, $PdCl_2(MeCN)_2$ and $Pd_2(dba)_3$. The solvent is selected from one or more of the following reagents: methanol, ethanol, isopropanol, butanol, water, tetrahydrofuran, 2-methyltetrahydrofuran, 1,4-dioxane, DME, DMF, DMSO, NMP, acetonitrile, dichloromethane, 1,2-dichloroethane, methyl acetate, ethyl acetate, isopropyl acetate, butyl acetate, ethyl ether, methyl tert-butyl ether, toluene, xylene, acetone, methyl ethyl ketone and methyl cyclopentane. The ligand is selected from one or more of the following reagents: $PPh_3$, BINAP, dppf, Xantphos, Xphos monophosphorus and diphosphorus ligands.

Among them, the compound represented by formula (VI) can be a commercially available raw material, or can be prepared by an existing method. The compound represented by formula (VI) is a pyrazine compound, which is currently widely sold in the market, such as CAS: 6966-01-4, 612835-51-5, 17890-77-6, and 17231-51-5, the cost of which is lower, and thus the preparation cost of the entire process route can be further reduced.

3.2 Synthesis of Compound Represented by Formula (III)

The compound represented by formula (III) can be a commercially available raw material, or can be prepared by an existing method. Further, the compound represented by formula (III) is prepared from the compound represented by formula (II) through a cyclization reaction. That is, first, undergo a cyclization reaction, followed by a dihydroxylation reaction; or first, undergo a dihydroxylation reaction, followed by a cyclization reaction; both are allowed.

3.2.1 Synthesis of the Compound Represented by the Cis Structural Formula (III)

When the alkene in the compound represented by formula (III) is a compound represented by the cis structural formula (IIIa), the compound represented by formula (IIIa) is obtained through catalytic hydrogenation of the compound represented by formula (VIII);

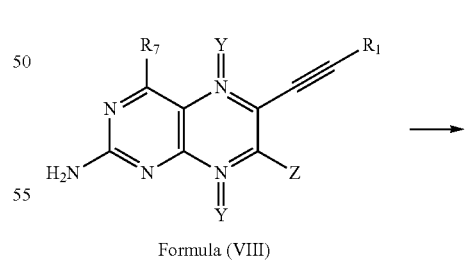

Formula (VIII)

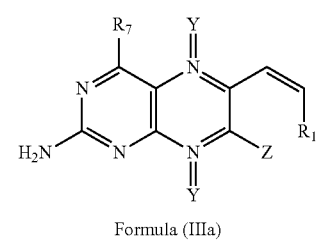

Formula (IIIa)

Specifically, it can include the following steps:

Mix the compound represented by formula (VIII), the catalyst and the solvent, and allow to react under a hydrogen atmosphere. After the reaction is completed, filter and concentrate to obtain the compound represented by the cis structural formula (IIIa).

Among them, the preferred catalyst can be selected from one or more of the following reagents: Lindlar catalyst, palladium/carbon, Raney nickel, platinum black and platinum dioxide; the solvent can be selected from one or more of the following reagents: tetrahydrofuran, 2-methyltetrahydrofuran, ethyl ether, methyl tertiary butyl ether, methylcyclopentyl ether, methanol, ethanol, isopropanol, acetonitrile and toluene.

Preferably, the ratio of amounts used of the compound represented by formula (VIII) to the solvent is 1 g:(1-100 mL), more preferably 1 g:(5-60 mL); the weight ratio of the compound represented by formula (VIII) to the catalyst is 1:(0.005-0.2), more preferably 1:(0.01-0.1); the pressure of hydrogen introduced is 0.1-10 MPa, more preferably 0.1-5 MPa; the reaction temperature is preferably 0-50° C.

Among them, the compound represented by formula (VIII) can be a commercially available raw material, or can be prepared by an existing method. Preferably prepare by the following method:

S3211: The compound represented by formula (VI) undergoes the Sonogashira reaction to obtain the compound represented by formula (V).

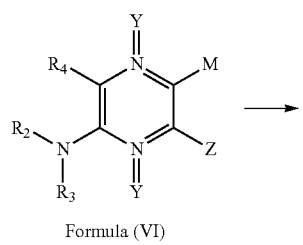

Formula (VI)

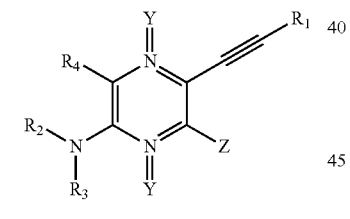

Formula (V)

Specifically, the method described in 53111-53112 can be used to prepare the compound represented by formula (V), which will not be repeated here.

S3212: The compound represented by formula (V) undergoes a cyclization reaction to obtain the compound represented by formula (VIII).

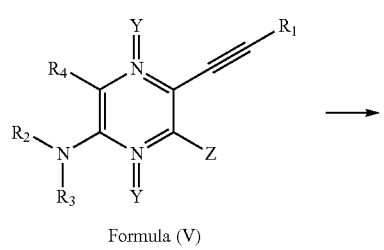

Formula (V)

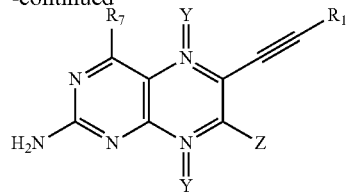

Formula (VIII)

Specifically, the following methods can be used for cyclization:

The compound represented by the formula (V) undergoes a cyclization reaction with

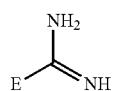

and/or the salt of

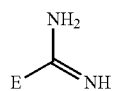

(preferably guanidine salt), which is apprehensible. The

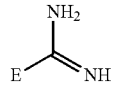

and/or the salt of

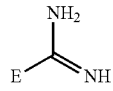

is described as above, which will not be repeated here.

Further, step S3212 can include the following steps: Mix the compound represented by formula (V),

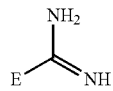

and/or the salt of

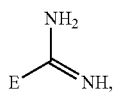

base and solvent, and heat to 50-100° C. for reaction. After the reaction is completed, filter to obtain the compound represented by formula (VIII). Among them, the solvent is an alcohol solvent, preferably one or more of methanol, ethanol and isopropanol; the base can be one or more of sodium ethoxide, sodium methoxide, t-BuONa, t-BuOK and t-BuOLi; a strong base is preferred, such as sodium methoxide.

Further, step S3212 can include the following steps: Add Na to MeOH and stir until the reaction is completed. Then add

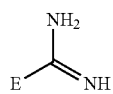

and/or the salt of

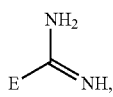

and stir at room temperature for 3-10 min under the protection of $N_2$. Then, filter the insoluble matter in the system, add the compound represented by formula (V), and heat to reflux. After the reaction is completed, allow to cool to room temperature and stir for 40 min-80 min. Filter to obtain the precipitated solid substance, which is the compound represented by formula (VIII).

3.2.2 Synthesis of Compound Represented by the Trans Structural Formula (III)

When the alkene in the compound represented by formula (III) is of a trans structure, the compound represented by formula (III) can be obtained by the following method:

S3221: The compound represented by formula (VI) undergoes a coupling reaction to obtain the compound represented by formula (II);

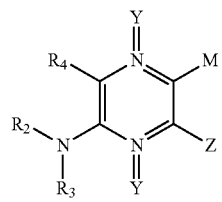

Formula (VI)

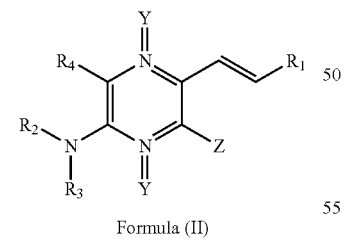

Formula (II)

M is H or a leaving group; preferably M is halogen, sulfonic ester, carboxylic ester or phosphoester. Among them, the sulfonate can be: methyl benzenesulfonic ester, methanesulfonic ester, trifluoromethanesulfonic ester, etc.;

The coupling reaction in step S3221 is the same as above, and will not be repeated here.

S3222: The compound represented by formula (II) undergoes a cyclization reaction to obtain the compound represented by formula (IIIb);

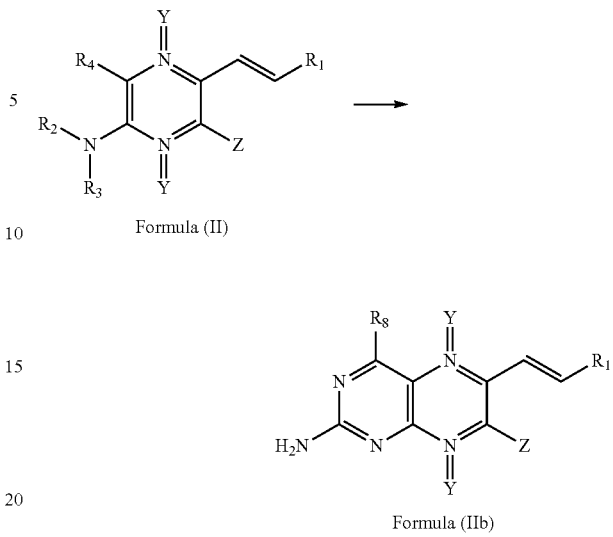

The steps of the cyclization reaction in step S3222 are the same as above, and will not be repeated here.

3. The Optimal Reaction Route

Route One

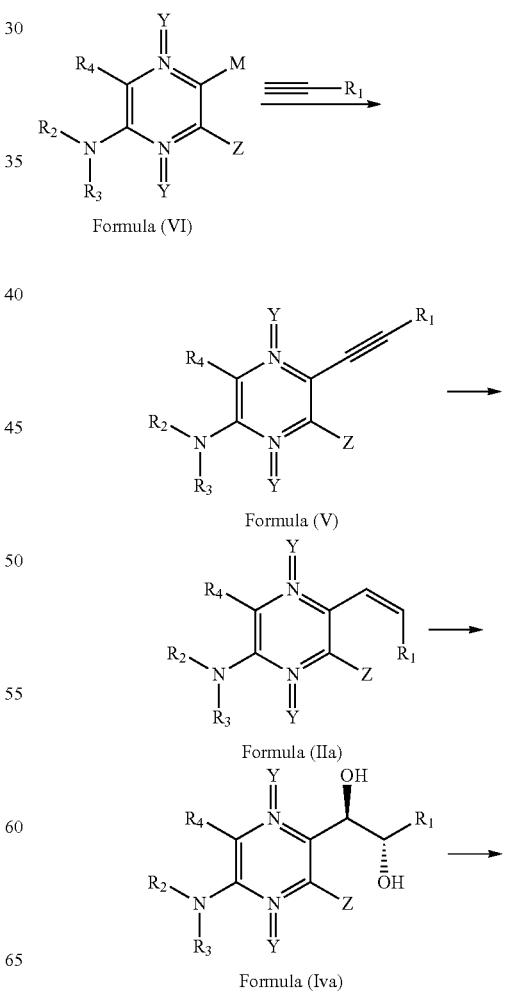

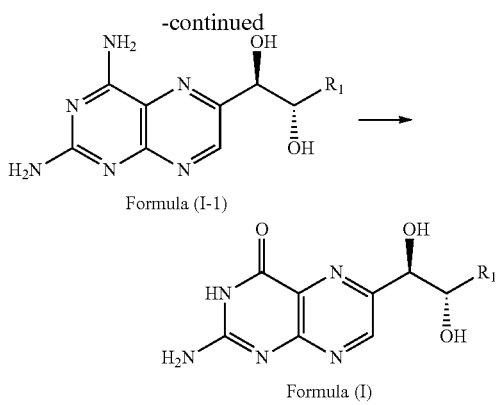

Formula (I-1)

Formula (I)

Among them, the definition of each substituent is described as above, and will not be repeated here. The preparation method of the L-erythro biopterin compound represented by formula (I) includes the following steps:

(1) The compound represented by formula (VI) undergoes the Sonogashira reaction with

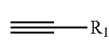

to obtain the compound represented by formula (V);

(2) The compound represented by formula (V) undergoes catalytic hydrogenation to obtain the compound represented by formula (IIa);

(3) The compound represented by formula (IIa) undergoes a dihydroxylation reaction to obtain the compound represented by formula (IVa); preferably, the chiral separation reagent set is used for chiral separation, and the chiral separation reagent set and the method are described as above;

(4) The compound represented by formula (IVa) or the compound (Formula (Iva-1))

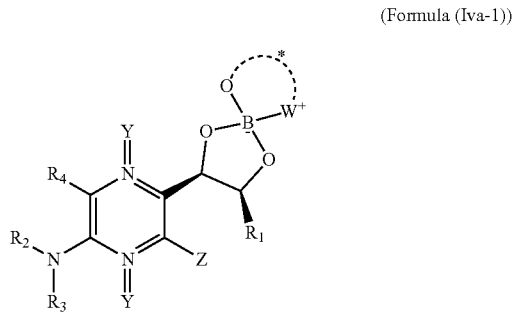

represented by formula (IVa-1) undergoes a cyclization reaction to obtain the compound represented by formula (I-1), and the compound represented by formula (I-1) undergoes hydrolysis to obtain the L-erythro biopterin compound represented by formula (I).

In the above-mentioned (1) to (4), the specific introduction of each reaction is described as above, and will not be repeated here. It is apprehensible that when $R_4$ is —COOR$_5$ or —CONR$_6$, the hydrolysis step in step (4) can be omitted.

In this embodiment, the compound represented by formula (VI) is used as the starting material, which undergoes a cross-coupling reaction with alkyne, followed by catalytic hydrogenation to obtain a cis-alkene. Then, two chiral centers are constructed innovatively by systematic dihydroxylation reaction, then chiral separation and purification are performed to obtain a single enantiomer (R,S)-pyrazine propylene glycol compound, which is then cyclized to obtain the L-erythro biopterin compound. The reaction route is greatly shortened, the yield of each step is high, the atom utilization rate is high, and preparation of L-erythro biopterin by traditional condensation of 5-deoxy-L-arabinose and 2,4,5-triamino-6-hydroxypyrimidine (TAP) is avoided. Therefore, the disadvantages of low efficiency, low yield, high cost and high pollution in the existing industrial manufacturing method are comprehensively overcome.

Route Two

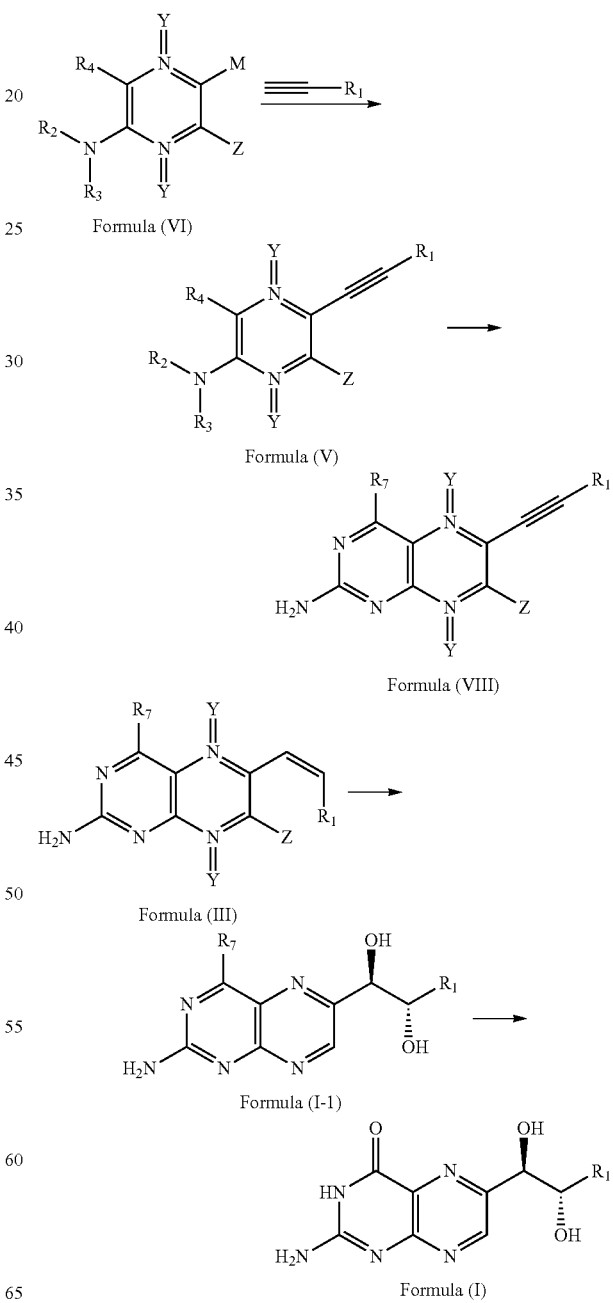

(1) The compound represented by formula (VI) undergoes the Sonogashira reaction with

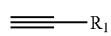

to obtain the compound represented by formula (V);

(2) The compound represented by formula (V) undergoes a cyclization reaction to obtain the compound represented by formula (VIII);

(3) The compound represented by formula (VIII) undergoes catalytic hydrogenation to obtain the compound represented by formula (III);

(4) The compound represented by formula (III) undergoes dihydroxylation reaction to obtain the compound represented by formula (I-1);

(5) The compound represented by formula (I-1) undergoes hydrolysis under alkaline conditions to obtain the L-erythro biopterin compound represented by formula (I).

In the above-mentioned (1) to (5), the specific introduction of each reaction is described as above, and will not be repeated here. It is apprehensible that when $R_4$ is —$COOR_5$ or —$CONR_6$, the hydrolysis step in step (5) can be omitted.

In this embodiment, the compound represented by formula (VI) is used as the starting material, which undergoes a cross-coupling reaction with alkyne, followed by sequential cyclization and catalytic hydrogenation to obtain the desired cis-alkene. Two chiral centers are constructed after dihydroxylation, followed by chiral separation and purification to obtain the desired L-erythro biopterin compound. The reaction route is greatly shortened, the yield of each step is high, the atom utilization rate is high, and preparation of L-erythro biopterin by traditional condensation of 5-deoxy-L-arabinose and 2,4,5-triamino-6-hydroxypyrimidine (TAP) is avoided. Therefore, the disadvantages of low efficiency, low yield, high cost and high pollution in the existing industrial manufacturing method are comprehensively overcome.

Route Three

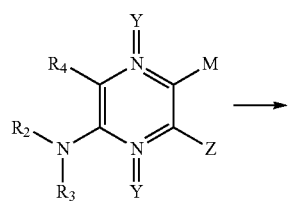

Formula (VI)

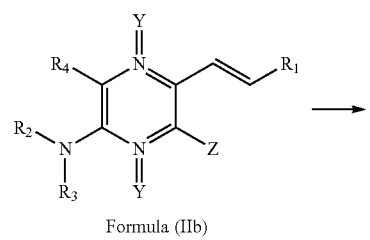

Formula (IIb)

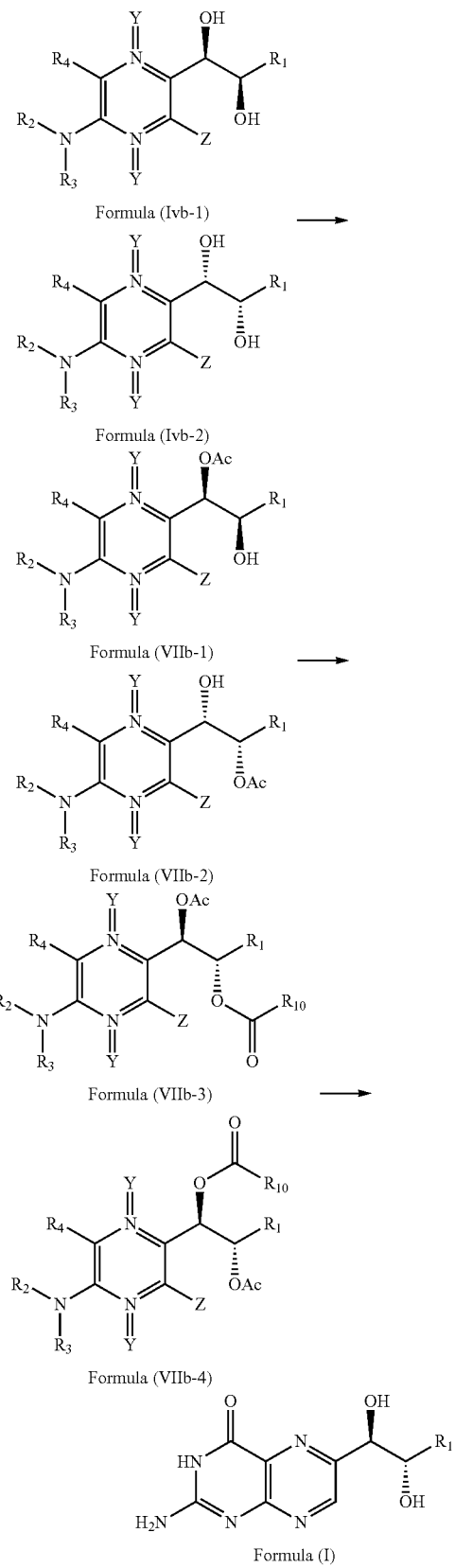

Formula (Ivb-1)

Formula (Ivb-2)

Formula (VIIb-1)

Formula (VIIb-2)

Formula (VIIb-3)

Formula (VIIb-4)

Formula (I)

(1) The compound represented by formula (VI) undergoes a coupling reaction to obtain the compound represented by formula (IIb);

(2) The compound represented by formula (IIb) undergoes a dihydroxylation reaction to obtain the compound represented by formula (IVb-1) and/or formula (IVb-2);

(3) The compound represented by formula (IVb-1) and/or formula (IVb-2) undergoes an acetylation reaction to obtain the compound represented by formula (VIIb-1) and/or formula (VIIb-2);

(4) The compound represented by formula (VIIb-1) and/or formula (VIIb-2) undergoes Mitsunobu reaction to obtain the compound represented by formula (VIIb-3) and/or formula (VIIb-4);

(5) The compound represented by (VIIb-3) and/or formula (VIIb-4) undergoes a cyclization reaction with

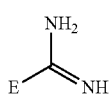

and/or the salt of

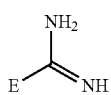

(preferably guanidine salt), followed by hydrolysis to obtain the L-erythro biopterin compound represented by formula (I).

In the above-mentioned (1) to (4), the specific introduction of each reaction is described as above, and will not be repeated here. It is apprehensible that when $R_4$ is —$COOR_5$ or —$CONR_6$, the hydrolysis step in step (5) can be omitted.

In the above-mentioned method, the compound represented by formula (VI) is used as the starting material, the alkene is constructed by a coupling reaction, and the alkene is innovatively subjected to a dihydroxylation reaction, a acetylation reaction and the Mitsunobu reaction to obtain the product of desired configuration. The nature of each reaction is fully utilized, the stereoselectivity is improved, the range for selecting raw materials is expanded, and the by-product of monoacetylation and the by-product that did not flip-over in the Mitsunobu reaction can also be recovered to be raw materials by simple hydrolysis and be reused, which ensures the economy of the entire route. Meanwhile, preparation of L-erythro biopterin by traditional condensation of 5-deoxy-L-arabinose and 2,4,5-triamino-6-hydroxypyrimidine (TAP) is avoided, which avoids environmental pollution and improves production safety.

Specific Embodiments are Listed Below to Illustrate the Present Invention

Embodiment 1

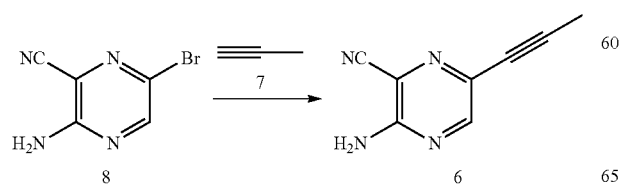

Weigh 200 mg of compound 8, 11 mg of CuI, 10 mg of PdCl$_2$ and 30 mg of PPh$_3$, transfer into a 25-mL three-neck flask, and add 5 mL of acetonitrile. Add 0.7 mL of triethylamine and 1.1 mL of allylene (1 M in THF) while stirring at room temperature, react and stir for 16 h. Add 10 mL of water to quench the reaction, and separate the liquid. Dry and concentrate the organic layer to obtain 163 mg of compound 6, which is a crude product and will be used for the subsequent reaction. IR (cm$^{-1}$) v 3400, 2226, 1647, 1487, 1192; $^1$H NMR (400 MHz, DMSO-d6) δ 8.26 (s, 1H), 7.54 (s, 2H), 2.01 (s, 3H), $^{13}$C NMR (101 MHz, DMSO) δ 155.61, 150.33, 128.08, 115.71, 111.16, 88.27, 76.62, 4.18. HRMS m/z (ESI+) C8H7N4$^+$ requires: 159.0667; found: 159.0671.

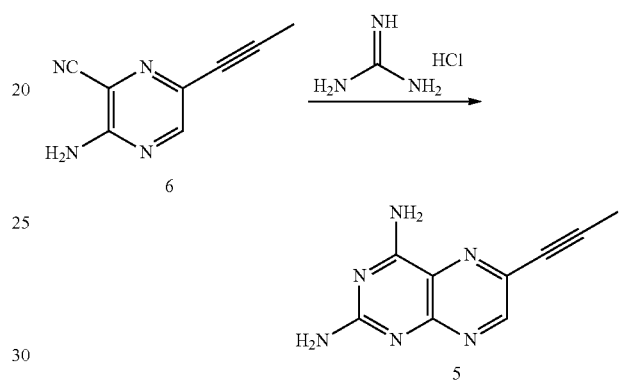

Add 62 mg of Na to 10 mL of MeOH, and stir until the reaction is completed. Add 226 mg of guanidine HCl and stir at room temperature for 5 min under the protection of N$_2$. Filter and remove the insolubles in the system, and add 163 mg of compound 6. Heat to reflux, and stir for 18 h. After cool the reaction system to room temperature, and stir for 1 h. Filter to obtain the yellow crystals precipitated from the system, which are the compound 5 (weight: 144 mg, purity: >99%, yield of the above two steps: 71.6%); IR (cm$^{-1}$) v 3421, 3102, 1635, 1456, 1507, 1063; $^1$H NMR (500 MHz, DMSO-d6) δ 8.91 (s, 1H), 7.08 (s, 2H), 6.33 (s, 2H), 2.06 (s, 3H); $^{13}$C NMR (125 MHz, DMSO) δ 163.83, 162.42, 155.36, 146.65, 136.10, 119.12, 91.24, 83.52, 4.73. HRMS m/z (ESI+) C$_9$H$_9$N$_6$$^+$ requires: 201.4358; found: 201.4359.

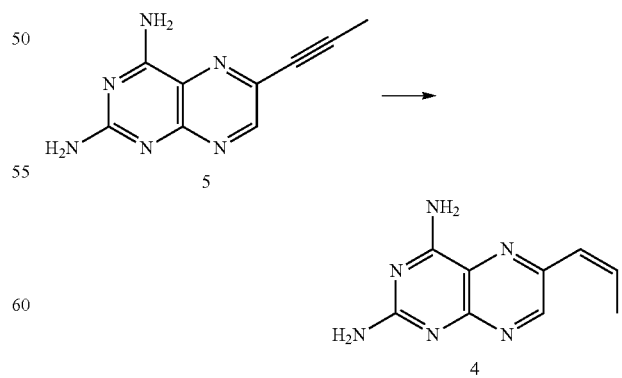

Add 144 mg of compound 5 to 20 mL of THF, and dissolve by heating to 50° C. Add 150 mg of Lindlar Pd, replace with H$_2$, and stir for 3 days at 1 atm. Filter and remove the catalyst. Concentrate to obtain compound 4 (120 mg, purity: 90%, yield: 83%); IR (cm$^{-1}$) v 3294, 1646, 1508, 1479, 1380, 1046; $^1$H NMR (500 MHz, DMSO) δ 8.49 (s, 1H), 7.28 (d, J=9.0 Hz, 1H), 7.07 (d, J=9.5 Hz, 1H), 6.75-6.69 (m, 1H), 6.58 (s, 2H), 6.23 (dq, J=10.5, 6.0 Hz, 1H), 1.92 (dd, J=6.0, 1.1 Hz, 3H). $^{13}$C NMR (125 MHz, DMSO) δ 161.42, 154.82, 147.13, 144.39, 129.56, 126.01, 118.45, 17.04, 16.95. HRMS m/z (ESI+) $C_9H_{11}N_6^+$ requires: 203.2210; found: 203.2208.

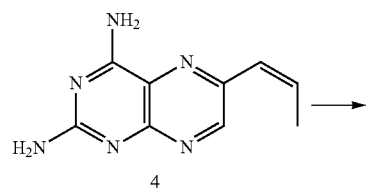

For the dihydroxylation of compound 4, including the following methods:

1) Sharpless Asymmetric Dihydroxylation Reaction

Weigh 5.2 g of AD-mix-α, transfer into a 250-mL three-neck flask, and add 10 mL of water and 10 mL of tert-butyl alcohol. Add 143 mg of MsNH$_2$ and 120 mg of compound 4 while stirring. Allow to react at room temperature, and stir for 16 h. Filter and remove the insolubles. Separate the liquid, extract the aqueous phase three times with ethyl acetate (30 mL×3), and combine the organic phases. Dry over Na$_2$SO$_4$, and concentrate to obtain 151 mg of a dark brown oily substance. Perform chiral preparation with the crude product to obtain a single chiral intermediate 2 (54 mg, with a yield of 42%).

2) Dihydroxylation with KMnO$_4$

Add 100 mg of compound 4 to 10 mL of THE, cool the system to 0° C., and add 10 mL of 1% potassium permanganate aqueous solution (pH=12) and 5 mg of tetrabutylammonium chloride. React at 0° C. and stir overnight. Separate the liquid, extract the aqueous phase with EA (5 mL×3), and combine the organic phases. Dry over Na$_2$SO4, filter, and concentrate. Wash with methanol to obtain 86 mg of a yellow solid. Perform chiral preparation with the crude product to obtain a single chiral intermediate 2 (28 mg, with a yield of 22%).

3) Dihydroxylation with Fe Catalyst

Dissolve 100 mg of compound 4 in 10 mL of THF. Add 5 mL of an aqueous solution containing the catalyst [FeIII (L-N4Me$_2$)Cl$_2$]$^+$ 3.5 mol % oxone (2 equiv) and NaHCO$_3$ (6 equiv), react at room temperature and stir overnight. Separate the liquid, and collect the organic phase. Concentrate, and wash with methanol to obtain 76 mg of a yellow solid crude product. Perform chiral preparation with the crude product to obtain a single chiral intermediate 2 (16 mg, with a yield of 12.4%).

IR (cm$^{-1}$) v 3288, 1655, 1514, 1469, 1379, 1058; $^1$H NMR (500 MHz, DMSO-d6) δ 8.72 (s, 1H), 7.63 (s, 2H), 6.58 (s, 2H), 5.45 (s, 1H), 4.68 (s, 1H), 4.41 (d, J=6.3 Hz, 1H), 3.84 (p, J=6.2 Hz, 1H), 1.11 (d, J=6.2 Hz, 3H); $^{13}$C NMR (126 MHz, DMSO-d6) δ 162.93, 162.81, 155.25, 149.73, 149.60, 120.48, 76.43, 69.73, 19.55; HRMS m/z (ESI+) $C_9H_{13}N_6O_2^+$ requires: 237.1095; found: 237.1094.

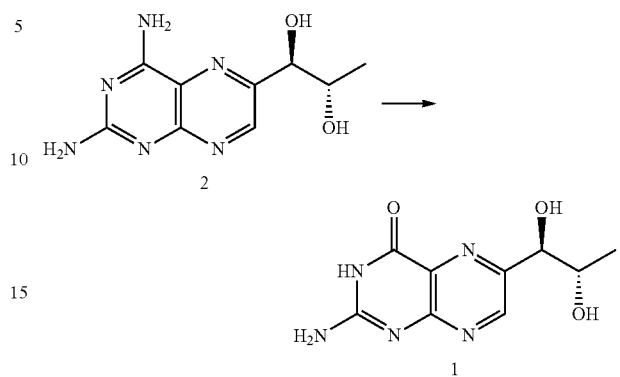

Suspend the obtained 54 mg of compound 2 in 5 mL of NaOH aqueous solution (80 mg) for reaction. Heat to 78° C., and stir for 3 h. Cool to room temperature, and adjust the pH to 5-6 by adding HCOOH dropwise. Filter to obtain the precipitated crystals, which are compound 1, i.e., the L-erythro biopterin compound (51 mg, purity>99%, yield>99%); IR (cm$^{-1}$) v 3249, 1701, 1537, 1490, 1367, 1127; $^1$H NMR (500 MHz, DMSO-d6) δ 11.42 (s, 1H), 8.70 (s, 1H), 6.87 (s, 2H), 5.58 (d, J=4.9 Hz, 1H), 4.69 (d, J=5.3 Hz, 1H), 4.43 (t, J=5.3 Hz, 1H), 3.90 (h, J=6.1 Hz, 1H), 1.05 (d, J=6.3 Hz, 3H); $^{13}$C NMR (126 MHz, DMSO) δ 161.03, 156.55, 153.61, 151.86, 148.98, 127.08, 76.85, 69.42, 19.11. HRMS m/z (ESI+) $C_9H_{12}O_3N_5^+$ requires: 238.0935; found: 238.0935.

Embodiment 2

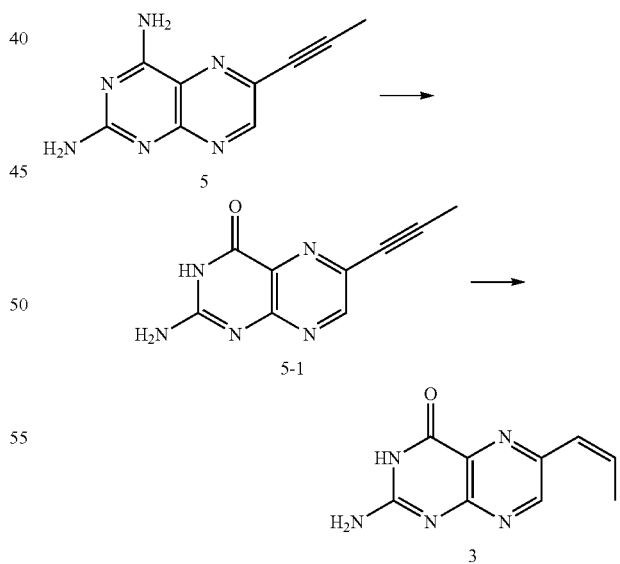

Disperse 200 mg of compound 5 in 5 mL of NaOH aqueous solution (50 mg), heat to 78° C., and stir for 1 h. Adjust the pH to 5-6 by adding acetic acid dropwise, filter to obtain the precipitated solids and wash with methanol to obtain compound 5-1 (152 mg, with a purity of 98%, and a yield of 76%);

Dissolve 152 mg of compound 5-1 in 5 mL of a combined solution of MeOH/DCM=1/1, and stir thoroughly to dissolve. Add 100 mg of Lindlar Pd, replace with $H_2$ (1 atm), and stir at room temperature for 3 days. Filter and remove the catalyst. Concentrate the solvent to obtain compound 3 (150 mg, purity: 95%, yield: 93%); $^1$H NMR (500 MHz, DMSO) δ 12.3 (s, 1H), 8.53 (s, 1H), 6.49 (s, 2H), 2.04 (s, 3H). $^{13}$C NMR (125 MHz, DMSO) δ 161.85, 156.13, 150.79, 148.55, 136.37, 127.07, 92.12, 85.24, 4.59. HRMS m/z (ESI+) $C_9H_{10}N_5O^+$ requires: 203.2050, found: 203.2051.

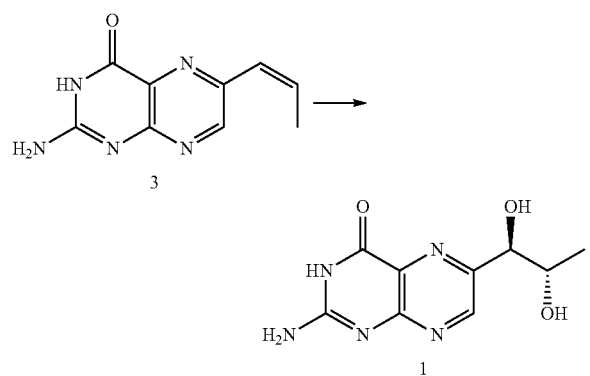

For the dihydroxylation of compound 3, including the following methods:

1) Sharpless Asymmetric Dihydroxylation Reaction

Weigh 2.6 g of AD-mix-α, transfer into a 100-mL three-neck flask, and add 5 mL of $H_2O$ and 5 mL of t-BuOH. Add 70 mg of $MsNH_2$ and 150 mg of compound 3 while stirring. Allow to react at room temperature, and stir for 16 h. Filter and remove the insolubles. Separate the liquid, extract the aqueous phase three times with 2-MeTHF (30 mL×3), and combine the organic phases. Dry over $Na_2SO_4$, and concentrate to obtain 56 mg of a dark brown oily substance. Perform chiral preparation with the crude product to obtain a single chiral compound 1 (19 mg, with a yield of 11%).

2) Dihydroxylation with $KMnO_4$

Prepare 10 mL of 1% potassium permanganate aqueous solution (pH 12), and add 150 mg of compound 3. React at 0° C. and stir overnight. Add $Na_2SO_3$ to quench the reaction, adjust the pH to 5-7 by adding acetic acid dropwise, and filter the product. Perform chiral preparation with the crude product to obtain a single chiral compound 1 (40 mg, with a yield of 21%).

3) Dihydroxylation with Fe Catalyst

Add 150 mg of compound 3 to 5 mL of an aqueous solution containing the catalyst $[FeIII(L-N4Me_2)Cl_2]^+$ 3.5 moL % oxone (2 equiv) and $NaHCO_3$ (6 equiv), react at room temperature and stir overnight. Add $Na_2SO_3$ to quench the reaction, and adjust the pH to 5-7 by adding acetic acid dropwise. Filter to obtain the precipitated product. Perform chiral preparation with the crude product to obtain a single chiral compound 1 (15 mg, with a yield of 8.7%).

IR (cm$^{-1}$) v 3249, 1701, 1537, 1490, 1367, 1127; $^1$H NMR (500 MHz, DMSO-d6) δ 11.42 (s, 1H), 8.70 (s, 1H), 6.87 (s, 2H), 5.58 (d, J=4.9 Hz, 1H), 4.69 (d, J=5.3 Hz, 1H), 4.43 (t, J=5.3 Hz, 1H), 3.90 (h, J=6.1 Hz, 1H), 1.05 (d, J=6.3 Hz, 3H); $^{13}$C NMR (126 MHz, DMSO) δ 161.03, 156.55, 153.61, 151.86, 148.98, 127.08, 76.85, 69.42, 19.11. HRMS m/z (ESI+) $C_9H_{12}O_3N_5^+$ requires: 238.0935; found: 238.0935.

Embodiment 3

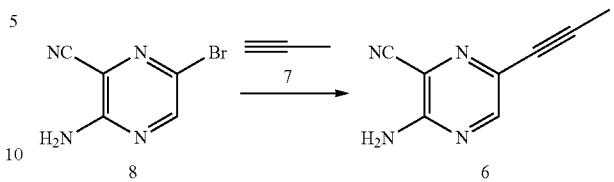

Weigh 200 mg of compound 8, 11 mg of CuI, 10 mg of $PdCl_2$ and 30 mg of $PPh_3$, transfer into a 25-mL three-neck flask, and add 5 mL of acetonitrile. Add 0.7 mL of triethylamine and 1.1 mL of allylene (1 M in THF) while stirring at room temperature, react and stir for 16 h. Add 10 mL of water to quench the reaction, and separate the liquid. Dry the organic layer, and concentrate to obtain 160 mg of compound 6, which is a crude product and will be used for the subsequent reaction.

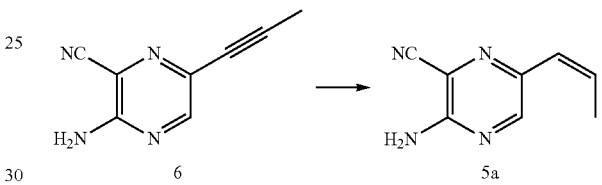

Place the obtained 500 mg of compound 6 in a high-pressure reaction kettle. Add 500 mg of Lindlar catalyst and 10 mL of THF. Replace with $H_2$ for three times, and stir at room temperature for 16 h. Filter and remove the catalyst. Concentrate to obtain 400 mg of compound 5a; IR (cm$^{-1}$) v 3401, 3202, 2222, 1644, 1492, 1515, 1172; $^1$H NMR (500 MHz, DMSO-d6) δ 8.27 (s, 1H), 7.33 (s, 2H), 6.30 (dq, J=11.7, 1.8 Hz, 1H), 5.88 (dq, J=11.7, 7.3 Hz, 1H), 2.01 (dd, J=7.3, 1.8 Hz, 3H); $^{13}$C NMR (126 MHz, DMSO) δ 154.87, 147.91, 141.32, 129.95, 124.29, 116.05, 109.58, 14.88; HRMS m/z (ESI+) $C_8H_9N_4^+$ requires: 161.0822; found: 161.0821.

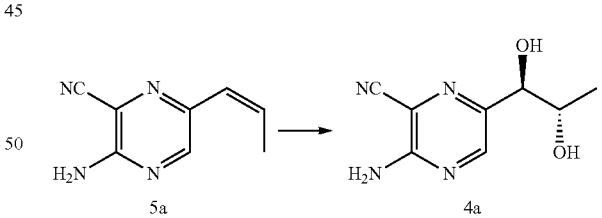

For the dihydroxylation of compound 5a, including the following methods:

1) Sharpless Asymmetric Dihydroxylation Reaction

Weigh 6.5 g of AD-mix-α, transfer into a 250-mL three-neck flask, and add 10 mL of water and 10 mL of tert-butyl alcohol. Add 180 mg of $MsNH_2$ and 350 mg of compound 5a while stirring. Allow to react at room temperature, and stir for 16 h. Filter and remove the insolubles. Separate the liquid, extract the aqueous phase three times with ethyl acetate (30 mL×3), and combine the organic phases. Dry over $NaS_2O_4$, and concentrate to obtain 200 mg of a dark brown oily substance. Perform chiral preparation with the crude product to obtain a single chiral intermediate 4a; IR (cm⁻¹) v 3374, 3196, 2236, 1655, 1572, 1496, 1065; $^1$H NMR (500 MHz, DMSO-d6) δ 8.30 (s, 1H), 7.17 (s, 2H), 5.42 (d, J=5.1 Hz, 1H), 4.57 (d, J=5.3 Hz, 1H), 4.21 (dd, J=6.0, 5.1 Hz, 1H), 3.84-3.75 (m, 1H), 1.04 (d, J=6.2 Hz, 3H); $^{13}$C NMR (126 MHz, DMSO) δ 156.21, 146.77, 146.63, 116.26, 108.70, 76.21, 69.18, 19.34; HRMS m/z (ESI+) $C_8H_{11}N_4O_2^+$ requires: 195.0877; found: 195.0878.

2) Dihydroxylation with KMnO₄:

Add 80 mg of compound 5a to 10 mL of THF, cool the system to 0° C., and add 10 mL of 1% potassium permanganate aqueous solution (pH=12) and 5 mg of tetrabutylammonium chloride. React at 0° C. and stir overnight. Separate the liquid, extract the aqueous phase with EA (5 mL×3), and combine the organic phases. Dry over Na₂SO₄, filter and concentrate. Then wash with methanol to obtain 88 mg of a yellow solid. Perform chiral preparation with the crude product to obtain a single chiral intermediate 4a (31 mg, with a yield of 32%).

3) Dihydroxylation with Fe catalyst

Dissolve 80 mg of compound 5a in 10 mL of THF. Add 5 mL of an aqueous solution containing the catalyst [FeIII (L-N4Me₂)Cl₂]⁺ 3.5 moL % oxone (2 equiv) and NaHCO₃ (6 equiv). React at room temperature and stir overnight. Separate the liquid, and collect the organic phase. Concentrate, and wash with methanol to obtain 64 mg of a yellow solid crude product. Perform chiral preparation with the crude product to obtain a single chiral intermediate 4a (13 mg, with a yield of 17%).

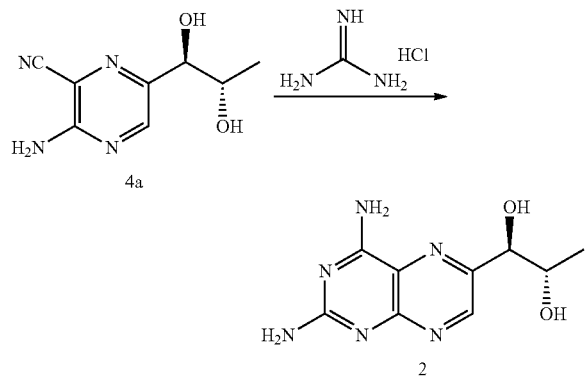

Add 62 mg of Na to 10 mL of MeOH, and stir until the reaction is completed. Add 226 mg of guanidine HCl and stir at room temperature for 5 min under the protection of N₂. Filter and remove the insolubles in the system. Add 200 mg of single chiral intermediate 4a. Heat to reflux, and stir for 18 h. Cool the reaction system to room temperature, and stir for 1 h. Filter to obtain the yellow crystals precipitated from the system, which are compound 2 (weight: 150 mg, purity>99%, yield: 68%);

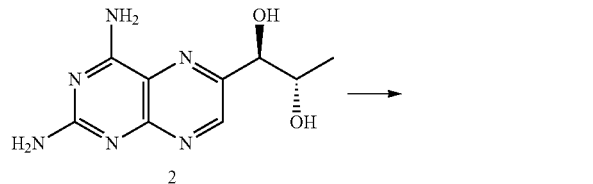

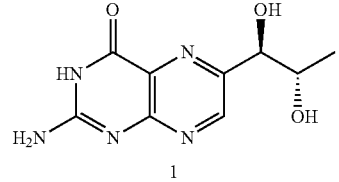

Suspend the obtained 100 mg of compound 2 in 10 mL of NaOH aqueous solution (160 mg), heat to 78° C. and stir for 3 h for reaction. Cool to room temperature, and adjust the pH to 5-6 by adding HCOOH dropwise. Filter to obtain the precipitated crystals, which are compound 1, i.e., the L-erythro biopterin compound (100 mg, purity>99%, yield>99%); IR (cm⁻¹) v 3249, 1701, 1537, 1490, 1367, 1127; $^1$H NMR (500 MHz, DMSO-d6) δ 11.42 (s, 1H), 8.70 (s, 1H), 6.87 (s, 2H), 5.58 (d, J=4.9 Hz, 1H), 4.69 (d, J=5.3 Hz, 1H), 4.43 (t, J=5.3 Hz, 1H), 3.90 (h, J=6.1 Hz, 1H), 1.05 (d, J=6.3 Hz, 3H); $^{13}$C NMR (126 MHz, DMSO) δ 161.03, 156.55, 153.61, 151.86, 148.98, 127.08, 76.85, 69.42, 19.11. HRMS m/z (ESI+) $C_9H_{12}O_3N_5^+$ requires: 238.0935; found: 238.0935.

Embodiment 4

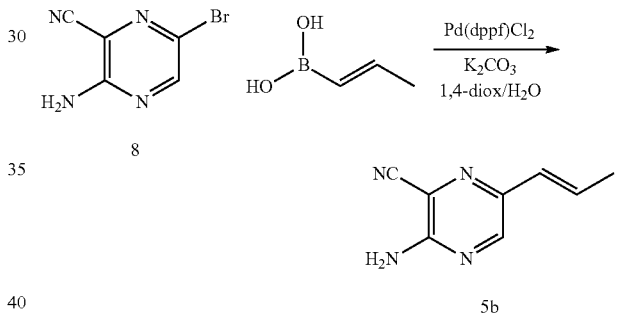

Weigh 200 mg of compound 8, 104 mg of E-propenylboric acid, 37 mg of Pd(dppf)Cl₂, 500 mg of K₂CO₃, and dissolve in 1,4-diox/H₂O (v/v=3 mL/2 mL) for reaction. Heat to reflux, and stir for 3 h. The reaction, which is monitored by TLC, is completed. Separate the liquid, extract the aqueous phase with EA, and combine the organic phases. Dry over Na₂SO₄, and perform chromatography with the concentration column (EA/heptane=1/5-1/3) to obtain a yellow solid 5b (100 mg); IR (cm⁻¹) v 3384, 2231, 1667, 1574, 1498, 1316, 1166; $^1$H NMR (500 MHz, DMSO-d6) δ 8.31 (s, 1H), 7.18 (s, 2H), 5.35 (d, J=5.4 Hz, 1H), 4.54 (d, J=5.4 Hz, 1H), 4.26 (t, J=5.0 Hz, 1H), 3.81-3.71 (m, 1H), 1.00 (d, J=6.4 Hz, 3H); $^{13}$C NMR (126 MHz, DMSO) δ 156.14, 146.56, 146.40, 116.20, 108.75, 75.85, 69.04, 19.22; HRMS m/z (ESI+) $C_8H_{11}N_4O_2^+$ requires: 195.0879; found: 195.0877.

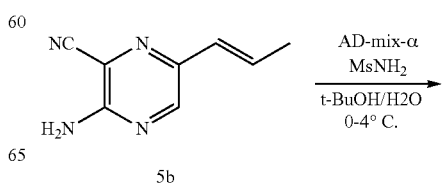

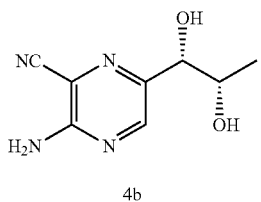

4b

For the dihydroxylation of compound 5b, including the following methods:

1) Sharpless Asymmetric Dihydroxylation Reaction

Weigh 7.0 g of AD-mix-α, disperse in t-BuOH/H₂O (30 mL/30 mL), and stir at 0° C. for 5 min. Add 475 mg of MsNH₂, and stir at 0° C. for 5 min. Then add 800 mg of compound 5b, heat to 4° C., react and stir for 2 d. After the reaction, which is monitored by HPLC, is completed, add 10 g of Na₂SO₃ into the system, and stir at room temperature for 30 min. Filter and wash the filtration residues with 50 mL of EA. After the filtrate is separated, extract the aqueous phase with EA (50 mL×3). Combine the organic phases, dry over Na₂SO₄, and purify by column chromatography (HEP: EA=5:1-0:1) to obtain a light-yellow solid 4b (1.08 g, yield>99%, purity=98%, ee=94%); IR (cm⁻¹) v 3384, 2231, 1667, 1574, 1498, 1316, 1166; ¹H NMR (500 MHz, DMSO-d6) δ 8.31 (s, 1H), 7.18 (s, 2H), 5.35 (d, J=5.4 Hz, 1H), 4.54 (d, J=5.4 Hz, 1H), 4.26 (t, J=5.0 Hz, 1H), 3.81-3.71 (m, 1H), 1.00 (d, J=6.4 Hz, 3H); ¹³C NMR (126 MHz, DMSO) δ 156.14, 146.56, 146.40, 116.20, 108.75, 75.85, 69.04, 19.22; HRMS m/z (ESI+) C₈H₁₁N₄O₂⁺ requires: 195.0879; found: 195.0877.

2) Dihydroxylation with KMnO₄

Add 80 mg of compound 5b to 10 mL of THF, cool the system to 0° C., and add 10 mL of 1% potassium permanganate aqueous solution (pH=12) and 5 mg of tetrabutylammonium chloride. React at 0° C. and stir overnight. Separate the liquid, extract the aqueous phase with EA (5 mL×3), and combine the organic phases. Dry over Na₂SO₄, filter and concentrate. Then wash with methanol to obtain 91 mg of a yellow solid. Perform chiral preparation with the crude product to obtain a single chiral intermediate 4b (33 mg, with a yield of 34%).

3) Dihydroxylation with Fe Catalyst

Dissolve 80 mg of compound 5b in 10 mL of THF. Add 5 mL of an aqueous solution containing the catalyst [FeIII (L-N4Me₂)Cl₂]⁺ 3.5 moL % oxone (2 equiv) and NaHCO₃ (6 equiv). React at room temperature and stir overnight. Separate the liquid, and collect the organic phase. Concentrate, and wash with methanol to obtain 64 mg of a yellow solid crude product. Perform chiral preparation with the crude product to obtain a single chiral intermediate 4b (15 mg, with a yield of 20%).

IR (cm⁻¹) v 3384, 2231, 1667, 1574, 1498, 1316, 1166; H NMR (500 MHz, DMSO-d6) δ 8.31 (s, 1H), 7.18 (s, 2H), 5.35 (d, J=5.4 Hz, 1H), 4.54 (d, J=5.4 Hz, 1H), 4.26 (t, J=5.0 Hz, 1H), 3.81-3.71 (m, 1H), 1.00 (d, J=6.4 Hz, 3H); ¹³C NMR (126 MHz, DMSO) δ 156.14, 146.56, 146.40, 116.20, 108.75, 75.85, 69.04, 19.22; HRMS m/z (ESI+) C₈H₁₁N₄O₂⁺ requires: 195.0879; found: 195.0877.

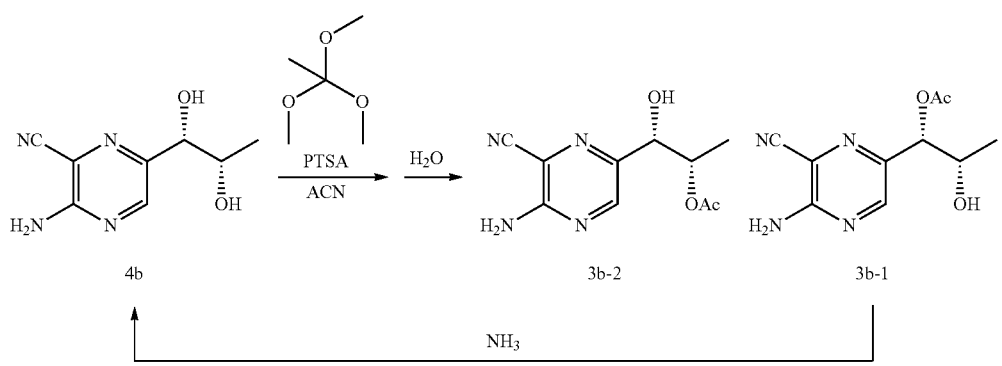

Disperse 800 mg of compound 4b in 100 mL of ACN, and stir thoroughly. Add 1.48 g of H₃CC(OEt)₃ and 39 mg of PTSA, stir until they are completely dissolved, and continue stirring for 30 min. Then add 1 mL of H₂O to the system, and continue stirring for 30 min. After the reaction of raw materials, which is monitored by TLC, is completed, two kinds of products are generated. Directly add silica gel to the system, stir, and perform column chromatography to obtain 400 mg of compound 3b-2, and 421 mg of a mixture of compounds 3b-1 and 3b-2. Add the mixture of compounds 3b-1 and 3b-2 to NH₃/MeOH solution, and stir for 30 min. Compound 4b is generated. Repeat the above-mentioned monoacetylation process to obtain 260 mg of compound 3b-2. A total of 660 mg of compound 3b-2 is obtained from the two reactions, with a purity of 90% and a yield of 61%;

Data in the spectra of compound 3b-2: IR (cm⁻¹) v 3452, 3340, 2223, 1697, 1616, 1482, 1372, 1044; ¹H NMR (500 MHz, DMSO-d6) δ 8.33 (s, 1H), 7.29 (s, 2H), 5.77 (d, J=5.3 Hz, 1H), 5.03 (qd, J=6.5, 5.1 Hz, 1H), 4.53 (t, J=5.3 Hz, 1H), 1.93 (s, 3H), 1.10 (d, J=6.5 Hz, 3H). ¹³C NMR (126 MHz, DMSO) δ 169.75, 156.23, 146.23, 144.84, 115.98, 109.15, 73.02, 72.05, 20.88, 16.00. HRMS m/z (ESI+) C₁₀H₁₂O₃N₄Na⁺ requires: 259.0802; found: 259.0801.

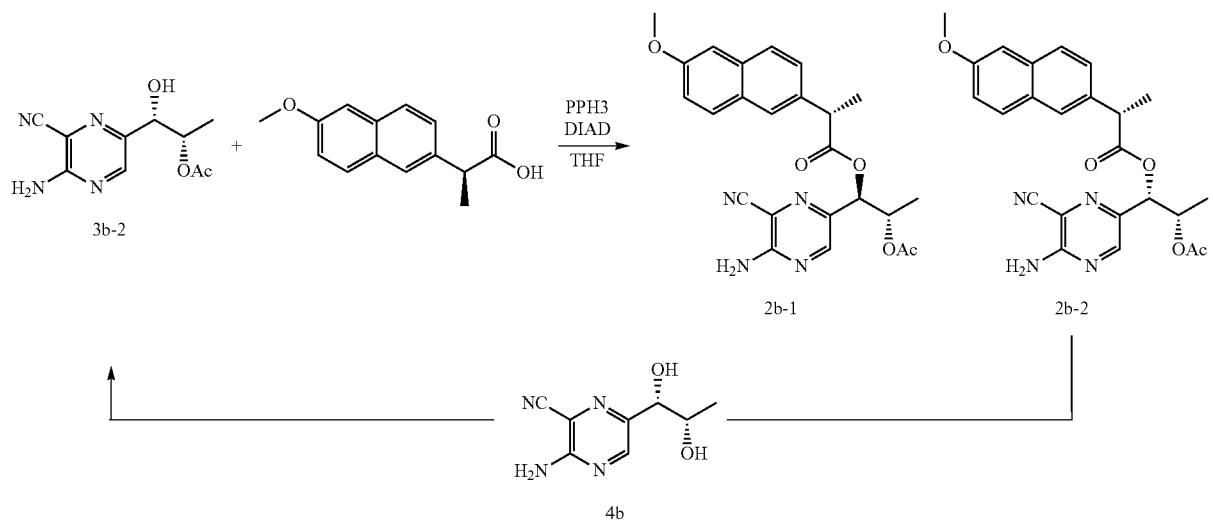

Weigh 500 mg of compound 3b-2, 732 mg of naproxen, 834 mg of PPh₃, and dissolve in 30 mL of THF. Add 0.63 mL of DIAD dropwise at 0° C., react and stir overnight. After the reaction is completed, which is monitored by HPLC, add saturated NaHCO₃ aqueous solution into the system to quench the reaction. Separate the liquid, and extract the aqueous phase with EA (20 mL×2). Combine the organic phases, dry over Na₂SO₄, and concentrate. Perform column chromatography (EA/Heptane=1/2) to obtain compound 2b-1 (272 mg, with a purity of 97%, and a yield of 28%) and compound 2b-2 (610 mg), respectively. Add the obtained compound 2b-2 to NH₃/MeOH solution, stir for 1 h to obtain 260 mg of compound 4b again, which is recovered and used as raw material in the upstream reaction.

Data in the spectra of compound 2b-1: IR (cm⁻¹) v 3331, 2224, 1740, 1630, 1233; ¹H NMR (500 MHz, DMSO-d6) δ 7.90-7.69 (m, 4H), 7.48-7.36 (m, 3H), 7.34-7.23 (m, 1H), 7.19-7.10 (m, 1H), 5.69 (d, J=4.2 Hz, 1H), 5.28-5.13 (m, 1H), 4.05 (q, J=7.0 Hz, 1H), 3.86 (s, 3H), 1.89 (s, 3H), 1.51 (d, J=7.1 Hz, 3H), 1.09 (d, J=6.6 Hz, 3H); ¹³C NMR (126 MHz, DMSO) δ 172.77, 169.44, 157.23, 156.29, 145.61, 139.20, 134.99, 133.36, 129.14, 128.36, 126.92, 126.27, 125.81, 118.82, 115.55, 109.62, 105.74, 74.45, 69.72, 55.15, 44.36, 20.64, 17.80, 14.74. HRMS m/z (ESI+) $C_{24}H_{24}O_5N_4Na^+$ requires: 471.1639; found: 471.1637.

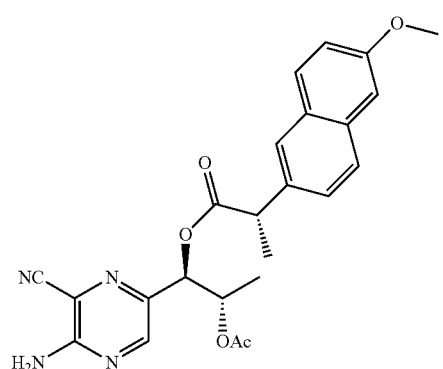

2b-1

-continued

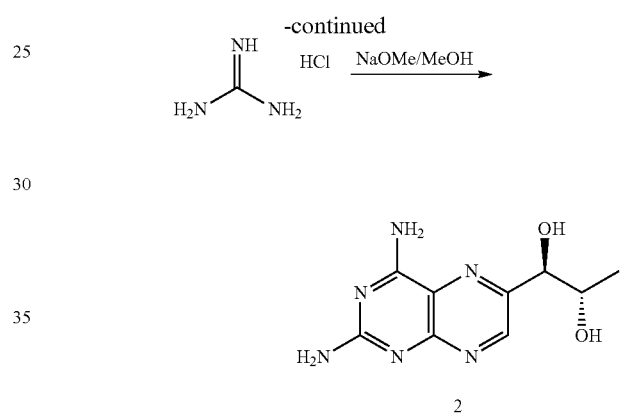

Weigh 77 mg of Na, add into 30 mL of methanol, and stir thoroughly until the reaction is completed. Transfer 3 mL of the above solution, add 32 mg of guanidine HCl, and stir for 5 min under the protection of N₂. Filter and remove the insolubles. Add 50 mg of compound 2b-1 for reaction. Heat to reflux and stir overnight. Bright yellow crystals are precipitated. Filter to obtain the precipitated crystals, which are compound 2 (15.3 mg, with a yield of 58%); IR (cm⁻¹) v 3288, 1655, 1514, 1469, 1379, 1058; ¹H NMR (500 MHz, DMSO-d6) δ 8.72 (s, 1H), 7.63 (s, 2H), 6.58 (s, 2H), 5.45 (s, 1H), 4.68 (s, 1H), 4.41 (d, J=6.3 Hz, 1H), 3.84 (p, J=6.2 Hz, 1H), 1.11 (d, J=6.2 Hz, 3H); ¹³C NMR (126 MHz, DMSO) δ 162.93, 162.81, 155.25, 149.73, 149.60, 120.48, 76.43, 69.73, 19.55; HRMS m/z (ESI+) $C_9H_{13}N_6O_2^+$ requires: 237.1095; found: 237.1094.

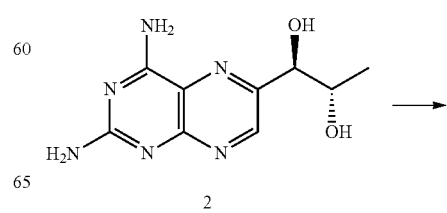

2

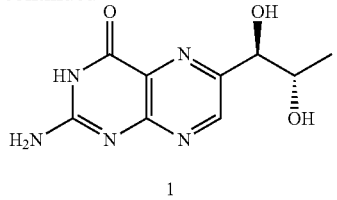

Suspend the obtained 100 mg of compound 2 in 10 mL of NaOH aqueous solution (160 mg), heat to 78° C. and stir for 3 h for reaction. Cool to room temperature, and adjust the pH to 5-6 by adding HCOOH dropwise. Filter to obtain the precipitated crystals, which are compound 1, i.e., the L-erythro biopterin compound (100 mg, purity>99%, yield>99%);

Embodiment 5

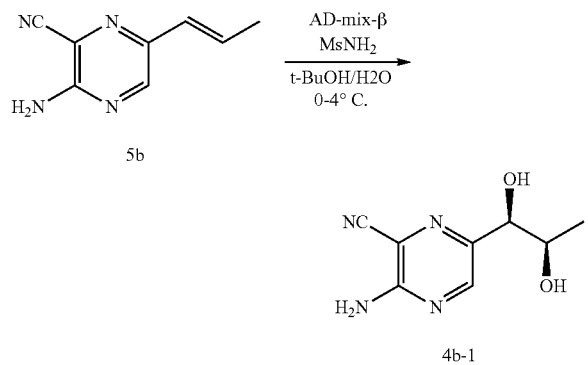

For the dihydroxylation of compound 5b, including the following methods:

1) Sharpless Asymmetric Dihydroxylation Reaction

Weigh 7.0 g of AD-mix-$, disperse in t-BuOH/H₂O (30 mL/30 mL), and stir at 0° C. for 5 min. Add 475 mg of MsNH₂, and stir at 0° C. for 5 min. Then add 800 mg of compound 5b, heat to 4° C., react and stir for 2 d. After the reaction, which is monitored by HPLC, is completed, add 10 g of Na₂SO₃ to the system, and stir at room temperature for 30 min. Filter and wash the filtration residues with 50 mL of EA. After the filtrate is separated, extract the aqueous phase with EA (50 mL×3), and combine the organic phases. Dry over Na₂SO₄, and purify by column chromatography (HEP:EA=5:1-0:1) to obtain a light-yellow solid 4b-1 (979 mg, yield>99%, purity=98%, ee=92%);

IR (cm$^{-1}$) v 3374, 2230, 1668, 1570, 1486, 1166; $^1$H NMR (500 MHz, DMSO-d6) δ 8.31 (s, 1H), 7.18 (s, 2H), 5.35 (d, J=5.4 Hz, 1H), 4.54 (d, J=5.4 Hz, 1H), 4.26 (t, J=5.0 Hz, 1H), 3.81-3.71 (m, 1H), 1.00 (d, J=6.4 Hz, 3H); $^{13}$C NMR (126 MHz, DMSO) δ 156.14, 146.56, 146.40, 116.20, 108.75, 75.85, 69.04, 19.22; HRMS m/z (ESI+) $C_8H_{11}N_4O_2^+$ requires: 195.0879; found: 195.0877.

2) Dihydroxylation with KMnO₄

Add 80 mg of compound 5b to 10 mL of THF, cool the system to 0° C., and add 10 mL of 1% potassium permanganate aqueous solution (pH=12) and 5 mg of tetrabutylammonium chloride. React at 0° C. and stir overnight. Separate the liquid, extract the aqueous phase with EA (5 mL×3), and combine the organic phases. Dry over Na₂SO₄, filter and concentrate. Then wash with methanol to obtain 91 mg of a yellow solid. Perform chiral preparation with the crude product to obtain a single chiral intermediate 4b-1 (29 mg, with a yield of 30%).

3) Dihydroxylation with Fe Catalyst

Dissolve 80 mg of compound 5b in 10 mL of THF. Add 5 mL of an aqueous solution containing the catalyst [FeIII (L-N4Me₂)Cl₂]⁺ 3.5 moL % oxone (2 equiv) and NaHCO₃ (6 equiv). React at room temperature and stir overnight. Separate the liquid, and collect the organic phase. Concentrate, and wash with methanol to obtain 64 mg of a yellow solid crude product. Perform chiral preparation with the crude product to obtain a single chiral intermediate compound 4b-1 (12 mg, with a yield of 16%); IR (cm$^{-1}$) v 3384, 2231, 1667, 1574, 1498, 1316, 1166; H NMR (500 MHz, DMSO-d6) δ 8.31 (s, 1H), 7.18 (s, 2H), 5.35 (d, J=5.4 Hz, 1H), 4.54 (d, J=5.4 Hz, 1H), 4.26 (t, J=5.0 Hz, 1H), 3.81-3.71 (m, 1H), 1.00 (d, J=6.4 Hz, 3H); $^{13}$C NMR (126 MHz, DMSO) δ 156.14, 146.56, 146.40, 116.20, 108.75, 75.85, 69.04, 19.22; HRMS m/z (ESI+) $C_8H_{11}N_4O_2^+$ requires: 195.0879; found: 195.0877.

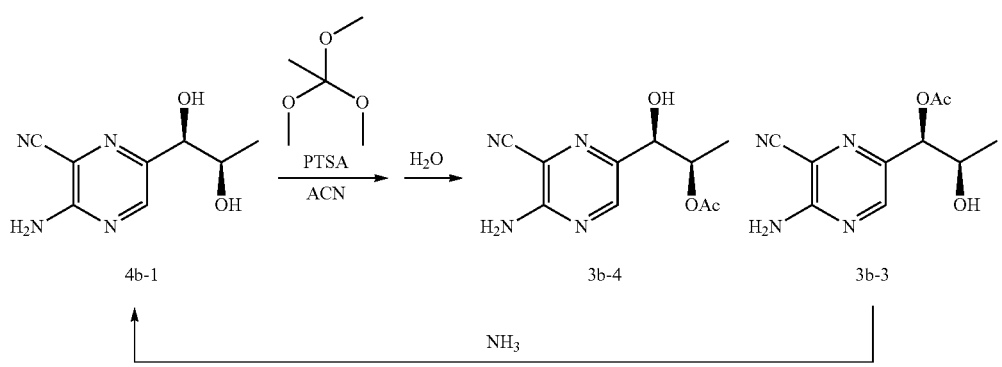

Disperse 800 mg of compound 4b-1 in 100 mL of ACN, and stir thoroughly. Add 1.48 g of H₃CC(OEt)₃ and 39 mg of PTSA, stir until they are completely dissolved. Continue to stir for 30 min, then add 1 mL of H₂O into the system, and stir for 30 min. After the reaction, which is monitored by TLC, is completed, two kinds of products are generated. Directly add silica gel to the system, stir, and perform chromatography to obtain 200 mg of compound 3b-3, and 611 mg of a mixture of compound 3b-4 and 3b-3. Add the mixture of compound 3b-4 and 3b-3 to NH₃/MeOH solution, and stir for 30 min. Compound 4b-1 is generated.

Repeat the above-mentioned monoacetylation process to obtain 240 mg of compound 3b-3. A total of 440 mg of compound 3b-4 is obtained from the two reactions, with a purity of 90% and a yield of 41%. IR (cm$^{-1}$) v 3426, 2220, 1683, 1606, 1485, 1373; $^1$H NMR (500 MHz, DMSO-d6) δ 8.28 (s, 1H), 7.38 (s, 2H), 5.38 (d, J=6.0 Hz, 1H), 4.04-3.96 (m, 1H), 2.08 (s, 3H), 0.98 (d, J=6.4 Hz, 3H); $^{13}$C NMR (126 MHz, DMSO) δ 170.00, 156.37, 146.69, 141.44, 115.84, 109.67, 77.50, 66.91, 20.81, 19.06. HRMS m/z (ESI+) $C_{10}H_{12}O_3N_4Na^+$ requires: 259.0802; found: 259.0803.

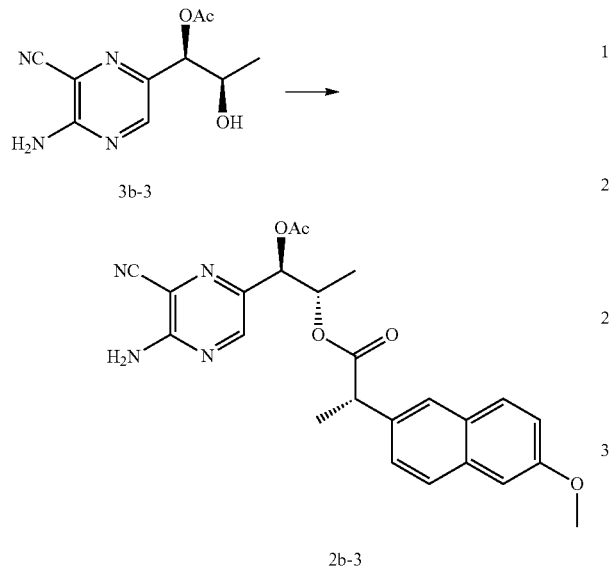

Weigh 100 mg of compound 3b-3, 147 mg of naproxen, 167 mg of PPh$_3$, and dissolve in 10 mL of THF. Add 0.2 mL of DIAD dropwise at 0° C., react and stir overnight. After the reaction, which is monitored by HPLC, is completed, add saturated NaHCO$_3$ aqueous solution into the system to quench the reaction. Separate the liquid, and extract the aqueous phase with EA (20 mL×2). Combine the organic phases, dry over Na$_2$SO$_4$, perform chromatography of the concentration column (EA/Heptane=1/2), to obtain compound 2b-3 (52 m, with a purity of 97%, and a yield of 27%).

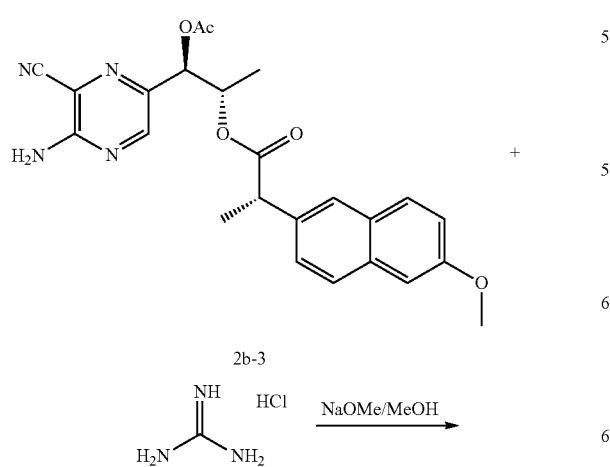

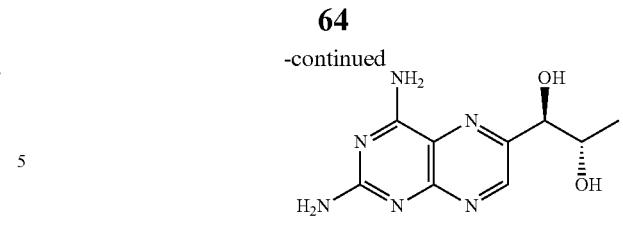

Weigh 77 mg of Na, add into 30 mL of methanol, and stir thoroughly until the reaction is completed. Transfer 3 mL of the above solution, add 32 mg of guanidine HCl, and stir for 5 min under the protection of N2. Filter and remove the insolubles, add 50 mg of compound 2b-3 for reaction. Heat to reflux, and stir overnight. Bright yellow crystals are precipitated. Filter to obtain the precipitated crystals, which are compound 2 (16.8 mg, with a yield of 64%); IR (cm$^{-1}$) v 3329, 2222, 1736, 1625, 1225 $^1$H NMR (500 MHz, DMSO-d6) δ 7.99-7.65 (m, 4H), 7.51-7.36 (m, 3H), 7.34-7.21 (m, 1H), 7.20-7.08 (m, 1H), 5.58 (d, J=4.2 Hz, 1H), 5.31-5.10 (m, 1H), 4.09 (q, J=7.0 Hz, 1H), 3.74 (s, 3H), 1.56 (s, 3H), 1.49 (d, J=7.1 Hz, 3H), 1.10 (d, J=6.6 Hz, 3H); $^{13}$C NMR (126 MHz, DMSO) δ 174.53, 167.36, 157.37, 156.89, 148.58, 138.26, 134.93, 130.35, 129.54, 127.87, 126.92, 126.27, 123.21, 117.72, 112.51, 106.42, 103.14, 73.25, 66.71, 55.36, 47.63, 21.64, 19.83, 12.79. HRMS m/z (ESI+) $C_{24}H_{24}O_5N_4Na^+$ requires: 471.1639; found: 471.1638.

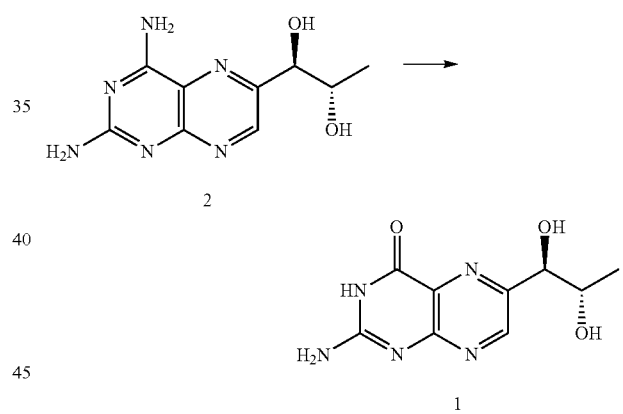

Suspend the obtained 100 mg of compound 2 in 10 mL of NaOH aqueous solution (160 mg), heat to 78° C. and stir for 3 h for reaction. Cool to room temperature, and adjust the pH to 5-6 by adding HCOOH dropwise. Filter to obtain the precipitated crystals, which are compound 1, i.e., the L-erythro biopterin compound (100 mg, purity>99%, yield>99%);

Embodiment 6

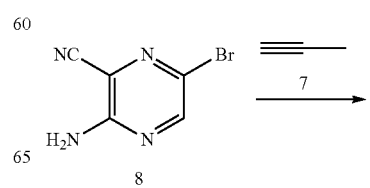

-continued

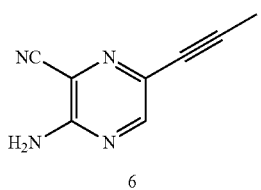

Dissolve 10 g of compound 8 (50 mmol), 475 mg of CuI (2.5 mmol), 440 mg of $PdCl_2$ (2.5 mmol), 1.3 g of TPP (5 mmol), 25.3 g of TEA (250 mmol) and 55 mL of allylene (1 M) in 250 mL of acetonitrile, react and stir at room temperature for 16 h. After the raw materials are completely converted to product, which is monitored by HPLC, add 100 mL of $H_2O$, wash and separate the liquid. Extract the aqueous phase with EA (25 mL×3). Collect the organic phases, dry over $Na_2SO_4$, and perform column chromatography (EA:Heptane=3:1) to obtain compound 6, which are yellow crystals, with a weight of 7.8 g and a yield of 98.7%.

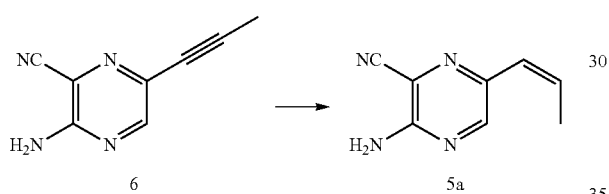

Weigh 2 g of compound 6 (12.5 mmol), and transfer into a hydrogenation kettle. Add 20 mL of 2-MeTHF to dissolve, and add 20 mg of Lindlar Pd. Replace with $H_2$, pressurize to 0.2 MPa and stir at room temperature. After the reaction of raw materials, which is monitored by HPLC, is just completed, filter to remove Lindlar Pd, and concentrate. Perform column chromatography (EA:Heptane=1:3) to obtain 1.9 g of yellow crystals, which are compound 5a. IR (cm) v 3401, 3202, 2222, 1644, 1492, 1515, 1172; $^1$H NMR (500 MHz, DMSO-d6) δ 8.27 (s, 1H), 7.33 (s, 2H), 6.30 (dq, J=11.7, 1.8 Hz, 1H), 5.88 (dq, J=11.7, 7.3 Hz, 1H), 2.01 (dd, J=7.3, 1.8 Hz, 3H); $^{13}$C NMR (126 MHz, DMSO) δ 154.87, 147.91, 141.32, 129.95, 124.29, 116.05, 109.58, 14.88; HRMS m/z (ESI+) $C_8H_9N_4^+$ requires: 161.0822; found: 161.0821.

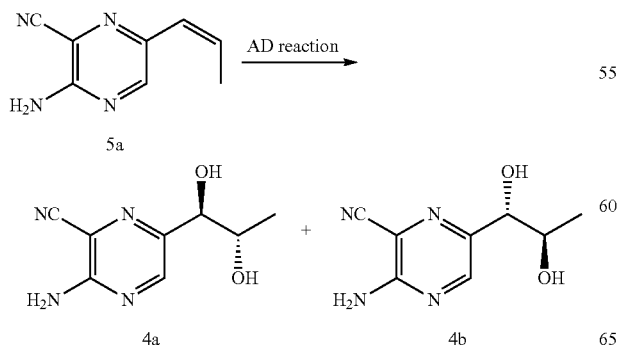

Dissolve 1.5 mg of $K_2OsO_4.2H_2O$ (4 μmol), 20 mg of DHQ-IND (40 μmol), 840 mg of $K_2CO_3$ (6 mmol) and 2 g of $K_3[Fe(CN)_6]$ (6 mmol) in $H_2O$/t-BuOH (10 mL/10 mL), and stir at room temperature until they are completely dissolved. Then add compound 5a, react and stir at room temperature overnight (approximate 18 h). After the reaction is completed, which is monitored by HPLC, separate the liquid, collect the organic phase, and extract the aqueous phase with 2-MeTHF until no residue remains. Dry over $Na_2SO_4$, filter, and concentrate. Perform column chromatography to obtain 110 mg of white crystals, which is a mixture of compounds 4a and 4b (er-62:38).

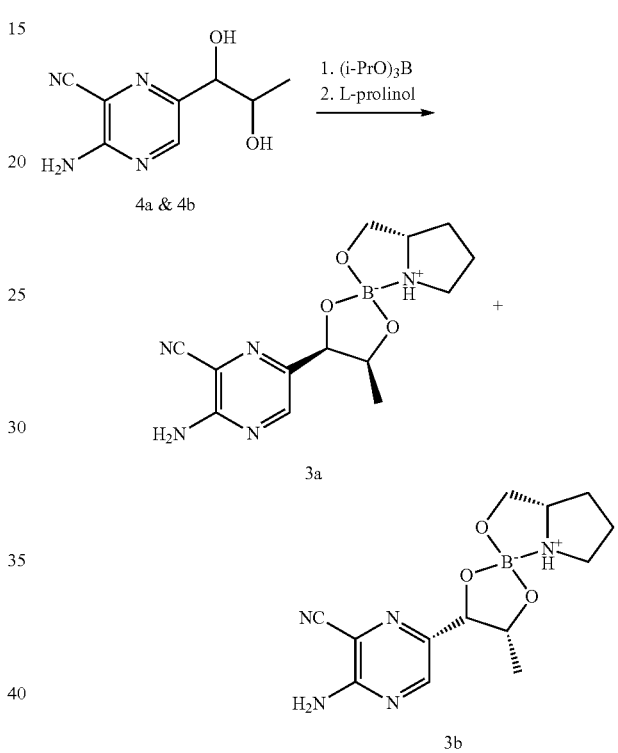

Disperse 220 mg of the above obtained mixture of compounds 4a and 4b (er=62:38) in 5 mL of methylbenzene, and heat to reflux. Add 225 mg of isopropyl borate. After the system is dissolved to be clear, continue to reflux for 30 min. Inject 121 mg of D-Prolinol, and reflux for 30 min. Cool to room temperature, and filter to obtain the precipitated solid. Wash the filter cake thoroughly with 2-MeTHF, and collect the filter cake to obtain compound 3a, which are white crystals, with a weight of 144 mg, a yield of 42%, a chemical purity of 99% and the diastereomer ratio (dr) is 3a:3b=96:4.

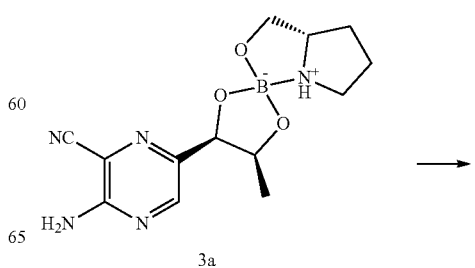

-continued

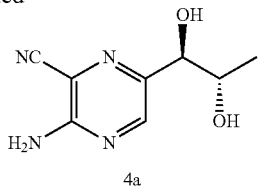

Disperse 1 g of compound 3a (dr=99:1) with 10 mL of 2-MeTHF, add 5 mL of saturated K₂CO₃, stir until it is completely dissolved. Separate the liquid, extract the aqueous phase with 2-MeTHF (10 mL×3), and combine the organic phases. Dry over Na₂SO₄, filter, and concentrate. Perform column chromatography (EA:Heptane=1:3) to obtain 620 mg of white crystals, which are compound 4a (purity: 99%, ee: 98%).

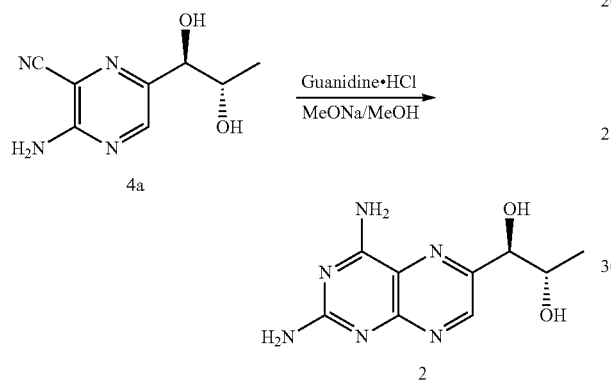

Dissolve 638 mg of guanidine HCl (7.3 mmol) in 7 mL of methanol, add 1.4 mL of sodium methoxide (5 M in MeOH), and stir for 10 min. Filter and remove the precipitated solid. Collect the filtrate, and add 320 mg of compound 4a (1.67 mmol, ee>99%). Heat and reflux overnight. Cool to room temperature and filter the collected filter cake to obtain 250 mg of yellow crystals, which are compound 2 (ee>99.9%, purity: 99%, yield: 64%).

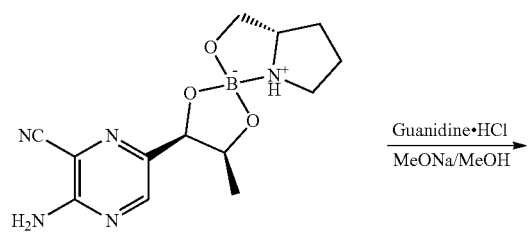

Dissolve 638 mg of guanidine HCl (7.3 mmol) in 7 mL of methanol, add 1.4 mL of sodium methoxide (5 M in MeOH), and stir for 10 min. Filter and remove the precipitated solid. Collect the filtrate, and add 500 mg of compound 3a (1.65 mmol, 3a:3b=94:6). Heat and reflux overnight. Cool to room temperature, filter and collect the filtration cake to obtain 244 mg of yellow crystals, which are compound 2 (ee>99.9%, purity: 99%, yield: 63%).

IR (cm⁻¹) v 3249, 1701, 1537, 1490, 1367, 1127; ¹H NMR (500 MHz, DMSO-d6) δ 11.42 (s, 1H), 8.70 (s, 1H), 6.87 (s, 2H), 5.58 (d, J=4.9 Hz, 1H), 4.69 (d, J=5.3 Hz, 1H), 4.43 (t, J=5.3 Hz, 1H), 3.90 (h, J=6.1 Hz, 1H), 1.05 (d, J=6.3 Hz, 3H); ¹³C NMR (126 MHz, DMSO) δ 161.03, 156.55, 153.61, 151.86, 148.98, 127.08, 76.85, 69.42, 19.11. HRMS m/z (ESI+) C₉H₁₂O₃N₅⁺ requires: 238.0935; found: 238.0935.

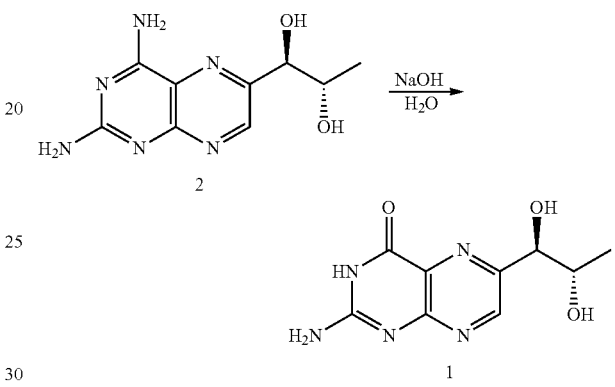

Disperse 89 mg of compound 2 (with a purity of 99%, ee=99.9%) in 5 mL of NaOH aqueous solution (15 mg), heat to 50° C. and stir for 4 h. After the conversion rate of the reaction, which is controlled in-process by HPLC, reaches approximate 90%, supplement 100 mg of NaOH, and heat to 78° C. After the reaction is completed, add 10 mg of activated carbon for decoloration, filter, and wash with 1 mL of butyl alcohol. Separate the liquid, and collect the aqueous phase. Neutralize to pH 7 with 1 M diluted hydrochloric acid to obtain compound 1, which is a white solid, with a weight of 78 mg, a purity of 99%, a yield of 87%, and a ee of 99.9%.
IR (cm⁻¹) v 3249, 1701, 1537, 1490, 1367, 1127; ¹H NMR (500 MHz, DMSO-d6) δ 11.42 (s, 1H), 8.70 (s, 1H), 6.87 (s, 2H), 5.58 (d, J=4.9 Hz, 1H), 4.69 (d, J=5.3 Hz, 1H), 4.43 (t, J=5.3 Hz, 1H), 3.90 (h, J=6.1 Hz, 1H), 1.05 (d, J=6.3 Hz, 3H); ¹³C NMR (126 MHz, DMSO) δ 161.03, 156.55, 153.61, 151.86, 148.98, 127.08, 76.85, 69.42, 19.11. HRMS m/z (ESI+) C₉H₁₂O₃N₅+ requires: 238.0935; found: 238.0935.

Embodiment 7

Prepare a Racemic Mixture of Compounds 4a and 4b as Per Embodiment 1;

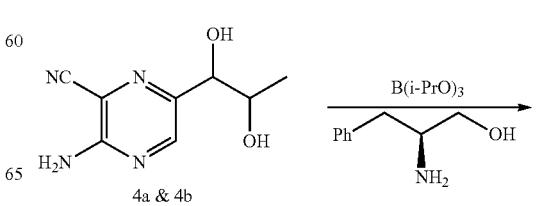

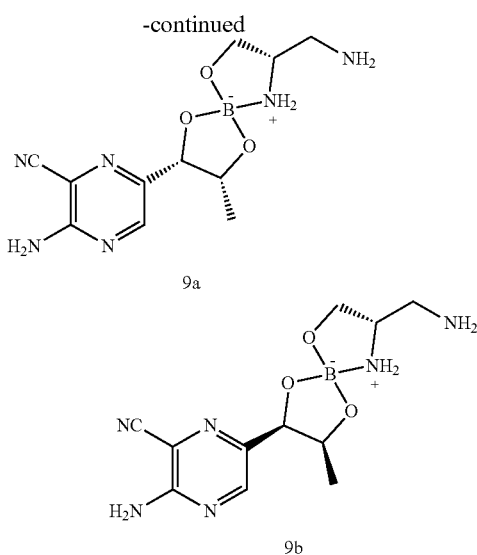

9a

9b

Dissolve 100 mg of the racemic mixture of compounds 4a and 4b in 5 mL of acetonitrile, and add 117 mg of isopropyl borate. Reflux and stir for 30 min. Dissolve 93.4 mg of L-phenylglycinol in acetonitrile, and add into the system. Continue to reflux for about 15 min. Precipitates are formed. Filter to obtain 72 mg of product 9a, which are white crystals, with a chemical purity of 99%, a diastereomer ratio (dr) of 9a:9b=99.2:0.8.

Validation Test of Configuration

Obtain the XRD data of product (Compound 3a,

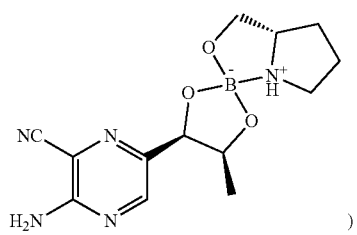

)

formed after separation of L-prolinol. The detection instrument is D8 Venture and the parameters of instrument are shown in Table 1 as below:

TABLE 1

| | |
|---|---|
| Light source: Cu target | X-ray: Cu-Kα (=1.54018 Å) |
| Detector: CMOS area detector | Resolution: 0.80 A |
| Current and voltage: 50 KV, 1.2 A | Exposure time: 5 s |
| Distance from area detector to sample: 40 mm | Test temperature: 173 (2) K |

Structure Elucidation and Refinement Process:

After integration and reduction were performed to the diffraction data using the SAINT program, empirical absorption correction was performed to the data using the SADABS program; the single crystal structure was elucidated by the direct method using SHELXT2014, and the structure was refined using the least squares method. The hydrogen atom refinement was achieved by isotropic computational processing, the hydrogen atom on C—H was obtained by computational hydrogenation, and its refinement was performed using the riding model.

Diffraction intensity data were collected with a D8 Venture diffractometer under the following conditions: Cu target (Cu-Kα (=1.54018 Å)), graphite monochromator, diameter of single guide tube: Φ=0.50 mm, distance from crystal to the COMS detector: d=40 mm, resolution: 0.80 Å, tube pressure: 50 KV, tube flow: 1.2 mA, scan mode: Φ and ω scan, the total number of diffraction points collected: 6738, the number of separate diffraction points: 2751, and the number of viewing point (|F|2≥2σ|F|2): 2709. The Flack constant is −0.03 (7), the chiral center is shown in FIG. 1; the crystal data is shown in Table 2, the data collection is shown in Table 3, the refinement parameters are shown in Table 4, and the results of other specific parameters are shown in Tables 5-7.

TABLE 2

| Crystal data | |
|---|---|
| C13H18BN5O3 | F(000) = 640 |
| Mr = 303.13 | Dx = 1.363 Mg m-3 |
| Monoclinic, C2 | Cu Kα radiation, λ = 1.54184 Å |
| a = 19.8507 (5) Å | Cell parameters from 5850 reflections |
| b = 6.6953 (2) Å | Θ = 4.0-72.2° |
| c = 12.3601 (3) Å | μ = 0.81 mm$^{-1}$ |
| β = 115.925 (1)° | T = 170 K |
| V = 1477.42 (7) Å3 | Block, colourless |
| Z = 4 | 0.19 × 0.12 × 0.08 mm |

TABLE 3

| Data collection | |
|---|---|
| D8 VENTURE diffractometer | Rint = 0.027 |
| Absorption correction: multi-scan SADABS2016/2 (Broker, 2016/2) was used for absorption correction. wR2(int) was 0.1515 before and 0.0479 after correction. The Ratio of minimum to maximum transmission is 0.8576. The ½ correction factor is Not present. | Θmax = 72.2°, Θmin = 4.0° |
| Tmin = 0.646, Tmax = 0.754 | h = −22→24 |
| 6738 measured reflections | k = −8→8 |
| 2751 independent reflections | l = −15→15 |
| 2709 reflections with I > 2σ (I) | |

TABLE 4

| | |
|---|---|
| Refinement on F$^2$ | Hydrogen site location: mixed |
| Least-squares matrix: full | H atoms treated by a mixture of independent and constrained refinement |
| R[F$^2$ > 2σ(F$^2$)] = 0.029 | w = 1/[σ$^2$(Fo$^2$) + (0.0481P)$^2$ + 0.2566P] where P = (Fo$^2$ + 2Fc$^2$)/3 |
| wR(F$^2$) = 0.077 | (Δ/σ) max < 0.001 |
| S = 1.04 | Δ > max = 0.16 e Å$^{-3}$ |
| 2751 reflections | Δ > min = −0.17 e Å$^{-3}$ |
| 205 parameters | Absolute structure: Flack x determined using 1136 quotients [(I+) − (I−)]/[(I+) + (I−)] (Parsons, Flack and Wagner, Acta Cryst. B69 (2013) 249-259). |
| 1 restraint | Absolute structure parameter: 0.03 (7) |

TABLE 5

| Fractional atomic coordinates and isotropic or equivalent isotropic displacement parameters (2) | | | |
|---|---|---|---|
| | X | Y | Z | Uiso*/Ueq |
| O2 | 0.64183 (7) | 0.3466 (2) | 0.90349 (10) | 0.0284 (3) |
| O3 | 0.73919 (7) | 0.53879 (18) | 0.88836 (11) | 0.0272 (3) |

TABLE 5-continued

Fractional atomic coordinates and isotropic or equivalent isotropic displacement parameters (2)

| | X | Y | Z | Uiso*/Ueq |
|---|---|---|---|---|
| O1 | 0.64514 (6) | 0.3533 (2) | 0.71733 (10) | 0.0250 (3) |
| N2 | 0.44700 (8) | 0.4545 (2) | 0.59248 (13) | 0.0261 (3) |
| N1 | 0.75403 (8) | 0.1845 (2) | 0.88956 (13) | 0.0257 (3) |
| N3 | 0.50499 (9) | 0.8426 (3) | 0.63775 (16) | 0.0343 (4) |
| N5 | 0.25974 (10) | 0.5638 (3) | 0.44136 (17) | 0.0421 (4) |
| N4 | 0.38641 (10) | 0.9765 (3) | 0.53837 (19) | 0.0418 (4) |
| H4A | 0.34431 | 0.959052 | 0.54561 | 0.050* |
| H4B | 0.409931 | 1.082673 | 0.580823 | 0.050* |
| C9 | 0.52051 (9) | 0.4867 (3) | 0.65153 (14) | 0.0247 (3) |
| C10 | 0.54820 (10) | 0.6817 (3) | 0.67279 (16) | 0.0302 (4) |
| H10 | 0.600853 | 0.700135 | 0.714619 | 0.036* |
| C6 | 0.57060 (10) | 0.3066 (3) | 0.69661 (15) | 0.0258 (4) |
| H6 | 0.550774 | 0.195661 | 0.636741 | 0.031* |
| C11 | 0.40272 (10) | 0.6161 (3) | 0.55589 (15) | 0.0263 (4) |
| C1 | 0.80696 (10) | 0.4983 (3) | 0.87991 (16) | 0.0288 (4) |
| H1A | 0.846548 | 0.593753 | 0.92966 | 0.035* |
| H1B | 0.799391 | 0.509148 | 0.795464 | 0.035* |
| C7 | 0.57939 (10) | 0.2340 (3) | 0.82101 (16) | 0.0298 (4) |
| H7 | 0.593762 | 0.089638 | 0.829854 | 0.036* |
| C2 | 0.82872 (10) | 0.2853 (3) | 0.92620 (17) | 0.0301 (4) |
| H2 | 0.85831 | 0.284276 | 1.015667 | 0.036* |
| C13 | 0.32331 (10) | 0.5819(3) | 0.49092 (16) | 0.0307 (4) |
| C12 | 0.43054 (10) | 0.8133 (3) | 0.57820 (16) | 0.0303 (4) |
| C5 | 0.74743 (12) | 0.0217 (3) | 0.80192 (18) | 0.0365 (4) |
| H5A | 0.696253 | 0.017265 | 0.735234 | 0.044* |
| H5B | 0.759279 | −0.110065 | 0.842316 | 0.044* |
| C8 | 0.51302 (12) | 0.2583 (4) | 0.84878 (19) | 0.0442 (5) |
| H8A | 0.524991 | 0.201813 | 0.928255 | 0.066* |
| H8B | 0.469703 | 0.188319 | 0.787783 | 0.066* |
| H8C | 0.501252 | 0.400526 | 0.848327 | 0.066* |
| B1 | 0.69082 (11) | 0.3664 (3) | 0.84626 (16) | 0.0242 (4) |
| C3 | 0.86852 (13) | 0.1659 (4) | 0.8665 (2) | 0.0454 (5) |
| H3A | 0.900125 | 0.059633 | 0.920509 | 0.054* |
| H3B | 0.900172 | 0.253516 | 0.843131 | 0.054* |
| C4 | 0.80418 (16) | 0.0773 (4) | 0.7561 (2) | 0.0474 (6) |
| H4C | 0.783299 | 0.176608 | 0.690291 | 0.057* |
| H4D | 0.82071 | −0.041813 | 0.726658 | 0.057* |
| H1 | 0.7538 (12) | 0.131 (3) | 0.954 (2) | 0.019 (5) |

TABLE 6

Atomic displacement parameters

| | U11 | U22 | U33 | U12 | U13 | U23 |
|---|---|---|---|---|---|---|
| O2 | 0.0275 (6) | 0.0368 (7) | 0.0209 (6) | 0.0011 (5) | 0.0104 (5) | −0.0008 (5) |
| O3 | 0.0266 (6) | 0.0268 (6) | 0.0262 (6) | 0.0009 (5) | 0.0098 (5) | −0.0030 (5) |
| O1 | 0.0217 (5) | 0.0321 (6) | 0.0200 (5) | 0.0001 (5) | 0.0079 (4) | 0.0013 (5) |
| N2 | 0.0241 (7) | 0.0331 (8) | 0.0208 (6) | −0.0024 (6) | 0.0094 (5) | 0.0003 (6) |
| N1 | 0.0295 (7) | 0.0266 (7) | 0.0208 (7) | 0.0026 (6) | 0.0109 (5) | 0.0016 (6) |
| N3 | 0.0259 (7) | 0.0318 (8) | 0.0422 (9) | −0.0017 (7) | 0.0122 (6) | −0.0002 (7) |
| N5 | 0.0254 (8) | 0.0602 (12) | 0.0388 (9) | −0.0039 (8) | 0.0122 (7) | −0.0088 (8) |
| N4 | 0.0276 (8) | 0.0350 (9) | 0.0615 (11) | 0.0030 (7) | 0.0181 (8) | 0.0029 (9) |
| C9 | 0.0226 (8) | 0.0319 (9) | 0.0189 (7) | −0.0019 (7) | 0.0083 (6) | 0.0003 (7) |
| C10 | 0.0221 (8) | 0.0333 (9) | 0.0318 (9) | −0.0025 (7) | 0.0087 (7) | −0.0027 (8) |
| C6 | 0.0241 (8) | 0.0296 (9) | 0.0224 (7) | −0.0022 (7) | 0.0089 (6) | −0.0013 (6) |
| C11 | 0.0213 (8) | 0.0341 (9) | 0.0235 (8) | −0.0010 (7) | 0.0097 (6) | −0.0002 (7) |
| C1 | 0.0275 (8) | 0.0332 (9) | 0.0267 (8) | −0.0015 (7) | 0.0127 (7) | −0.0029 (7) |
| C7 | 0.0282 (8) | 0.0353 (9) | 0.0251 (8) | −0.0007 (7) | 0.0111 (7) | 0.0031 (7) |
| C2 | 0.0256 (8) | 0.0378 (10) | 0.0260 (8) | 0.0033 (7) | 0.0103 (7) | 0.0017 (7) |
| C13 | 0.0263 (9) | 0.0393 (9) | 0.0271 (8) | −0.0008 (7) | 0.0123 (7) | −0.0026 (8) |
| C12 | 0.0254 (8) | 0.0347 (10) | 0.0319 (9) | 0.0001 (7) | 0.0134 (7) | 0.0004 (7) |
| C5 | 0.0476 (11) | 0.0272 (9) | 0.0324 (9) | 0.0068 (8) | 0.0152 (9) | −0.0026 (8) |
| C8 | 0.0336 (10) | 0.0711 (15) | 0.0318 (9) | −0.0015 (10) | 0.0180 (8) | 0.0100 (10) |
| B1 | 0.0260 (8) | 0.0251 (9) | 0.0199 (8) | 0.0038 (7) | 0.0086 (7) | 0.0012 (7) |
| C3 | 0.0426 (11) | 0.0460 (12) | 0.0595 (13) | 0.0105 (10) | 0.0333 (10) | 0.0038 (11) |
| C4 | 0.0762 (16) | 0.0385 (11) | 0.0413 (11) | 0.0140 (11) | 0.0385 (12) | 0.0026 (10 |

TABLE 7

Geometric parameters (Å, °)

| O2—C7 | 1.428 (2) | C6—C7 | 1.548 (2) |
|---|---|---|---|
| O2—B1 | 1.437 (2) | C11—C13 | 1.441 (2) |
| O3—C1 | 1.420 (2) | C11—C12 | 1.411 (3) |
| O3—B1 | 1.445 (2) | C1—H1A | 0.99 |
| O1—C6 | 1.422 (2) | C1—H1B | 0.99 |
| O1—B1 | 1.451 (2) | C1—C2 | 1.527 (3) |
| N2—C9 | 1.333 (2) | C7—H7 | 1 |
| N2—C11 | 1.342 (2) | C7—C8 | 1.508 (3) |
| N1—C2 | 1.507 (2) | C2—H2 | 1 |
| N1—C5 | 1.502 (2) | C2—C3 | 1.523 (3) |
| N1—B1 | 1.660 (2) | C5—H5A | 0.99 |
| N1—H1 | 0.88 (2) | C5—H5B | 0.99 |
| N3—C10 | 1.327 (3) | C5—C4 | 1.513 (3) |
| N3—C12 | 1.346 (2) | C8—H8A | 0.9800 |
| N5—C13 | 1.143 (3) | C8—H8B | 0.9800 |
| N4—H4A | 0.8861 | C8—H8C | 0.9800 |
| N4—H4B | 0.8860 | C3—H3A | 0.9900 |
| N4—C12 | 1.351 (3) | C3—H3B | 0.9900 |
| C9—C10 | 1.396 (3) | C3—C4 | 1.524 (4) |
| C9—C6 | 1.506 (2) | C4—H4C | 0.9900 |
| C10—H10 | 0.9500 | C4—H4D | 0.9900 |
| C6—H6 | 1.0000 | | |
| C7—O2—B1 | 105.08 (13) | N1—C2—C1 | 103.04 (13) |
| C1—O3—B1 | 108.83 (14) | N1—C2—H2 | 110.7 |
| C6—O1—B1 | 108.20 (13) | N1—C2—C3 | 105.66 (17) |
| C9—N2—C11 | 116.93 (16) | C1—C2—H2 | 110.7 |
| C2—N1—B1 | 105.90 (14) | C3—C2—C1 | 115.48 (17) |
| C2—N1—H1 | 107.7 (14) | C3—C2—H2 | 110.7 |
| C5—N1—C2 | 107.82 (15) | N5—C13—C11 | 176.6 (2) |
| C5—N1—B1 | 118.98 (13) | N3—C12—N4 | 117.58 (18) |
| C5—N1—H1 | 109.2 (14) | N3—C12—C11 | 119.05 (17) |
| B1—N1—H1 | 106.7 (14) | N4—C12—C11 | 123.31 (16) |
| C10—N3—C12 | 117.29 (17) | N1—C5—H5A | 110.9 |
| H4A—N4—H4B | 108.8 | N1—C5—H5B | 110.9 |
| C12—N4—H4A | 110.3 | N1—C5—C4 | 104.31 (17) |
| C12—N4—H4B | 110.1 | H5A—C5—H5B | 108.9 |
| N2—C9—C10 | 120.07 (17) | C4—C5—H5A | 110.9 |
| N2—C9—C6 | 117.42 (16) | C4—C5—H5B | 110.9 |
| C10—C9—C6 | 122.48 (15) | C7—C8—H8A | 109.5 |
| N3—C10—C9 | 123.57 (16) | C7—C8—H8B | 109.5 |
| N3—C10—H10 | 118.2 | C7—C8—H8C | 109.5 |
| C9—C10—H10 | 118.2 | H8A—C8—H8B | 109.5 |

TABLE 7-continued

| Geometric parameters (Å, °) | | | |
|---|---|---|---|
| O1—C6—C9 | 110.96 (14) | H8A—C8—H8C | 109.5 |
| O1—C6—H6 | 109.8 | H8B—C8—H8C | 109.5 |
| O1—C6—C7 | 103.51 (13) | O2—B1—O3 | 112.50 (14) |
| C9—C6—H6 | 109.8 | O2—B1—O1 | 107.61 (14) |
| C9—C6—C7 | 112.86 (15) | O2—B1—N1 | 110.64 (14) |
| C7—C6—H6 | 109.8 | O3—B1—O1 | 116.20 (15) |
| N2—C11—C13 | 117.11 (17) | O3—B1—N1 | 100.38 (13) |
| N2—C11—C12 | 123.09 (15) | O1—B1—N1 | 109.33 (14) |
| C12—C11—C13 | 119.80 (17) | C2—C3—H3A | 111.1 |
| O3—C1—H1A | 110.6 | C2—C3—H3B | 111.1 |
| O3—C1—H1B | 110.6 | C2—C3—C4 | 103.25 (17) |
| O3—C1—C2 | 105.82 (14) | H3A—C3—H3B | 109.1 |
| H1A—C1—H1B | 108.7 | C4—C3—H3A | 111.1 |
| C2—C1—H1A | 110.6 | C4—C3—H3B | 111.1 |
| C2—C1—H1B | 110.6 | C5—C4—C3 | 103.32 (17) |
| O2—C7—C6 | 103.23 (14) | C5—C4—H4C | 111.1 |
| O2—C7—H7 | 108.4 | C5—C4—H4D | 111.1 |
| O2—C7—C8 | 110.64 (16) | C3—C4—H4C | 111.1 |
| C6—C7—H7 | 108.4 | C3—C4—H4D | 111.1 |
| C8—C7—C6 | 117.49 (16) | H4C—C4—H4D | 109.1 |
| C8—C7—H7 | 108.4 | | |

The technical features of the above-mentioned embodiments can be combined arbitrarily. In order to make the description concise, not all possible combinations of the various technical features in the above-mentioned embodiments are described. However, as long as there is no contradiction in the combinations of these technical features, all of the combinations should be considered within the scope of this specification.

The above-mentioned embodiments only express several embodiments of the present invention, and the descriptions are more specific and detailed, but they should not be understood as limitations to the scope of the patent of the present invention. It should be pointed out that for ordinary technician in the field, under the premise of not deviating from the idea of the invention, several modifications and improvements can be made, and these all fall within the protection scope of the present invention. Therefore, the protection scope of the patent of the present invention should be subject to the appended claims.

The invention claimed is:

1. A method for preparing an L-erythro biopterin compound, wherein the L-erythro biopterin compound has the structure shown in formula (I), and the L-erythro biopterin compound represented by formula (I) is prepared by dihydroxylation of the compound represented by formula (II) or the compound represented by formula (III);

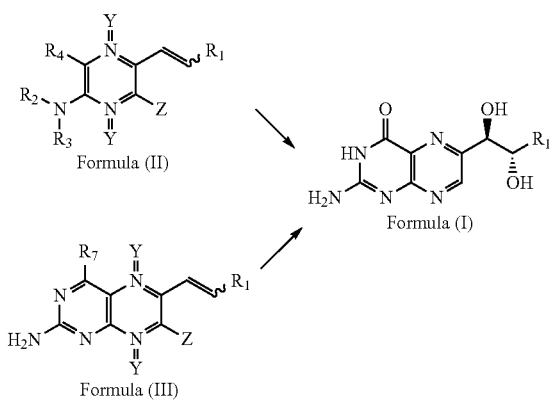

Formula (II)

Formula (III)

Formula (I)

wherein
Y is O or absent;
Z is a hydrogen atom or a leaving group;
$R_1$ is a substituted or unsubstituted alkyl, a substituted or unsubstituted cycloalkyl, a substituted or unsubstituted heterocycloalkyl, a substituted or unsubstituted aryl, or a substituted or unsubstituted heteroaryl;
$R_2$ and $R_3$ are independently a hydrogen atom or an amino protecting group; and $R_2$ and $R_3$ together with the nitrogen atom connected to $R_2$ and $R_3$ can form a cyclic lactim group;
$R_4$ is —$COOR_5$, —$CONR_6$ or —CN;
$R_5$ and $R_6$ are independently a hydrogen atom, a substituted or unsubstituted alkyl, a substituted or unsubstituted cycloalkyl, a substituted or unsubstituted heterocycloalkyl, a substituted or unsubstituted aryl, or a substituted or unsubstituted heteroaryl;
$R_7$ is —OH or —$NH_2$.

2. The method for preparing the L-erythro biopterin compound according to claim 1, wherein $R_5$ and $R_6$ are independently selected from: hydrogen atom, or substituted or unsubstituted $C_{1-20}$ alkyl;
$R_1$ is selected from: $C_{1-6}$ alkyl, 3-8 membered cycloalkyl, 3-10 membered aryl, 3-10 membered heteroaryl, TMS, TBS, or —$CH_2X$; X is a leaving group.

3. The method for preparing the L-erythro biopterin compound according to claim 2, wherein the leaving group is selected from: silicyl group, halogen, $OSO_nR_9$, $OCOR_{10}$ or $OPO_2R_{11}$; in which $R_9$, $R_{10}$ or $R_{11}$ is independently selected from: —$CF_3$, alkyl, phenyl, or alkyl substituted phenyl, n is 0, 1 or 2; and/or
the amino protecting group is selected from: -Boc, -Cbz, —Ac, -Ts, -Ms, -Bz, -Bn, -PMB, or schiff base.

4. The method for preparing the L-erythro biopterin compound according to claim 3, wherein Y is absent, Z is a hydrogen atom, $R_4$ is a cyano, and $R_1$ is a methyl.

5. The method for preparing the L-erythro biopterin compound according to claim 1, wherein when the alkene in the compound represented by formula (II) is of a cis structure and its structural formula is represented by formula (IIa), the steps for preparing L-erythro biopterin compound represented by formula (I) from the compound represented by formula (IIa) are as follows:
the compound represented by formula (IIa) undergoes a dihydroxylation reaction to obtain the compound to be separated which is composed of the compounds represented by formula (IVa) and formula (IVa');
the compound to be separated is separated by chiral separation reagent set to obtain the compound represented by formula (IVa-1);
the compound represented by formula (IVa-1) undergoes a cyclization reaction with

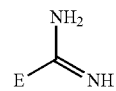

and/or the salt of

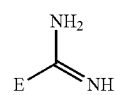

followed by a hydrolysis reaction to obtain the L-erythro biopterin compound represented by formula (I);

among them, the chiral separation reagent set includes the first reagent and the second reagent, the first reagent is boric acid ester or boric acid;

the second reagent is chiral amino alcohol;

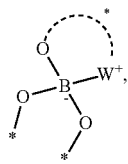

W, Z, Y, $R_1$, $R_2$, $R_3$, $R_4$, $R_5$ and $R_6$ are as defined in claim 1;

E is halogen, $C_{1-4}$ alkoxy, $C_{1-4}$ alkyl sulphanyl or —$NH_2$;

the compound represented by formula (IVa) undergoes a cyclization reaction with $$\underset{E}{\overset{NH_2}{\diagup}}\diagdown_{NH}$$

and/or the salt of $$\underset{E}{\overset{NH_2}{\diagup}}\diagdown_{NH}$$

followed by a hydrolysis reaction to obtain the L-erythro biopterin compound represented by formula (I);

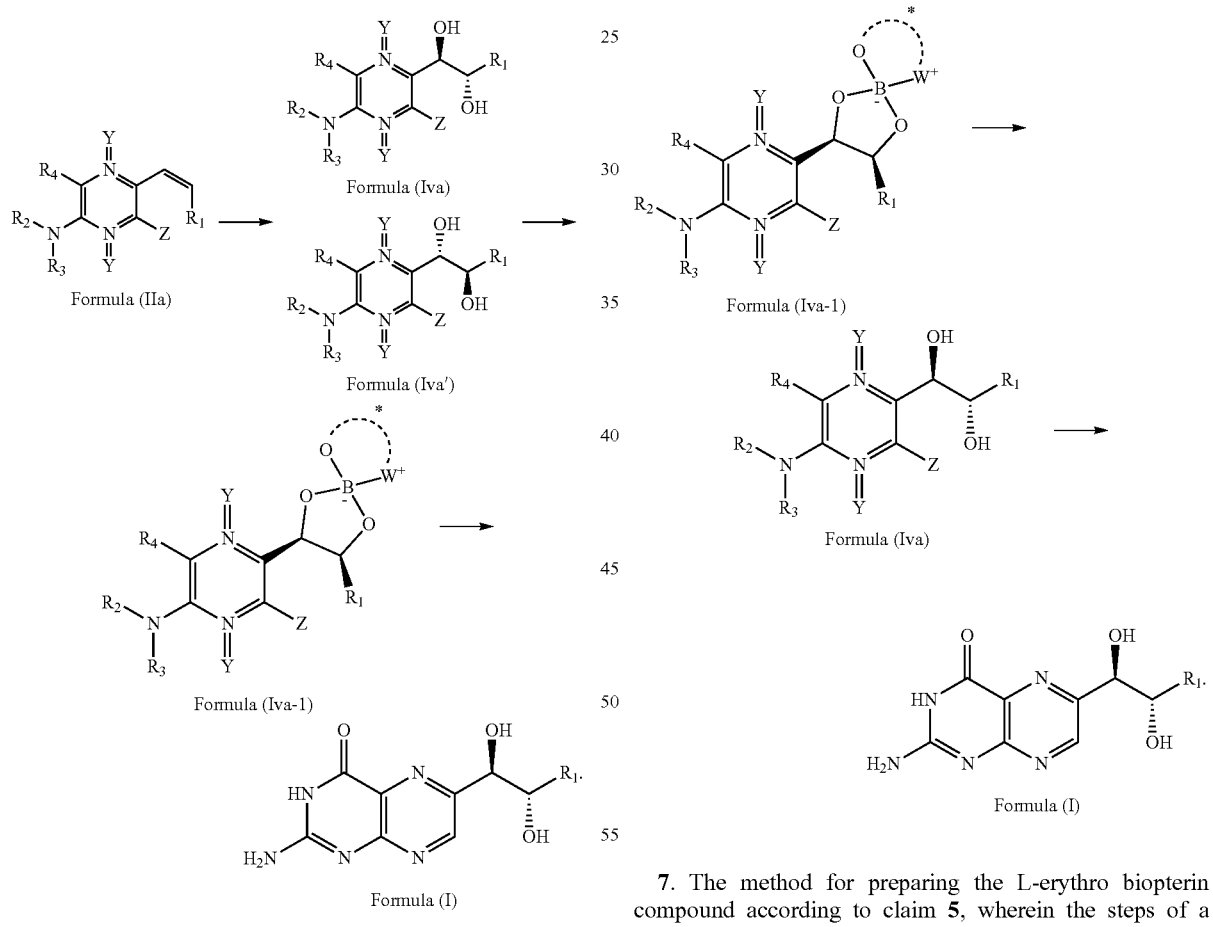

6. The method for preparing the L-erythro biopterin compound according to claim 5, wherein after the steps for obtaining the compound represented by formula (IVa-1), there are also the following steps:

mix the compound represented by formula (IVa-1) with protonic solvent to obtain the compound represented by formula (IVa);

7. The method for preparing the L-erythro biopterin compound according to claim 5, wherein the steps of a cyclization reaction of the compound represented by formula (IVa-1) with $$\underset{E}{\overset{NH_2}{\diagup}}\diagdown_{NH}$$

and/or the salt of

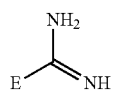

followed by a hydrolysis reaction are as follows: mix the compound represented by formula (IVa-1),

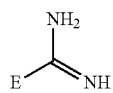

and/or the salt of

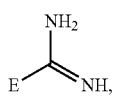

base and protonic solvent, and heat to 50-100° C. for reaction; after the reaction is completed, cool; a solid substance is precipitated; filter to obtain the compound represented by formula (I-1); add the compound represented by formula (I-1) into an alkaline solution; after the reaction is completed, add acid, and adjust the pH to 5-6; crystals are precipitated; filter and dry to obtain the L-erythro biopterin compound represented by formula (I);

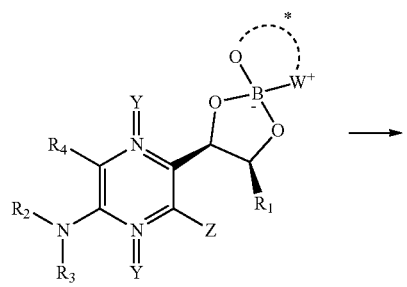

Formula (Iva-1)

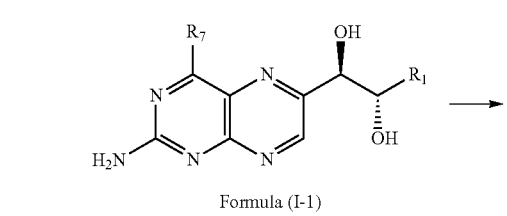

Formula (I-1)

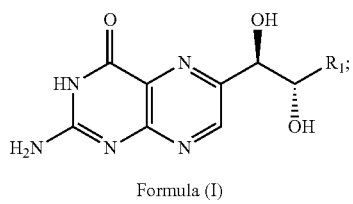

Formula (I)

$R_7$ is —OH or —$NH_2$.

8. The method for preparing the L-erythro biopterin compound according to claim 5, wherein the boric acid ester is selected from: trimethyl borate, triethyl borate, triisopropyl borate or isopropoxyboronic acid pinacol ester;

the chiral amino alcohol is selected from: L-phenylglycinol, L-prolinol, L-phenylalaninol, (S)-(−)-α,α-diphenylprolinol, quinine or cinchoni.

9. The method for preparing the L-erythro biopterin compound according to claim 1, wherein when the alkene in the compound represented by formula (II) is of a trans structure and its structural formula is represented by formula (IIb), the steps for preparing the L-erythro biopterin compound represented by formula (I) from the compound represented by formula (IIb) are as follows:

the compound represented by the formula (IIb) is subjected to a dihydroxylation reaction to prepare the compound represented by the formula (IVb-1) and/or formula (IVb-2);

the compound represented by formula (IVb-1) and/or formula (IVb-2) undergoes an acetylation reaction to obtain the compound represented by formula (VIIb-1) and/or formula (VIIb-2);

the compound represented by formula (VIIb-1) and/or formula (VIIb-2) undergoes the Mitsunobu reaction to obtain the compound represented by formula (VIIb-3) and/or formula (VIIb-4);

the compound represented by (VIIb-3) and/or formula (VIIb-4) undergoes a cyclization reaction with

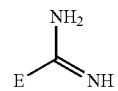

and/or the salt of

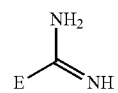

to obtain the L-erythro biopterin compound represented by formula (I);

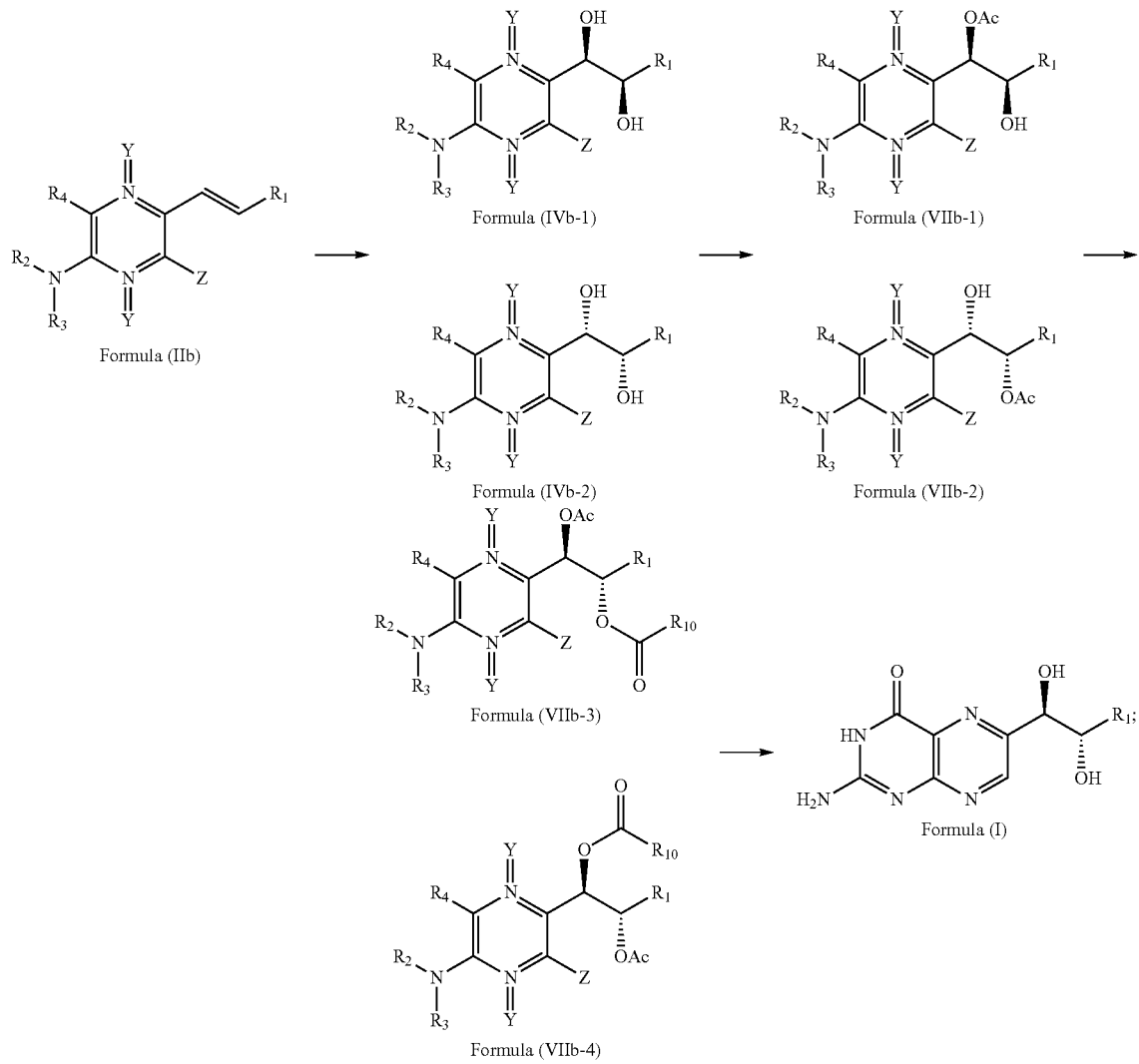

wherein $R_{10}$ is substituted or unsubstituted alkyl, substituted or unsubstituted cycloalkyl, substituted or unsubstituted heterocyclic alkyl, substituted or unsubstituted aryl, or substituted or unsubstituted heteroaryl;

E is halogen, $C_{1-4}$ alkoxy, $C_{1-4}$ alkylthio or —$NH_2$.

10. The method for preparing the L-erythro biopterin compound according to claim 1, wherein the dihydroxylation reaction method is Sharpless asymmetric dihydroxylation reaction, basic $KMnO_4$ dihydroxylation reaction, Fe-catalyzed dihydroxylation or asymmetric epoxidation followed by hydrolysis and ring opening.

11. The method for preparing the L-erythro biopterin compound according to claim 10, wherein the compound represented by formula (IIa) and/or formula (IIb) undergoes a dihydroxylation reaction by the Sharpless asymmetric dihydroxylation reaction; wherein the steps of the Sharpless asymmetric dihydroxylation reaction are as follows:

Mix the compound represented by formula (IIa) and/or the compound represented by formula (IIb), oxidizing agent, dihydroxylation reagent, base, ligand, and solvent for reactions after the reaction is completed, quench the reaction, and separate;

among them, the dihydroxylation reagent is selected from one or more of the following reagents: $OsO_4$, $K_2OsO_4$, $OsO_4$ hydrate and $K_2OsO_4$ hydrate;

the oxidant is selected from one or more of the following reagents: $K_3[Fe(CN)_6]$ or NMO;

the base is selected from one or more of potassium carbonate, sodium carbonate, cesium carbonate, potassium bicarbonate, sodium bicarbonate, NaOH, KOH, LiOH, $NH_4OH$, t-BuONa, t-BuOK, t-BuOLi, cesium carbonate, triethylamine, diisopropylethylamine, DBU, pyridine and p-dimethylaminopyridine;

the ligand is selected from one or more of the following reagents: $(DHQ)_2PHAL$, $(DHQD)_2PHAL$, DHQ-IND and DHQD-IND.

12. The method for preparing the L-erythro biopterin compound according to claim 1, wherein, when the alkene in the compound represented by formula (II) is of a cis structure and its structural formula is represented by formula (IIa), the compound represented by formula (IIa) is obtained by a catalytic hydrogenation reaction of the compound represented by formula (V):

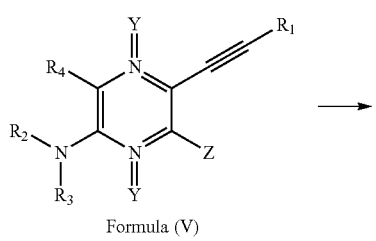

Formula (V)

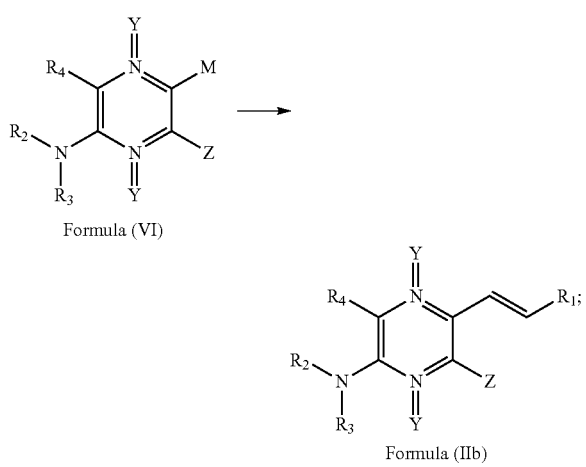

Formula (IIa)

when the alkene in the compound represented by the formula (II) is of a trans structure and its structural formula is represented by formula (IIb), the compound represented by formula (IIb) is obtained by a coupling reaction of the compound represented by formula (VI);

Formula (VI)

Formula (IIb)

in which M is H or a leaving group.

13. The method for preparing the L-erythro biopterin compound according to claim 12, wherein the steps of the catalytic hydrogenation reaction are as follows:
 mix the compound represented by formula (V), catalyst and solvent, and react under hydrogen atmosphere; after the reaction is completed, filter and concentrate to obtain the compound represented by formula (IIa);
 the catalyst is selected from one or more of the following reagents: Lindlar catalyst, palladium/carbon, Raney nickel, platinum black and platinum dioxide;
 the solvent is selected from one or more of the following reagents: tetrahydrofuran, 2-methyltetrahydrofuran, ethyl ether, methyl tert-butyl ether, methyl cyclopentyl ether, methanol, ethanol, isopropanol, acetonitrile and toluene.

14. The method for preparing the L-erythro biopterin compound according to claim 12, wherein the steps of the coupling reaction are as follows:
 mix the compound represented by formula (VI), trans-1-propenyl boronic acid reagent, catalyst, solvent and ligand for reaction; after the reaction is completed, separate to obtain the compound represented by formula (IIb);
 the trans-1-propenyl boronic acid reagent is selected from: trans-1-propenyl boronic acid pinacol ester, trans-1-propenyl boronic acid or trans-1-propenyl fluoroborate;
 the catalyst is selected from one or more of the following reagents: 5% Pd/C, 10% Pd/C, Pd(OAc)$_2$, PdCl$_2$(PPh$_3$)$_2$, Pd(PPh$_3$)$_4$, PdCl$_2$(dppf), PdCl$_2$(MeCN)$_2$ and Pd$_2$(dba)$_3$;
 the solvent is selected from one or more of the following reagents: methanol, ethanol, isopropanol, butanol, water, tetrahydrofuran, 2-methyltetrahydrofuran, 1,4-dioxane, DME, DMF, DMSO, NMP, acetonitrile, dichloromethane, 1,2-dichloroethane, methyl acetate, ethyl acetate, isopropyl acetate, butyl acetate, ethyl ether, methyl tert-butyl ether, toluene, xylene, acetone, methyl ethyl ketone and methyl cyclopentane;
 the ligands is selected from one or more of the following reagents: PPh$_3$, BINAP, dppf, Xantphos, Xphos monophosphorus and diphosphorus ligands.

15. The method for preparing the L-erythro biopterin compound according to claim 12, wherein the compound represented by formula (V) is obtained by the Sonogashira reaction of the compound represented by formula (VI);

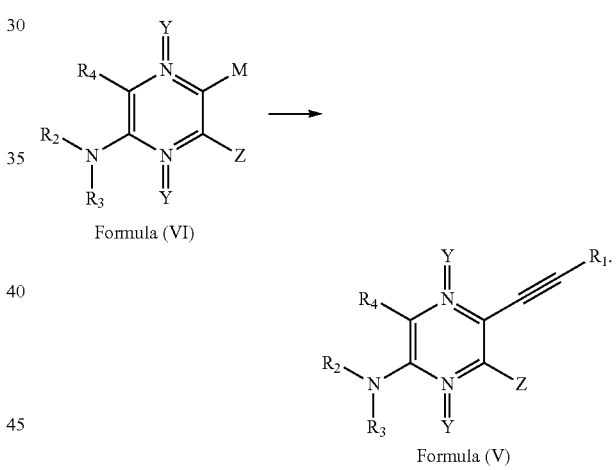

Formula (VI)

Formula (V)

16. The method for preparing the L-erythro biopterin compound according to claim 15, wherein the steps of the Sonogashira reaction are as follows:
 mix the compound represented by formula (VI), catalyst, ligand and solvent;
 add the base and

for reaction; after the reaction is completed, quench the reaction, and separate to obtain the compound represented by formula (V).

17. The method for preparing the L-erythro biopterin compound according to claim 1, wherein the compound represented by formula (III) is obtained by a cyclization reaction of the compound represented by formula (II) with and/or the salt of

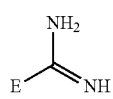

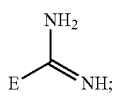

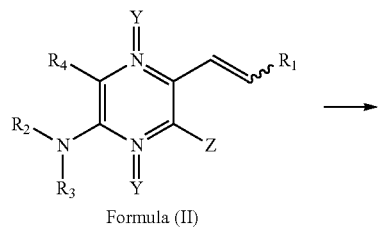

Formula (II)

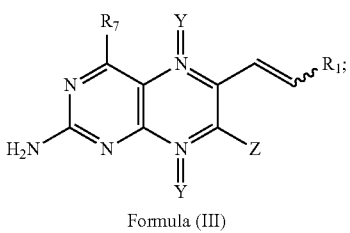

Formula (III)

E is halogen, $C_{1-4}$ alkoxy, $C_{1-4}$ alkylthio or —$NH_2$.

18. The method for preparing the L-erythro biopterin compound according to claim 1, wherein,
when the alkene in the compound represented by the formula (III) is of a cis structure and its structural formula is represented by formula (IIIa), the compound represented by formula (IIIa) is obtained by a catalytic hydrogenation reaction of the compound represented by formula (VIII):

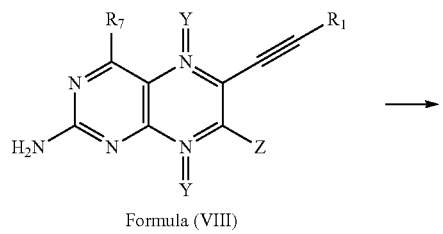

Formula (VIII)

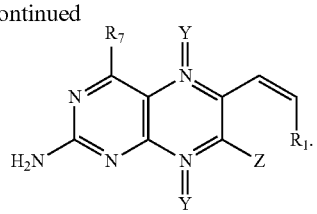

Formula (IIIa)

19. The method for preparing the L-erythro biopterin compound according to claim 18, wherein the compound represented by formula (VIII) is prepared by the following steps:
the compound represented by formula (VI) undergoes the Sonogashira reaction to obtain the compound represented by formula (V);
the compound represented by formula (V) undergoes cyclization to obtain the compound represented by formula (VIII);

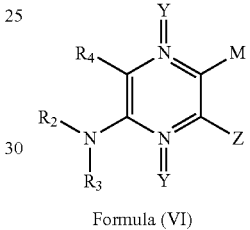

Formula (VI)

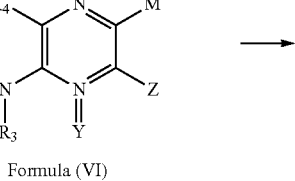

Formula (V)

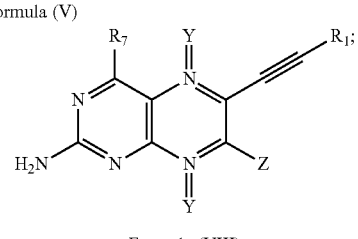

Formula (VIII)

wherein M is H or a leaving group.

* * * * *